United States Patent
Ludowise et al.

(10) Patent No.: US 9,725,762 B2
(45) Date of Patent: Aug. 8, 2017

(54) SYSTEMS AND METHODS FOR DETECTING THE PRESENCE OF A SELECTED VOLUME OF MATERIAL IN A SAMPLE PROCESSING DEVICE

(71) Applicant: Diasorin S.P.A., Saluggia (Vercelli) (IT)

(72) Inventors: Peter D. Ludowise, Cottage Grove, MN (US); David A. Whitman, St. Paul, MN (US); Kyle C. Armantrout, Los Angeles, CA (US); Maurice Exner, San Clemente, CA (US); Lucien A. E. Jacky, Orange, CA (US); Michelle Tabb, Santa Ana, CA (US)

(73) Assignee: Diasorin S.P.A., Saluggia (Vercelli) (IT)

( * ) Notice: Subject to any disclaimer, the term of this patent is extended or adjusted under 35 U.S.C. 154(b) by 0 days.

(21) Appl. No.: 14/881,506

(22) Filed: Oct. 13, 2015

(65) Prior Publication Data
US 2016/0040213 A1 Feb. 11, 2016

Related U.S. Application Data

(62) Division of application No. 13/474,903, filed on May 18, 2012, now Pat. No. 9,168,523.
(Continued)

(51) Int. Cl.
*G01N 21/00* (2006.01)
*C12Q 1/68* (2006.01)
(Continued)

(52) U.S. Cl.
CPC ............ *C12Q 1/686* (2013.01); *B01L 3/5027* (2013.01); *B01L 3/502715* (2013.01);
(Continued)

(58) Field of Classification Search
None
See application file for complete search history.

(56) References Cited

U.S. PATENT DOCUMENTS

| 3,555,284 A | 1/1971 | Anderson |
| 3,595,386 A | 7/1971 | Hradel |

(Continued)

FOREIGN PATENT DOCUMENTS

| CN | 1346058 A | 4/2002 |
| DE | 3712624 | 11/1988 |

(Continued)

OTHER PUBLICATIONS

US 6,200,755, 03/2001, Virtanen (withdrawn)
(Continued)

*Primary Examiner* — Robert Xu
(74) *Attorney, Agent, or Firm* — Michael Fainberg; Arent Fox LLP

(57) ABSTRACT

Systems and methods for processing sample processing devices. The system can include a sample processing device comprising a detection chamber, a motor configured to rotate the sample processing device about an axis of rotation, and an optical module operatively positioned relative to the sample processing device and configured to determine whether a selected volume of material is present in the detection chamber of the sample processing device. The method can include rotating the sample processing device about an axis of rotation, and determining whether a selected volume of material is present in the detection chamber, while rotating the sample processing device. In some embodiments, determining whether a selected volume of material is present can be performed by optically interrogating the detection chamber for an optical property of the material.

16 Claims, 25 Drawing Sheets

Related U.S. Application Data

(60) Provisional application No. 61/487,618, filed on May 18, 2011.

(51) Int. Cl.
  *B01L 3/00* (2006.01)
  *G01N 21/64* (2006.01)
  *G01N 35/02* (2006.01)
  *G01N 35/04* (2006.01)

(52) U.S. Cl.
  CPC ....... *G01N 21/6486* (2013.01); *G01N 35/025* (2013.01); *G01N 35/04* (2013.01); *B01L 2200/0605* (2013.01); *B01L 2300/087* (2013.01); *B01L 2400/0409* (2013.01); *G01N 2035/0441* (2013.01)

(56) References Cited

U.S. PATENT DOCUMENTS

| | | |
|---|---|---|
| 3,713,124 A | 1/1973 | Durland et al. |
| 3,795,451 A | 3/1974 | Mailen |
| 3,798,459 A | 3/1974 | Anderson et al. |
| 3,856,470 A | 12/1974 | Cullis et al. |
| 3,873,217 A | 3/1975 | Anderson et al. |
| 3,912,799 A | 10/1975 | Chisholm |
| 3,964,867 A | 6/1976 | Berry |
| 4,030,834 A | 6/1977 | Bauer et al. |
| 4,046,511 A | 9/1977 | Stabile |
| 4,111,304 A | 9/1978 | Lucas |
| 4,123,173 A | 10/1978 | Bullock et al. |
| 4,244,916 A | 1/1981 | Guigan |
| 4,252,538 A | 2/1981 | Barr |
| 4,256,696 A | 3/1981 | Soodak |
| 4,284,602 A | 8/1981 | Kelton |
| 4,298,570 A | 11/1981 | Lillig et al. |
| 4,384,193 A | 5/1983 | Kledzik et al. |
| 4,390,499 A | 6/1983 | Curtis et al. |
| 4,396,579 A | 8/1983 | Schroeder et al. |
| D271,993 S | 12/1983 | Swartz |
| 4,456,581 A | 6/1984 | Edelmann et al. |
| D274,553 S | 7/1984 | Perry |
| 4,476,733 A | 10/1984 | Chlosta et al. |
| 4,488,810 A | 12/1984 | Hatanaka et al. |
| 4,498,896 A | 2/1985 | Leis |
| D277,891 S | 3/1985 | Uffenheimer et al. |
| 4,554,436 A | 11/1985 | Chlosta et al. |
| 4,580,896 A | 4/1986 | Brickus et al. |
| 4,580,898 A | 4/1986 | Keramaty et al. |
| 4,632,908 A | 12/1986 | Schultz |
| D288,124 S | 2/1987 | Brickus et al. |
| 4,673,657 A | 6/1987 | Christian |
| 4,695,430 A | 9/1987 | Coville et al. |
| 4,766,078 A | 8/1988 | Gang |
| 4,814,279 A | 3/1989 | Sugaya |
| 4,839,296 A | 6/1989 | Kennedy et al. |
| 4,906,432 A | 3/1990 | Geiselman |
| 4,933,146 A | 6/1990 | Meyer et al. |
| 4,981,801 A | 1/1991 | Suzuki et al. |
| 4,990,075 A | 2/1991 | Wogoman |
| 5,089,233 A | 2/1992 | DeVaney, Jr. et al. |
| D329,024 S | 9/1992 | Marks |
| 5,149,505 A | 9/1992 | English et al. |
| 5,160,702 A | 11/1992 | Kopf-Sill |
| 5,182,083 A | 1/1993 | Barker et al. |
| 5,207,987 A | 5/1993 | Kureshy et al. |
| 5,219,526 A | 6/1993 | Long |
| 5,229,297 A | 7/1993 | Schnipelsky et al. |
| 5,254,479 A | 10/1993 | Chemelli |
| 5,258,163 A | 11/1993 | Krause et al. |
| 5,264,184 A | 11/1993 | Aysta et al. |
| 5,278,377 A | 1/1994 | Tsai |
| 5,281,516 A | 1/1994 | Stapleton et al. |
| 5,288,463 A | 2/1994 | Chemelli |
| 5,310,523 A | 5/1994 | Smethers et al. |
| 5,336,467 A | 8/1994 | Heidt et al. |
| 5,411,065 A | 5/1995 | Meador et al. |
| 5,415,839 A | 5/1995 | Zaun et al. |
| 5,422,271 A | 6/1995 | Chen et al. |
| 5,438,128 A | 8/1995 | Nieuwkerk et al. |
| 5,439,649 A | 8/1995 | Tseung et al. |
| 5,460,780 A | 10/1995 | Devaney, Jr. et al. |
| 5,464,541 A | 11/1995 | Aysta et al. |
| 5,475,610 A | 12/1995 | Atwood et al. |
| 5,496,518 A | 3/1996 | Arai et al. |
| 5,496,520 A | 3/1996 | Kelton et al. |
| 5,525,514 A | 6/1996 | Jacobs et al. |
| 5,550,228 A | 8/1996 | Godiard et al. |
| 5,571,410 A | 11/1996 | Swedberg et al. |
| 5,576,218 A | 11/1996 | Zurek et al. |
| 5,578,270 A | 11/1996 | Reichler et al. |
| 5,587,128 A | 12/1996 | Wilding et al. |
| 5,593,838 A | 1/1997 | Zanzucchi et al. |
| 5,599,501 A | 2/1997 | Carey et al. |
| 5,601,141 A | 2/1997 | Gordon et al. |
| 5,602,756 A | 2/1997 | Atwood et al. |
| 5,604,130 A | 2/1997 | Warner et al. |
| 5,616,301 A | 4/1997 | Moser et al. |
| 5,637,469 A | 6/1997 | Wilding et al. |
| 5,639,428 A | 6/1997 | Cottingham |
| 5,693,233 A | 12/1997 | Schembri |
| 5,700,695 A | 12/1997 | Yassinzadeh |
| RE35,716 E | 1/1998 | Stapleton et al. |
| 5,720,923 A | 2/1998 | Haff et al. |
| 5,721,123 A | 2/1998 | Hayes et al. |
| 5,726,026 A | 3/1998 | Wilding et al. |
| 5,770,029 A | 6/1998 | Nelson et al. |
| 5,795,547 A | 8/1998 | Moser et al. |
| 5,800,785 A | 9/1998 | Bochner |
| 5,804,141 A | 9/1998 | Chianese |
| 5,811,296 A | 9/1998 | Chemelli et al. |
| 5,819,842 A | 10/1998 | Potter et al. |
| 5,833,923 A | 11/1998 | McClintock et al. |
| 5,846,396 A | 12/1998 | Zanzucchi et al. |
| 5,856,194 A | 1/1999 | Arnquist et al. |
| 5,863,502 A | 1/1999 | Southgate et al. |
| 5,863,801 A | 1/1999 | Southgate et al. |
| 5,869,002 A | 2/1999 | Limon et al. |
| 5,876,675 A | 3/1999 | Kennedy |
| 5,886,863 A | 3/1999 | Nagasaki et al. |
| 5,922,617 A | 7/1999 | Wang et al. |
| 5,948,227 A | 9/1999 | Dubrow |
| 5,976,468 A | 11/1999 | Godec et al. |
| 5,997,818 A | 12/1999 | Hacker et al. |
| 6,001,643 A | 12/1999 | Spaulding |
| 6,007,690 A | 12/1999 | Nelson et al. |
| 6,013,513 A | 1/2000 | Reber et al. |
| 6,015,534 A | 1/2000 | Atwood |
| 6,015,674 A | 1/2000 | Woudenberg |
| 6,030,581 A | 2/2000 | Virtanen |
| 6,048,457 A | 4/2000 | Kopaciewicz et al. |
| 6,063,589 A | 5/2000 | Kellogg et al. |
| 6,068,751 A | 5/2000 | Neukermans |
| 6,074,827 A | 6/2000 | Nelson et al. |
| 6,103,199 A | 8/2000 | Bjornson et al. |
| 6,126,765 A | 10/2000 | Ohman |
| 6,143,247 A | 11/2000 | Sheppard, Jr. et al. |
| 6,143,248 A | 11/2000 | Kellogg et al. |
| 6,153,012 A | 11/2000 | Rupp et al. |
| 6,153,148 A | 11/2000 | Thomas |
| 6,168,759 B1 | 1/2001 | Green et al. |
| 6,168,948 B1 | 1/2001 | Anderson et al. |
| 6,183,693 B1 | 2/2001 | Bogen et al. |
| 6,184,029 B1 | 2/2001 | Wilding et al. |
| 6,190,617 B1 | 2/2001 | Clark et al. |
| 6,197,595 B1 | 3/2001 | Anderson et al. |
| 6,200,474 B1 | 3/2001 | Kopaciewicz et al. |
| D441,873 S | 5/2001 | Köhler |
| 6,235,531 B1 | 5/2001 | Kopf-Sill |
| 6,265,168 B1 | 7/2001 | Gjerde et al. |
| 6,284,113 B1 | 9/2001 | Bjornson et al. |
| 6,296,809 B1 | 10/2001 | Richards et al. |
| 6,302,134 B1 | 10/2001 | Kellogg et al. |
| 6,306,273 B1 | 10/2001 | Wainright et al. |

(56) References Cited

U.S. PATENT DOCUMENTS

| | | |
|---|---|---|
| 6,319,469 B1 | 11/2001 | Mian et al. |
| 6,338,820 B1 | 1/2002 | Hubbard et al. |
| 6,344,326 B1 | 2/2002 | Nelson et al. |
| 6,375,898 B1 | 4/2002 | Ulrich et al. |
| 6,391,264 B2 | 5/2002 | Hammer et al. |
| 6,399,025 B1 | 6/2002 | Chow |
| 6,399,361 B2 | 6/2002 | Brotherston et al. |
| 6,413,782 B1 | 7/2002 | Parce et al. |
| 6,414,136 B1 | 7/2002 | Spicer |
| 6,432,365 B1 | 8/2002 | Levin et al. |
| 6,440,725 B1 | 8/2002 | Pourahmadi et al. |
| 6,450,047 B2 | 9/2002 | Swedberg et al. |
| 6,461,287 B1 | 10/2002 | Glater |
| 6,465,225 B1 | 10/2002 | Fuhr et al. |
| 6,467,275 B1 | 10/2002 | Ghoshal |
| 6,479,300 B1 | 11/2002 | Jiang et al. |
| 6,527,432 B2 | 3/2003 | Kellogg et al. |
| 6,532,997 B1 | 3/2003 | Bedingham et al. |
| 6,548,788 B2 | 4/2003 | Kellogg et al. |
| 6,558,947 B1 | 5/2003 | Lund et al. |
| 6,565,808 B2 | 5/2003 | Hudak et al. |
| 6,566,637 B1 | 5/2003 | Revesz et al. |
| 6,572,830 B1 | 6/2003 | Burdon et al. |
| 6,582,659 B1 | 6/2003 | Murata |
| 6,582,662 B1 | 6/2003 | Kellogg et al. |
| 6,593,143 B1 | 7/2003 | Gordon |
| 6,613,513 B1 | 9/2003 | Parce et al. |
| 6,613,525 B2 | 9/2003 | Nelson et al. |
| 6,617,136 B2 | 9/2003 | Parthasarathy et al. |
| 6,620,478 B1 | 9/2003 | Ohman |
| 6,627,159 B1 | 9/2003 | Bedingham et al. |
| 6,632,399 B1 | 10/2003 | Kellogg et al. |
| 6,632,655 B1 | 10/2003 | Mehta et al. |
| 6,632,656 B1 | 10/2003 | Thomas et al. |
| 6,648,853 B1 | 11/2003 | McEntee |
| 6,660,147 B1 | 12/2003 | Woudenberg et al. |
| 6,663,833 B1 | 12/2003 | Stave et al. |
| 6,664,104 B2 | 12/2003 | Pourahmadi et al. |
| 6,692,596 B2 | 2/2004 | Moll et al. |
| 6,706,519 B1 | 3/2004 | Kellogg et al. |
| 6,709,869 B2 | 3/2004 | Mian |
| 6,719,682 B2 | 4/2004 | Kellogg et al. |
| 6,720,187 B2 | 4/2004 | Bedingham et al. |
| 6,723,236 B2 | 4/2004 | Fisk et al. |
| 6,730,516 B2 | 5/2004 | Jedrzejewski et al. |
| 6,734,401 B2 | 5/2004 | Bedingham et al. |
| 6,752,961 B2 | 6/2004 | Kopf-Sill |
| 6,780,818 B2 | 8/2004 | Gundel et al. |
| 6,814,935 B2 | 11/2004 | Harms et al. |
| 6,818,760 B1 | 11/2004 | Spicer et al. |
| 6,824,738 B1 | 11/2004 | Neeper et al. |
| 6,833,536 B2 | 12/2004 | Shigeura |
| 6,852,851 B1 | 2/2005 | Tooke et al. |
| 6,889,468 B2 | 5/2005 | Bedingham et al. |
| 6,972,113 B1 | 12/2005 | Ramshaw |
| 6,987,253 B2 | 1/2006 | Bedingham et al. |
| 6,992,181 B2 | 1/2006 | Tooke et al. |
| 7,026,168 B2 | 4/2006 | Bedingham et al. |
| 7,105,300 B2 | 9/2006 | Parce et al. |
| 7,164,107 B2 | 1/2007 | Bedingham et al. |
| 7,192,560 B2 | 3/2007 | Parthasarathy et al. |
| 7,198,759 B2 | 4/2007 | Bryning et al. |
| 7,201,881 B2 | 4/2007 | Cox et al. |
| 7,238,269 B2 | 7/2007 | Gason et al. |
| 7,250,260 B2 | 7/2007 | Wenz et al. |
| 7,273,591 B2 | 9/2007 | Sellers et al. |
| 7,294,812 B2 | 11/2007 | Shigeura |
| D557,425 S | 12/2007 | Nakamura et al. |
| 7,312,611 B1 | 12/2007 | Harrison et al. |
| D559,993 S | 1/2008 | Nagakubo et al. |
| D559,994 S | 1/2008 | Nagakubo et al. |
| D560,284 S | 1/2008 | Nagakubo et al. |
| 7,322,254 B2 | 1/2008 | Bedingham et al. |
| 7,323,660 B2 | 1/2008 | Kellogg et al. |
| 7,332,326 B1 | 2/2008 | Kellogg et al. |
| D564,667 S | 3/2008 | Bedingham et al. |
| 7,344,865 B2 | 3/2008 | Parce et al. |
| 7,347,976 B2 | 3/2008 | Parthasarathy et al. |
| 7,396,508 B1 | 7/2008 | Richards et al. |
| 7,435,933 B2 | 10/2008 | Bedingham et al. |
| 7,445,752 B2 | 11/2008 | Harms |
| 7,491,305 B2 | 2/2009 | Woudenberg et al. |
| 7,507,575 B2 | 3/2009 | Bedingham |
| 7,527,763 B2 | 5/2009 | Bedingham |
| 7,566,538 B2 | 7/2009 | Parce et al. |
| 7,569,186 B2 | 8/2009 | Bedingham et al. |
| D600,722 S | 9/2009 | Yabe et al. |
| 7,595,200 B2 | 9/2009 | Bedingham |
| D605,206 S | 12/2009 | Yabe et al. |
| 7,628,954 B2 | 12/2009 | Gomm et al. |
| 7,678,334 B2 | 3/2010 | Bedingham |
| 7,678,576 B2 | 3/2010 | Sasaki et al. |
| 7,709,249 B2 | 5/2010 | Bedingham |
| 7,754,474 B2 | 7/2010 | Aysta et al. |
| 7,763,210 B2 | 7/2010 | Bedingham et al. |
| 7,767,937 B2 | 8/2010 | Bedingham et al. |
| 7,837,947 B2 | 11/2010 | Bedingham |
| 7,855,083 B2 | 12/2010 | Bedingham |
| 7,857,141 B2 | 12/2010 | Park et al. |
| 7,867,767 B2 | 1/2011 | Bedingham |
| 7,871,827 B2 | 1/2011 | Parthasarathy |
| D638,550 S | 5/2011 | Bedingham |
| D638,951 S | 5/2011 | Bedingham |
| 7,935,522 B2 | 5/2011 | Thomas et al. |
| 7,981,600 B2 | 7/2011 | Parthasarathy et al. |
| 8,007,733 B2 | 8/2011 | Shigeura |
| 8,030,062 B2 | 10/2011 | Thomas et al. |
| 8,034,628 B2 | 10/2011 | Harrison et al. |
| 8,080,409 B2 | 12/2011 | Aysta et al. |
| 8,092,759 B2 | 1/2012 | Bedingham et al. |
| 8,226,908 B2 | 7/2012 | Zucchelli et al. |
| D667,561 S | 9/2012 | Bedingham et al. |
| D672,467 S | 12/2012 | Smith |
| 8,343,428 B2 | 1/2013 | Yokogawa |
| 8,388,901 B2 | 3/2013 | Shigeura et al. |
| 2001/0045000 A1 | 11/2001 | Gundel et al. |
| 2001/0055812 A1 | 12/2001 | Mian et al. |
| 2002/0001848 A1 | 1/2002 | Bedingham et al. |
| 2002/0047003 A1 | 4/2002 | Bedingham et al. |
| 2002/0048533 A1 | 4/2002 | Harms et al. |
| 2002/0064885 A1 | 5/2002 | Bedingham et al. |
| 2002/0076354 A1 | 6/2002 | Cohen |
| 2002/0097632 A1 | 7/2002 | Kellogg |
| 2003/0013203 A1 | 1/2003 | Jedrzejewski et al. |
| 2003/0017567 A1 | 1/2003 | Parthasarathy et al. |
| 2003/0044322 A1 | 3/2003 | Andersson et al. |
| 2003/0053934 A1 | 3/2003 | Andersson et al. |
| 2003/0118804 A1 | 6/2003 | Bedingham et al. |
| 2003/0120062 A1 | 6/2003 | Parthasarathy et al. |
| 2003/0124506 A1 | 7/2003 | Bedingham et al. |
| 2003/0138779 A1 | 7/2003 | Parthasarathy et al. |
| 2003/0152491 A1 | 8/2003 | Kellogg et al. |
| 2003/0152994 A1 | 8/2003 | Woudenberg et al. |
| 2003/0155034 A1 | 8/2003 | De Beukeleer et al. |
| 2003/0195106 A1 | 10/2003 | Kellogg et al. |
| 2003/0228706 A1 | 12/2003 | Ramstad et al. |
| 2003/0231878 A1 | 12/2003 | Shigeura |
| 2004/0007275 A1 | 1/2004 | Hui Liu |
| 2004/0016702 A1 | 1/2004 | Hennessy et al. |
| 2004/0016898 A1 | 1/2004 | Cox et al. |
| 2004/0018116 A1 | 1/2004 | Desmond et al. |
| 2004/0018117 A1 | 1/2004 | Desmond et al. |
| 2004/0023371 A1 | 2/2004 | Fawcett |
| 2004/0053290 A1 | 3/2004 | Terbrueggen |
| 2004/0055956 A1 | 3/2004 | Harrold |
| 2004/0121471 A1 | 6/2004 | Dufresne et al. |
| 2004/0131502 A1 | 7/2004 | Cox et al. |
| 2004/0179974 A1 | 9/2004 | Bedingham et al. |
| 2004/0191125 A1 | 9/2004 | Kellogg |
| 2004/0209258 A1 | 10/2004 | Parthasarathy et al. |
| 2005/0028587 A1 | 2/2005 | Baer |
| 2005/0036911 A1 | 2/2005 | Sellers et al. |
| 2005/0041525 A1 | 2/2005 | Pugia et al. |
| 2005/0109396 A1 | 5/2005 | Zucchelli et al. |

(56) References Cited

U.S. PATENT DOCUMENTS

| | | |
|---|---|---|
| 2005/0126312 A1 | 6/2005 | Bedingham et al. |
| 2005/0129583 A1 | 6/2005 | Bedingham et al. |
| 2005/0130177 A1 | 6/2005 | Bedingham et al. |
| 2005/0136545 A1 | 6/2005 | Schmid et al. |
| 2005/0142563 A1 | 6/2005 | Haddad et al. |
| 2005/0142570 A1 | 6/2005 | Parthasarathy et al. |
| 2005/0142571 A1 | 6/2005 | Parthasarathy et al. |
| 2005/0142663 A1 | 6/2005 | Parthasarathy et al. |
| 2005/0180890 A1 | 8/2005 | Bedingham et al. |
| 2005/0224337 A1 | 10/2005 | Iwasaki et al. |
| 2005/0277195 A1 | 12/2005 | Holmquist et al. |
| 2005/0282290 A1 | 12/2005 | Fujimoto et al. |
| 2006/0013732 A1 | 1/2006 | Parthasarathy et al. |
| 2006/0040273 A1 | 2/2006 | Chaiken et al. |
| 2006/0076346 A1 | 4/2006 | Bedingham et al. |
| 2006/0159592 A1 | 7/2006 | Andersson et al. |
| 2006/0228811 A1 | 10/2006 | Bedingham |
| 2007/0007270 A1 | 1/2007 | Bedingham et al. |
| 2007/0009382 A1 | 1/2007 | Bedingham |
| 2007/0009383 A1 | 1/2007 | Bedingham |
| 2007/0009391 A1 | 1/2007 | Bedingham et al. |
| 2007/0010007 A1 | 1/2007 | Aysta et al. |
| 2007/0105213 A1 | 5/2007 | Bryning et al. |
| 2007/0132723 A1 | 6/2007 | Lurz et al. |
| 2007/0142780 A1 | 6/2007 | Van Lue |
| 2007/0160504 A1 | 7/2007 | Parthasarathy |
| 2008/0050276 A1 | 2/2008 | Bedingham et al. |
| 2008/0056949 A1 | 3/2008 | Lee |
| 2008/0058991 A1 | 3/2008 | Lee |
| 2008/0138247 A1 | 6/2008 | Inganas et al. |
| 2008/0149190 A1 | 6/2008 | Bedingham |
| 2008/0152546 A1 | 6/2008 | Bedingham et al. |
| 2008/0156079 A1 | 7/2008 | Momose |
| 2008/0314895 A1 | 12/2008 | Bedingham |
| 2009/0068062 A1 | 3/2009 | Jafari et al. |
| 2009/0111675 A1 | 4/2009 | Yokogawa |
| 2009/0143250 A1 | 6/2009 | Lee |
| 2009/0181366 A1 | 7/2009 | Ong et al. |
| 2009/0258415 A1 | 10/2009 | Bryning et al. |
| 2009/0263280 A1 | 10/2009 | Bedhingham et al. |
| 2010/0050751 A1 | 3/2010 | Lee |
| 2010/0129878 A1 | 5/2010 | Parthasarathy |
| 2010/0167304 A1 | 7/2010 | Bedingham |
| 2010/0240124 A1 | 9/2010 | Aysta |
| 2010/0266456 A1 | 10/2010 | Bedingham |
| 2011/0027904 A1 | 2/2011 | Bedingham |
| 2011/0053785 A1 | 3/2011 | Bedingham |
| 2011/0117607 A1 | 5/2011 | Bedingham |
| 2011/0117656 A1 | 5/2011 | Robole |
| 2011/0124132 A1 | 5/2011 | Kim |
| 2011/0172403 A1 | 7/2011 | Harrold |

FOREIGN PATENT DOCUMENTS

| | | |
|---|---|---|
| JP | 2005-274241 | 10/2005 |
| JP | 2009-216395 | 9/2009 |
| WO | WO 94/26414 | 11/1994 |
| WO | WO 95/19781 | 7/1995 |
| WO | WO 95/33986 | 12/1995 |
| WO | WO 96/41864 | 12/1996 |
| WO | WO 96/41865 | 12/1996 |
| WO | WO 97/21090 | 6/1997 |
| WO | WO 97/46707 | 12/1997 |
| WO | WO 98/49340 | 11/1998 |
| WO | WO 98/50147 | 11/1998 |
| WO | WO 99/15888 | 4/1999 |
| WO | WO 99/44740 | 9/1999 |
| WO | WO 99/67639 | 12/1999 |
| WO | WO 00/35583 | 6/2000 |
| WO | WO 00/40750 | 7/2000 |
| WO | WO 00/69560 | 11/2000 |
| WO | WO 00/78455 | 12/2000 |
| WO | WO 01/07892 | 2/2001 |
| WO | WO 01/12327 | 2/2001 |
| WO | WO 02/00347 | 1/2002 |
| WO | WO 2004/010760 | 2/2004 |
| WO | WO 2004/011142 | 2/2004 |
| WO | WO 2004/011143 | 2/2004 |
| WO | WO 2004/011149 | 2/2004 |
| WO | WO 2004/011365 | 2/2004 |
| WO | WO 2004/011592 | 2/2004 |
| WO | WO 2005/016532 | 2/2005 |
| WO | WO 2006/052200 A1 | 5/2006 |
| WO | WO 2006/085071 A2 | 8/2006 |
| WO | WO 2008/157689 | 12/2008 |
| WO | WO 2009/085884 | 7/2009 |

OTHER PUBLICATIONS

Chiou et al., "A Closed-Cycle Capillary Polymerase Chain Reaction Machine", Analytical Chemistry, vol. 73, No. 9, May 1, 2001, 2018-2021.

Leu et al., "Pressure barrier of capillary stop valves in micro sample separators," *Sensors and Actuators*, 2004;115:508-515.

International Preliminary Report on Patentability for PCT/US2012/038498 dated Nov. 28, 2013; 6 pgs.

International Search Report and Written Opinion of PCT/US2012/038498, dated Aug. 9, 2012, 6 pgs.

Zhou et al., "Reproducibility of Tear Meniscus Measurement by Fourier-Domain Optical Coherence Tomography: A Pilot Study," *Ophthalmic Surgery, Lasers and Imaging*, 2009;40(5):442-447.

SYSTEMS AND METHODS FOR DETECTING THE PRESENCE OF A SELECTED VOLUME OF MATERIAL IN A SAMPLE PROCESSING DEVICE

CROSS-REFERENCE TO RELATED APPLICATIONS

This application is a divisional patent application of U.S. patent application Ser. No. 13/474,903, filed on May 18, 2012 and claims the benefit of U.S. Provisional Application Ser. No. 61/487,618 filed 18 May 2011, entitled "SYSTEMS AND METHODS FOR DETECTING THE PRESENCE OF A SELECTED VOLUME OF MATERIAL IN A SAMPLE PROCESSING DEVICE," both of which are incorporated herein by reference in their entireties.

GRANT INFORMATION

The present invention may have been made with support from the U.S. Government under U.S. Department of Health & Human Services Biomedical Advanced Research & Development Authority (BARDA) Grant No. HHS0100201000049C.

FIELD

The present disclosure generally relates to sample processing, or assaying, devices, systems and methods, particularly, to systems and methods for determining whether a selected volume of material is present in a particular chamber of a sample processing device, and more particularly, to systems and methods for optically interrogating a particular chamber on a sample processing device to determine whether a selected volume of material is present in the chamber.

BACKGROUND

Optical disk systems can be used to perform various biological, chemical or bio-chemical assays, such as genetic-based assays or immunoassays. In such systems, a rotatable disk with multiple chambers can be used as a medium for storing and processing fluid specimens, such as blood, plasma, serum, urine or other fluid. The multiple chambers on one disk can allow for simultaneous processing of multiple portions of one sample, or of multiple samples, thereby reducing the time and cost to process multiple samples, or portions of one sample.

Examples of some reactions that may require accurate chamber-to-chamber temperature control, comparable temperature transition rates, and/or rapid transitions between temperatures include, e.g., the manipulation of nucleic acid samples to assist in the deciphering of the genetic code. Nucleic acid manipulation techniques can include amplification methods such as polymerase chain reaction (PCR); target polynucleotide amplification methods such as self-sustained sequence replication (3SR) and strand-displacement amplification (SDA); methods based on amplification of a signal attached to the target polynucleotide, such as "branched chain" DNA amplification; methods based on amplification of probe DNA, such as ligase chain reaction (LCR) and QB replicase amplification (QBR); transcription-based methods, such as ligation activated transcription (LAT) and nucleic acid sequence-based amplification (NASBA); and various other amplification methods, such as repair chain reaction (RCR) and cycling probe reaction (CPR). Other examples of nucleic acid manipulation techniques include, e.g., Sanger sequencing, ligand-binding assays, etc.

PCR can be used for nucleic acid sequence analysis. In particular, PCR can be used for DNA sequencing, cloning, genetic mapping, and other forms of nucleic acid sequence analysis.

In general, PCR relies on the ability of DNA-copying enzymes to remain stable at high temperatures. There are three major steps in PCR: denaturation, annealing, and extension. During the denaturation, a liquid sample is heated at approximately 94° C. During this process, double DNA strands "melt" open into single stranded DNA and all enzymatic reactions stop. During annealing, the single stranded DNA is cooled to 54° C. At this temperature, primers bind or "anneal" to the ends of the DNA strands. During extension, the sample is heated to 75° C. At this temperature, nucleotides add to the primers and eventually a complementary copy of the DNA template is formed.

There are a number of existing PCR instruments designed to determine levels of specific DNA and RNA sequences in the sample during the PCR in real-time. Many of the instruments are based on the use of fluorescent dyes. In particular, many conventional real-time PCR instruments detect a fluorescent signal produced proportionally during amplification of a PCR product.

SUMMARY

Systems and methods for processing sample processing devices of the present disclosure can be used to determine the presence of material in a sample processing device. In some embodiments, the sample processing device can be a "sample to answer" consumable device, or "disk," that is processed, handled and assayed using a sample processing system and method. Such systems and methods can include means and steps for identifying errors or failures in the performance of the disks during processing. When errors are identified, a run can be interrupted or invalidated, and/or an error or failure report can be generated. In some embodiments, if a failure occurs in the disk, a material (e.g., a sample) may not adequately be moved to a detection chamber that will later be analyzed or interrogated for the presence or absence of an analyte of interest. As a result, the systems, methods and devices of the present disclosure can be used to determine whether a material is present in a particular detection chamber to determine or confirm the validity of the assay results. If the material is not present, it can be inferred that a failure occurred in transferring the material to the detection chamber, and false assay results can be avoided.

Some aspects of the present disclosure provide a method for processing sample processing devices. The method can include providing a sample processing device comprising a detection chamber; rotating the sample processing device about an axis of rotation; and determining whether a selected volume of material is present in the detection chamber, while rotating the sample processing device.

Some aspects of the present disclosure provide a method for processing sample processing devices. The method can include providing a sample processing device comprising a detection chamber; rotating the sample processing device about an axis of rotation; and optically interrogating the detection chamber for an optical property of a material to determine whether the material is present in the detection chamber, wherein optically interrogating occurs while rotating the sample processing device.

Some aspects of the present disclosure provide a method for processing sample processing devices. The method can include providing a sample processing device comprising a processing array. The processing array can include an input chamber, a detection chamber, and a channel positioned to fluidly couple the input chamber and the detection chamber. The method can further include positioning a sample in the input chamber of the processing array of the sample processing device, and rotating the sample processing device about an axis of rotation to move the sample to the detection chamber. The method can further include, after rotating the sample processing device to move the sample to the detection chamber, optically interrogating the detection chamber for an optical property of the sample to determine whether the sample has moved to the detection chamber. The sample processing device can be rotated while optically interrogating the detection chamber.

Some aspects of the present disclosure provide a method for processing sample processing devices. The method can include providing a sample processing device comprising a processing array. The processing array can include an input chamber, a detection chamber, and a channel positioned to fluidly couple the input chamber and the detection chamber. The method can further include positioning a sample in the input chamber of at least one processing array in the sample processing device; and rotating the sample processing device about an axis of rotation to move the sample to the detection chamber. The method can further include optically interrogating the detection chamber of the processing array before rotating the sample processing device to move the sample to the detection chamber to obtain a first background scan, and optically interrogating the detection chamber of the processing array to obtain a second scan after rotating the sample processing device to move the sample to the detection chamber. The sample processing device can be rotated about the axis of rotation while optically interrogating the detection chamber to obtain at least one of the first background scan and the second scan. The method can further include comparing the first background scan with the second scan to determine if a threshold change exists between the first background scan and the second scan.

Some aspects of the present disclosure provide a system for processing sample processing devices. The system can include a sample processing device comprising a detection chamber; a motor configured to rotate the sample processing device about an axis of rotation; an optical module operatively positioned relative to the sample processing device and configured to determine whether a selected volume of material is present in the detection chamber of the sample processing device.

Other features and aspects of the present disclosure will become apparent by consideration of the detailed description and accompanying drawings.

DETAILED DESCRIPTION

Figure 1:
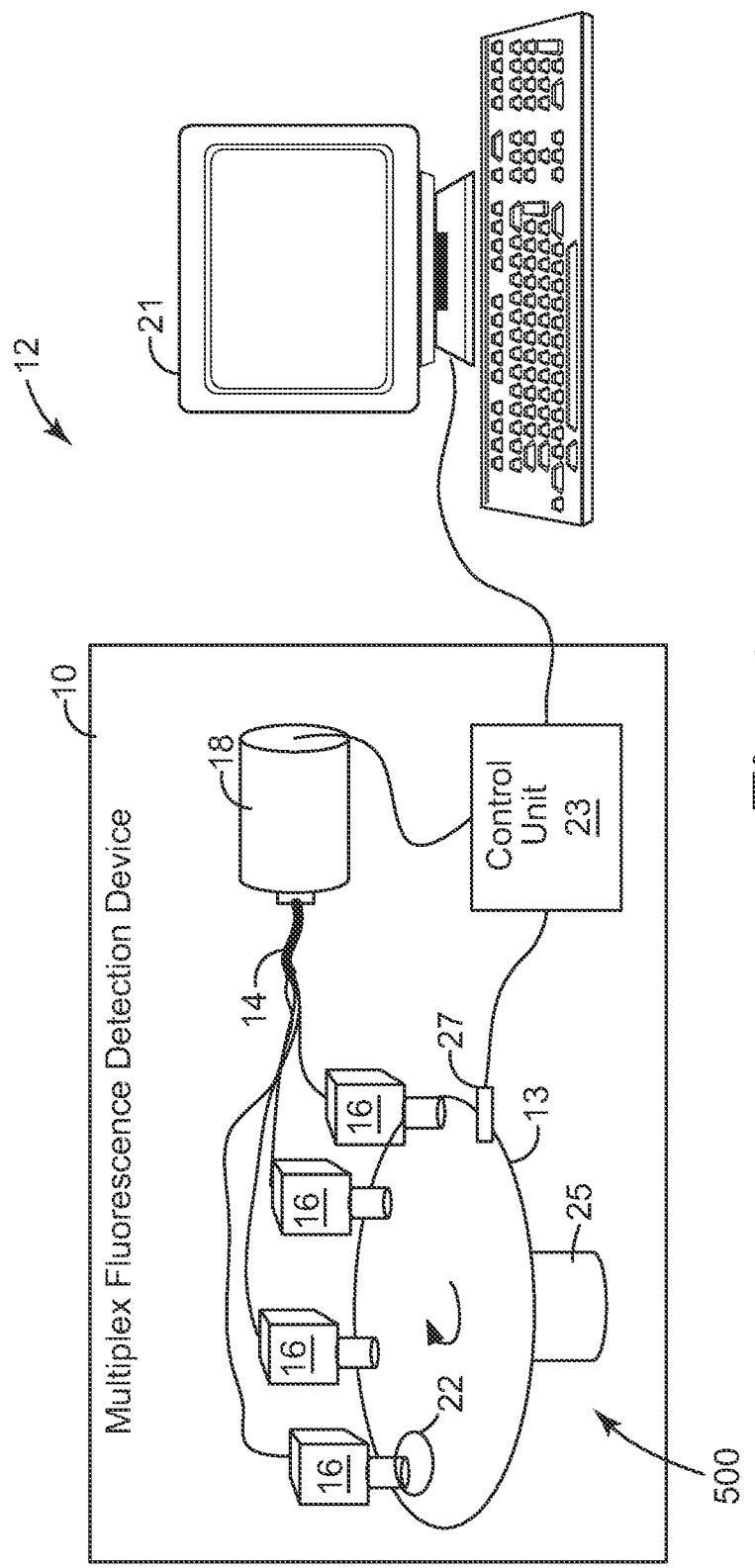
FIG. 1 is a schematic diagram of a sample processing system according to one embodiment of the present disclosure, the system including a multiplex fluorescence detection device, a data acquisition device, and a disk handling system.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings. It is to be understood that other embodiments may be utilized, and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to sample processing systems, methods and devices for processing sample processing devices, and particularly, for detecting whether a material is present in a particular chamber of a sample processing device. More particularly, in some embodiments, the systems, methods and devices of the present disclosure can be used to detect whether a selected volume of a material is present in a particular chamber. In some cases, the sample processing device used to fluidically process and manipulate a sample can include various valving and metering elements. For example, a sample can be loaded on the sample processing device, various valves, channels, chambers, and or metering devices can be used to process and move the sample through various compartments of the sample processing device, ultimately ending in a process or detection chamber in which the sample will be assayed or interrogated (e.g., optically) to determine the absence, presence and/or amount of an analyte of interest in the sample. In order to ascertain whether a failure occurred in the fluidic processing of the sample on the sample processing device, it can be useful to know whether the sample was properly transferred to the process, or detection, chamber. As a result, the systems, methods and devices of the present disclosure are generally directed to determining whether a sample, or a selected volume of the sample, is present in the detection chamber.

In some embodiments of the present disclosure (e.g., described below with respect to the sample processing device 300 of FIGS. 16-22), a sample of interest (e.g., a raw sample, such as a raw patient sample, a raw environmental sample, etc.) can be loaded separately from various reagents or media that will be used in processing the sample for a particularly assay. In some embodiments, such reagents can be added as one single cocktail or "master mix" reagent that includes all of the reagents necessary for an assay of interest. The sample can be suspended or prepared in a diluent, and the diluent can include or be the same as the reagent for the assay of interest. The sample and diluent will be referred to herein as merely the "sample" for simplicity, and a sample combined with a diluent is generally still considered a raw sample, as no substantial processing, measuring, lysing, or the like, has yet been performed.

The sample can include a solid, a liquid, a semi-solid, a gelatinous material, and combinations thereof, such as a suspension of particles in a liquid. In some embodiments, the sample can be an aqueous liquid.

The sample processing device can then include means for moving the sample and reagents through the sample processing device and ultimately combining the sample and the reagents where and when necessary. In some embodiments, the reagents (e.g., the reagent master mix) can include one or more internal controls that can be used to validate that the reaction and the reagents are working. For example, one channel of a multiplex detection system can be used to detect the internal control and confirm that the reagents were transferred in the sample processing device properly and are working properly when no amplification is detected in the other channels of the multiplex detection system. That is, the internal control can be used to validate false negatives, and the lack of internal control amplification will invalidate the run. However, in a raw sample, there is no similar internal control. Therefore, if there is a failure on the sample manipulation and transfer (e.g., in the valving or metering devices), such that the sample never reached the detection chamber and was never combined with the reagent master mix, the internal control in the reagent master mix will still amplify, leading to a possible false negative determination. The sample processing systems, methods and devices of the present disclosure can be used to verify that the sample has moved to the detection chamber, and/or that a selected volume of the sample is present in the detection chamber. If such a verification is not found, this can be indicated, for example, by initiating an alert, by generating a failure report, by invalidating a run, by interrupting a run, etc., or a combination thereof.

The phrase "raw sample" is generally used to refer to a sample that has not undergone any processing or manipulation prior to being loaded onto the sample processing device, besides merely being diluted or suspended in a diluents. That is, a raw sample may include cells, debris, inhibitors, etc. and has not been previously lysed, washed, buffered, or the like, prior to being loaded onto the sample processing device. A raw sample can also include a sample that is obtained directly from a source and transferred from one container to another without manipulation. The raw sample can also include a patient specimen in a variety of media, including, but not limited to, transport medium, cerebral spinal fluid, whole blood, plasma, serum, etc. For example, a nasal swab sample containing viral particles obtained from a patient may be transported and/or stored in a transport buffer or medium (which can contain antimicrobials) used to suspend and stabilize the particles before processing. A portion of the transport medium with the suspended particles can be considered the "sample." All of the "samples" used with the devices and systems of the present disclosure and discussed herein can be raw samples.

FIGS. 1-15 generally illustrate a sample processing system according to the present disclosure, including the features, elements, functions, and methods of operation of such a system, including components and features used for optical detection. Such a sample processing system can be used to process sample processing devices. Sample processing device can generally be consumable (e.g., disposable) and include various fluidics (i.e., microfluidics) capable of directing and manipulating samples of interest. The sample processing system can be used to detect various features of the sample and the sample processing device.

FIGS. 16-23 illustrate exemplary embodiments of sample processing devices (e.g., "disks") that can be used in accordance with the present disclosure and which can be employed in the sample processing systems of the present disclosure.

Figure 24:
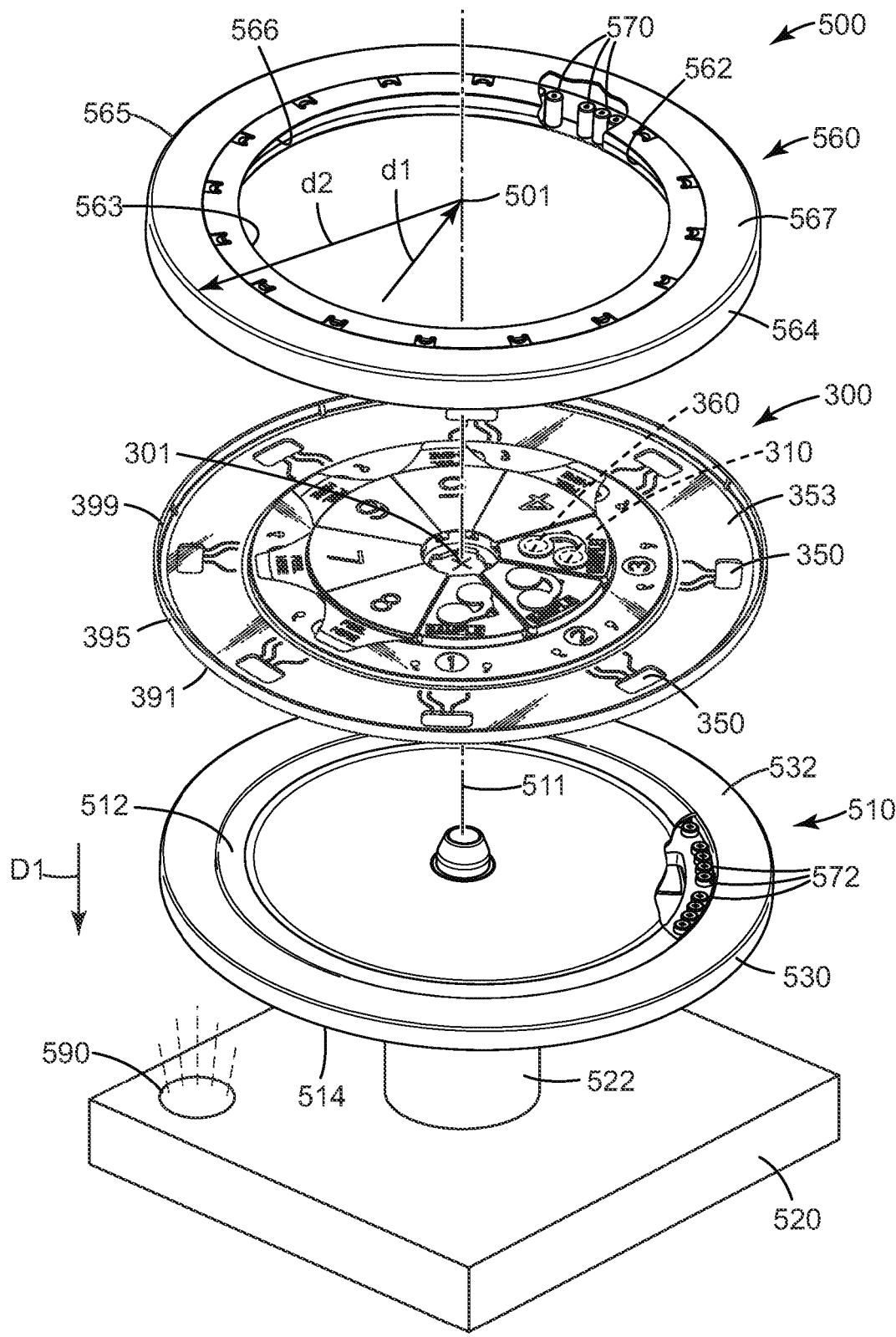
FIG. 24 is an exploded perspective view of a disk handling system according to one embodiment of the present disclosure.

FIG. 24 illustrates at least a portion of one exemplary disk handling system of the present disclosure that can form a portion of, or be used with, a sample processing system of the present disclosure. Particularly, FIG. 24 shows the interaction of an exemplary sample processing device (i.e., the sample processing device of FIGS. 16-22) with a cover and a base plate of the disk handling system. That is, FIG. 24 shows how a "disk" may physically (e.g., structurally, mechanically, and/or thermally) interact with various components of a sample processing system of the present disclosure.

It should be understood that while sample processing devices of the present disclosure are illustrated herein as being circular in shape and are sometimes referred to herein as "disks," a variety of other shapes and configurations of the sample processing devices of the present disclosure are possible, and the present disclosure is not limited to circular sample processing devices. As a result, the term "disk" is often used herein in place of "sample processing device" for brevity and simplicity, but this term is not intended to be limiting.

Sample Processing Systems

The sample processing systems of the present disclosure can be used in methods that involve thermal processing, e.g., sensitive chemical processes such as polymerase chain reaction (PCR) amplification, transcription-mediated amplification (TMA), nucleic acid sequence-based amplification (NASBA), ligase chain reaction (LCR), self-sustaining sequence replication, enzyme kinetic studies, homogeneous ligand binding assays, immunoassays, such as enzyme linked immunosorbent assay (ELISA), and more complex biochemical or other processes that require precise thermal control and/or rapid thermal variations. The sample processing systems are capable of providing simultaneous rotation of a sample processing device in addition to effecting control over the temperature of sample materials in process chambers on the devices.

Some examples of suitable construction techniques or materials that may be adapted for use in connection with the present invention may be described in, e.g., commonly-assigned U.S. Pat. Nos. 6,734,401, 6,987,253, 7,435,933, 7,164,107 and 7,435,933, entitled ENHANCED SAMPLE PROCESSING DEVICES SYSTEMS AND METHODS (Bedingham et al.); U.S. Pat. No. 6,720,187, entitled MULTI-FORMAT SAMPLE PROCESSING DEVICES (Bedingham et al.); U.S. Patent Publication No. 2004/0179974, entitled MULTI-FORMAT SAMPLE PROCESSING DEVICES AND SYSTEMS (Bedingham et al.); U.S. Pat. No. 6,889,468, entitled MODULAR SYSTEMS AND METHODS FOR USING SAMPLE PROCESSING DEVICES (Bedingham et al.); U.S. Pat. No. 7,569,186, entitled SYSTEMS FOR USING SAMPLE PROCESSING DEVICES (Bedingham et al.); U.S. Patent Publication No. 2009/0263280, entitled THERMAL STRUCTURE FOR SAMPLE PROCESSING SYSTEM (Bedingham et al.); U.S. Pat. No. 7,322,254 and U.S. Patent Publication No. 2010/0167304, entitled VARIABLE VALVE APPARATUS AND METHOD (Bedingham et al.); U.S. Pat. No. 7,837,947 and U.S. Patent Publication No. 2011/0027904, entitled SAMPLE MIXING ON A MICROFLUIDIC DEVICE (Bedingham et al.); U.S. Pat. Nos. 7,192,560 and 7,871,827 and U.S. Patent Publication No. 2007/0160504, entitled METHODS AND DEVICES FOR REMOVAL OF ORGANIC MOLECULES FROM BIOLOGICAL MIXTURES USING ANION EXCHANGE (Parthasarathy et al.); U.S. Patent Publication No. 2005/0142663, entitled METHODS FOR NUCLEIC ACID ISOLATION AND KITS USING A MICROFLUIDIC DEVICE AND CONCENTRATION STEP (Parthasarathy et al.); U.S. Pat. No. 7,754,474 and U.S. Patent Publication No. 2010/0240124, entitled SAMPLE PROCESSING DEVICE COMPRESSION SYSTEMS AND METHODS (Aysta et al.); U.S. Pat. No. 7,763,210 and U.S. Patent Publication No. 2010/0266456, entitled COMPLIANT MICROFLUIDIC SAMPLE PROCESSING DISKS (Bedingham et al.); U.S. Pat. Nos. 7,323,660 and 7,767,937, entitled MODULAR SAMPLE PROCESSING APPARATUS KITS AND MODULES (Bedingham et al.); U.S. Pat. No. 7,709,249, entitled MULTIPLEX FLUORESCENCE DETECTION DEVICE HAVING FIBER BUNDLE COUPLING MULTIPLE OPTICAL MODULES TO A COMMON DETECTOR (Bedingham et al.); U.S. Pat. No. 7,507,575, entitled MULTIPLEX FLUORESCENCE DETECTION DEVICE HAVING REMOVABLE OPTICAL MODULES (Bedingham et al.); U.S. Pat. Nos. 7,527,763 and 7,867,767, entitled VALVE CONTROL SYSTEM FOR A ROTATING MULTIPLEX FLUORESCENCE DETECTION DEVICE (Bedingham et al.); U.S. Patent Publication No. 2007/0009382, entitled HEATING ELEMENT FOR A ROTATING MULTIPLEX FLUORESCENCE DETECTION DEVICE (Bedingham et al.); U.S. Patent Publication No. 2010/0129878, entitled METHODS FOR NUCLEIC AMPLIFICATION (Parthasarathy et al.); U.S. Patent Publication No. 2008/0149190, entitled THERMAL TRANSFER METHODS AND STRUCTURES FOR MICROFLUIDIC SYSTEMS (Bedingham et al.); U.S. Patent Publication No. 2008/0152546, entitled ENHANCED SAMPLE PROCESSING DEVICES, SYSTEMS AND METHODS (Bedingham et al.); U.S. Patent Application Publication No. 2011/0117607, entitled ANNULAR COMPRESSION SYSTEMS AND METHODS FOR SAMPLE PROCESSING DEVICES (Bedingham et al.); U.S. Patent Application Publication No. 2011/0117656, entitled SYSTEMS AND METHODS FOR PROCESSING SAMPLE PROCESSING DEVICES (Robole et al.); U.S. Provisional Patent Application Ser. No. 60/237,151 filed on Oct. 2, 2000 and entitled SAMPLE PROCESSING DEVICES, SYSTEMS AND METHODS (Bedingham et al.); U.S. Pat. Nos. D638,550 and D638,951, entitled SAMPLE PROCESSING DISC COVER (Bedingham et al.); U.S. patent application Ser. No. 29/384,821, entitled SAMPLE PROCESSING DISC COVER (Bedingham et al.), filed Feb. 4, 2011; and U.S. Pat. No. D564,667, entitled ROTATABLE SAMPLE PROCESSING DISK (Bedingham et al.). The entire content of these disclosures are incorporated herein by reference.

Other potential device constructions may be found in, e.g., U.S. Pat. No. 6,627,159, entitled CENTRIFUGAL FILLING OF SAMPLE PROCESSING DEVICES (Bedingham et al.); U.S. Pat. Nos. 7,026,168, 7,855,083 and 7,678,334, and U.S. Patent Publication Nos. 2006/0228811 and 2011/0053785, entitled SAMPLE PROCESSING DEVICES (Bedingham et al.); U.S. Pat. Nos. 6,814,935 and 7,445,752, entitled SAMPLE PROCESSING DEVICES AND CARRIERS (Harms et al.); and U.S. Pat. No. 7,595,200, entitled SAMPLE PROCESSING DEVICES AND CARRIERS (Bedingham et al.). The entire content of these disclosures are incorporated herein by reference.

A sample processing system that is capable of multiplex fluorescence detection, including various features, elements and the operation of such a system, will now be described.

FIG. 1 is a schematic diagram illustrating an exemplary embodiment of a multiplex fluorescence detection device 10, a data acquisition device 21, and a disk handling system 500 that can employed as part of a sample processing system 12. The disk handling system 500 will be described in greater detail below with reference to FIG. 24. Detection device 10 can be used to detect various characteristics of a sample, including whether a sample, or a selected volume of a sample, is present in a detection chamber of a sample processing device (e.g., a rotating disk 13). In some embodiments, the sample processing device can be consumable and replaceable and may not necessarily be considered to form a portion of the sample processing system 12, but rather can be used with, or processed by, the sample processing system 12.

In the illustrated example, device 10 has four optical modules 16 that provide four "channels" for optical detection of four different dyes. In particular, device 10 has four optical modules 16 that excite different regions of rotating disk 13 at any given time, and collect emitted fluorescent light energy at different wavelengths from the dyes. As a result, modules 16 may be used to interrogate multiple, parallel reactions occurring within sample 22, and/or to determine whether sample 22, or a selected volume of sample 22, is located in a desired region (e.g., within a particular chamber) of the disk 13.

The multiple reactions may, for example, occur simultaneously within a single chamber of a rotating disk 13. Each of optical modules 16 interrogates sample 22 and collects fluorescent light energy at different wavelengths as the disk 13 rotates. For example, excitation sources within modules 16 may be sequentially activated for periods sufficient to collect data at the corresponding wavelengths. That is, a first optical module 16 may be activated for a period of time to collect data at a first range of wavelengths selected for a first dye corresponding to a first reaction. The excitation source may then be deactivated, and an excitation source within a second optical module 16 may be activated to interrogate sample 22 at a second range of wavelengths selected for a second dye corresponding to a second reaction. This process can continue until data has been captured from all optical modules 16. In one embodiment, each of the excitation sources within optical modules 16 is activated for an initial period of approximately 0.5 seconds to reach steady state followed by an interrogation period which lasts for 10-50 rotations of disk 13. In other embodiments, the excitation sources may be sequenced for shorter (e.g., 1 or 2 milliseconds) or longer periods. In some embodiments, more than one optical module may be activated simultaneously for concurrent interrogation of sample 22 without stopping the rotation of disk 13.

Although a single sample 22 is illustrated, disk 13 may contain a plurality of chambers holding samples. Optical modules 16 may interrogate some or all of the different chambers at different wavelengths. In one embodiment, disk 13 includes 96 chambers space around a circumference of disk 13. With a 96 chamber disk and four optical modules 16, device 10 may be capable of acquiring data from 384 different species.

In one embodiment, optical modules 16 include excitation sources that are inexpensive high power light emitting diodes (LEDs), which are commercially available in a variety of wavelengths and have long lifetimes (e.g., 100,000 hours or more). In another embodiment, conventional halogen bulbs or mercury lamps may be used as excitation sources.

As illustrated in FIG. 1, each of optical modules 16 may be coupled to one leg of a fiber optic bundle 14. Fiber optic bundle 14 provides a flexible mechanism for collection of fluorescent signals from optical modules 16 without loss of sensitivity. In general, a fiber optic bundle comprises multiple optical fibers laid side by side and bonded together at the ends and encased in a flexible protective jacket. Alternatively, fiber optic bundle 14 may comprise a smaller number of discrete, large diameter multi-mode fibers, either glass or plastic, having a common end. For example, for a four-optical module device, fiber optic bundle 16 may comprise four discrete multimode fibers, each having a 1 mm core diameter. The common end of the bundle contains the four fibers bound together. In this example, the aperture of detector 18 may be 8 mm, which is more than sufficient for coupling to the four fibers.

In this example, fiber optic bundle 14 couples optical modules 16 to a single detector 18. The optical fibers carry the fluorescent light collected by optical modules 16 and effectively deliver the captured light to detector 18. In one embodiment, detector 18 is a photomultiplier tube. In another embodiment, the detector may include multiple photomultiplier elements, one for each optical fiber, within the single detector. In other embodiments, one or more solid-state detectors may be used.

The use of a single detector 18 may be advantageous in that it allows use of a highly sensitive and possibly expensive detector (e.g., a photomultiplier), while maintaining a minimal cost in that only a single detector need be used. A single detector is discussed herein; however, one or more detectors may be included for detecting a greater number of dyes. For example, four additional optical modules 16 and a second detector may be added to the system to allow for the detection of eight different wavelengths emitted from one disk. An exemplary fiber optic bundle coupled to a single detector for use with rotating disk 13 is described in U.S. Pat. No. 7,709,249 entitled "MULTIPLEX FLUORESCENCE DETECTION DEVICE HAVING FIBER BUNDLE COUPLING MULTIPLE OPTICAL MODULES TO A COMMON DETECTOR," filed on Jul. 5, 2005, the entire content of which is hereby incorporated by reference.

Optical modules 16 can be removable from the device and easily interchangeable with other optical modules that are optimized for interrogation at different wavelengths. For example, optical modules 16 may be physically mounted within locations of a module housing. Each of optical modules 16 may be easily inserted within a respective location of the housing along guides (e.g., recessed grooves) that mate with one or more markings (e.g., guide pins) of the optical module. Each of optical modules 16 may be secured within the carriage by a latch, magnet, screw or other fastening device. Each optical module includes an optical output port (shown in FIGS. 6 and 7) for coupling to one leg of fiber optic bundle 14. The optical output port may have a threaded end coupled to a threaded connector of the leg. Alternatively, a form of "quick-connect" may be used (e.g., a slidable connection having an o-ring and a catch pin) that allows fiber optic bundle 14 to be slidably engaged and disengaged from the optical output port. Moreover, each of optical modules 16 may have one or more electrical contacts pads or flex circuits for electronically coupling to control unit 23 when fully inserted. Exemplary removable optical modules for use with rotating disk 13 is described in U.S. Pat. No. 7,507,575 entitled "MULTIPLEX FLUORESCENCE DETECTION DEVICE HAVING REMOVABLE OPTICAL MODULES," filed on Jul. 5, 2005, the entire content of which is hereby incorporated by reference.

The modular architecture of device 10 allows the device to be easily adapted for all of the fluorescent dyes used in a given analysis environment, such as multiplex PCR. Other chemistries that may be used in device 10 include Invader (Third Wave, Madison, Wis.), Transcripted-mediated Amplification (GenProbe, San Diego, Calif.), fluorescence labeled enzyme linked immunosorbent assay (ELISA), and/or fluorescence in situ hybridization (FISH). The modular architecture of device 10 may provide another advantage in that the sensitivity of each optical module 16 can be optimized by choice of the corresponding excitation source (not shown) and excitation and detection filters for a small specific target range of wavelengths in order to selectively excite and detect a corresponding dye in the multiplex reaction.

For purpose of example, device 10 is illustrated in a 4-color multiplex arrangement, but more or less channels can be used with the appropriate fiber optic bundle 14. This modular design allows a user to easily upgrade device 10 in the field by simply adding another optical module 16 to device 10 and inserting one leg of fiber optic bundle 14 into the new optical module. Optical modules 16 may have integrated electronics that identify the optical modules and download calibration data into an internal control module or other internal electronics (e.g., control unit 23) of device 10.

In the example of FIG. 1, samples 22 are contained in chambers of disk 13, which is mounted on a rotating platform under the control of control unit 23 (one embodiment of a rotating platform is shown by way of example only in FIG. 24). A slot sensor trigger 27 provides an output signal utilized by control unit 23 for synchronizing data acquisition device 21 with chamber position during disk rotation. Slot sensor trigger 27 may be a mechanical, electrical, magnetic, or optical sensor. For example, as described in further detail below, slot sensor trigger 27 may include a light source that emits a beam of light through a slot formed through disk 13 that is detected each revolution of the disk. As another example, slot sensor trigger may sense reflected light for purposes of synchronizing the rotation of disk 13 and data acquisition by modules 16 and detector 18. In other embodiments, disk 13 may include a tab, protrusion or reflective surface in addition to or in place of the slot. Slot sensor trigger 27 may use any physical structure or mechanism to locate the radial position of disk 13 as it rotates. Optical modules 16 may be physically mounted above rotating platform 25, such that optical modules 16 are overlapped with different chambers at any one time.

Detection device 10 can also include a heating element (not shown in FIG. 1 but an exemplary heating element is shown in FIG. 24 and described below) for modulating the temperature of the sample 22 on disk 13. The heating element may comprise a cylindrical halogen bulb contained within a reflective enclosure. The reflective chamber is shaped to focus radiation from the bulb onto a radial section of disk 13. Generally, the heated area of disk 13 can comprise an annular ring as disk 13 spins. In this embodiment, the shape of the reflective enclosure may be a combination of elliptical and spherical geometries that allow precise focusing. In other embodiments, the reflective enclosure may be of a different shape or the bulb may broadly irradiate a larger area. In other embodiments, the reflective enclosure may be shaped to focus the radiation from the bulb onto a single area of the disk 13, such as a single process chamber containing a sample 22.

In some embodiments, the heating element may heat air and force the hot air over one or more samples to modulate the temperature. Additionally, the samples may be heated directly by the disk. In this case, the heating element may be located in platform 25 and thermally couple to disk 13. Electrical resistance within the heating element may heat a selected region of the disk as controlled by control unit 23. For example, a region may contain one or more chambers, possibly the entire disk. An exemplary heating element for use with rotating disk 13 is described in U.S. Patent Application Publication No. 2007/0009382, entitled "HEATING ELEMENT FOR A ROTATING MULTIPLEX FLUORESCENCE DETECTION DEVICE," filed on Jul. 5, 2005, the entire content of which is hereby incorporated by reference.

Alternatively, or in addition, device 10 may also include a cooling component (not shown). A fan can be included in device 10 to supply cold air, i.e., room temperature air, to disk 13. Cooling may be needed to modulate the temperature of the sample appropriately and store samples after an experiment has completed. In other embodiments, the cooling component may include thermal coupling between platform 25 and disk 13, as platform 25 may reduce its temperature when needed. For example, some biological samples may be stored at 4° C. to reduce enzyme activity or protein denaturing.

Detection device 10 may also be capable of controlling reaction species contained within a process chamber. For example, it may be beneficial to load some species in a process chamber to generate one reaction and later add another species to the sample once the first reaction has terminated. A valve control system may be utilized to control a valve separating an inner holding chamber from the process chamber, thereby controlling the addition of species to the chamber during rotation of disk 13. The valve control system may be located within or mounted to one of optical modules 16 or separate from the optical modules 16. Directly below the laser, under disk 13, may be a laser sensor for positioning the laser relative to disk 13.

In one embodiment, the valve control system includes a near infrared (NIR) laser capable of being driven at two or more power levels in combination with a sensor. Under a low power setting, the laser may be used for positioning disk 13 and targeting select valves, e.g., by the sensor sensing the NIR light emitted by the laser though a slot in disk 13. Once the targeted valve is rotated into position, control unit 23 can direct the laser to output a short burst of high power energy to heat the valve and open the targeted valve. The burst of energy forms a void in the valve, e.g., by piercing, melting or ablating, causing the valve to open and allowing a fluid to flow through a channel from an inner holding chamber to an outside process chamber. In some embodiments, disk 13 may contain a plurality of valves of various sizes and materials to generate a plurality of reactions in sequence. More than one set of valve control systems may be used when utilizing a disk having multiple chamber valves.

Data acquisition device 21 may collect data from device 10 for each dye either sequentially or in parallel. In one embodiment, data acquisition system 21 collects the data from optical modules 16 in sequence, and corrects the spatial overlap by a trigger delay for each one of the optical modules 16 measured from the output signal received from slot sensor trigger 27.

One application for device 10 is real-time PCR, but the techniques described herein may be extended to other platforms that utilize fluorescence detection at multiple wavelengths. Device 10 may combine rapid thermal cycling, utilizing the heating element, and centrifugally driven microfluidics for isolation, amplification, and detection of nucleic acids. By making use of multiplex fluorescence detection, multiple target species may be detected and analyzed in parallel.

For real-time PCR, fluorescence is used to measure the amount of amplification in one of three general techniques. The first technique is the use of a dye, such as Sybr Green (Molecular Probes, Eugene, Oreg.), whose fluorescence increases upon binding to double-stranded DNA. The second technique uses fluorescently labeled probes whose fluorescence changes when bound to the amplified target sequence (hybridization probes, hairpin probes, etc.). This technique is similar to using a double-stranded DNA binding dye, but is more specific because the probe will bind only to a certain section of the target sequence. The third technique is the use of hydrolysis probes (Taqman™, Applied BioSystems, Foster City Calif.), in which the exonuclease activity of the polymerase enzyme cleaves a quencher molecule from the probe during the extension phase of PCR, making it fluorescently active.

In each of the approaches, fluorescence is linearly proportional to the amplified target concentration. Data acquisition system 21 measures an output signal from detector 18 (or alternatively optionally sampled and communicated by control unit 23) during the PCR reaction to observe the amplification in near real-time. In multiplex PCR, the multiple targets are labeled with different dyes that are measured independently. Generally speaking, each dye will have different absorbance and emission spectra. For this reason, optical modules 16 may have excitation sources, lenses and related filters that are optically selected for interrogation of sample 22 at different wavelengths.

Figure 2:
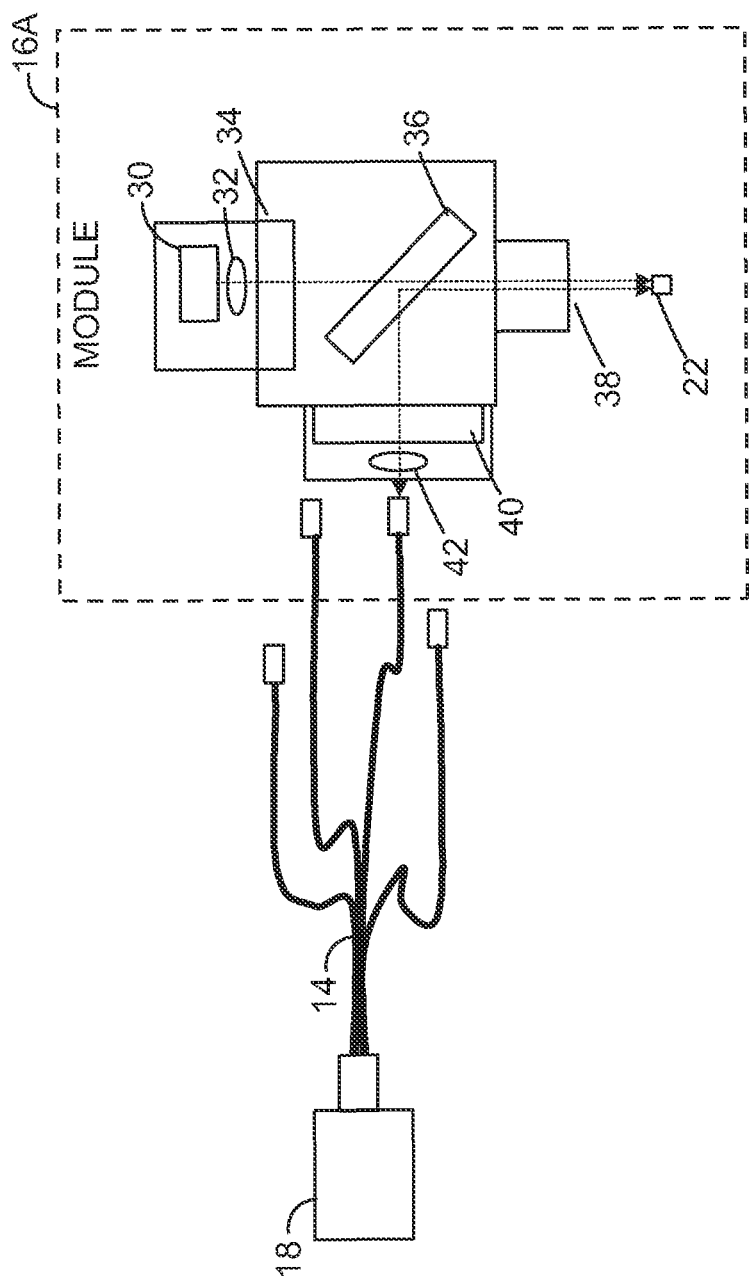
FIG. 2 is a schematic diagram illustrating an exemplary optical detection module, which may correspond to any of a plurality of optical modules of the multiplex fluorescence detection device of FIG. 1.

FIG. 2 is a schematic diagram illustrating an exemplary optical module 16A, which may correspond to any of optical modules 16 of FIG. 1. In this example, optical module 16A contains a high-power excitation source, LED 30, a collimating lens 32, an excitation filter 34, a dichroic filter 36, a focusing lens 38, a detection filter 40, and a lens 42 to focus the fluorescence into one leg of fiber optic bundle 14.

Consequently, the excitation light from LED 30 is collimated by collimating lens 32, filtered by excitation filter 34, transmitted through dichroic filter 36, and focused into the sample 22 by focusing lens 38. The resulting fluorescence emitted by the sample is collected by the same focusing lens 38, reflected off of dichroic filter 36, and filtered by detection filter 40 before being focused into one leg of fiber optic bundle 14. The optic bundle 14 then transfers the light to detector 18.

LED 30, collimating lens 32, excitation filter 34, dichroic filter 36, focusing lens 38, detection filter 40, and lens 42 are selected based on the specific absorption and emission bands of the multiplex dye with which optical module 16A is to be used. In this manner, multiple optical modules 16 may be configured and loaded within device 10 to target different dyes.

The following table lists exemplary components that may be used in a 4-channel multiplex fluorescence detection device 10 for a variety of fluorescent dyes. Examples of suitable dyes include, but are not limited to, a 5-carboxyfluorescein dye, i.e., a fluorescein derivative, available under the trade designation "FAM" from Applera, Norwalk, Calif.; a 6-carboxy-2',4,4',5',7,7'-hexachlorofluorescein dye, i.e., a fluorescein derivative, available under the trade designation "HEX" from Applera; a 6-carboxy-4',5'-dichloro-2',7'-dimethoxyfluorescein dye, i.e., a fluorescein derivative, available under the trade designation "JOE" from Applera; a fluorescein derivative dye, available under the trade designation "VIC" from Applera; a fluorescein derivative dye, available under the trade designation "TET" from Applera; a 6-carboxy-X-rhodamine dye, i.e., a rhodamine derivative, available under the trade designation "ROX" from Invitrogen, Carlsbad, Calif.; an intercalating dye, available under the trade designation "SYBR" from Invitrogen (referred to in the following table as "Sybr Green"); a rhodamine derivative dye available under the trade designation "TEXAS RED" from Invitrogen (referred to in the following table as "Tx Red"); a 5-N-N'-diethyltetramethylindodicarbocyanine dye, i.e., a cyanine derivative, available under the trade designation "CY5" from Amersham, Buckinghamshire, United Kingdom (referred to in the following table as "Cy5"); a phosphoramidite derivative dye available under the trade designation "CAL FLUOR RED 610" from Bio-Search Technologies, Novato, Calif. (referred to in the following table and the examples as "CFR610"); and an indocarbocyanine derivative dye, available under the trade designation "QUASAR 670" from BioSearch Technologies, Novato, Calif. (referred to in the following table as "Quasar 670").

| Optical Module | LED | Excitation Filter | Detection Filter | Dye |
|---|---|---|---|---|
| 1 | blue | 475 nm | 520 nm | FAM, Sybr Green |
| 2 | green | 530 nm | 555 nm | HEX, JOE, VIC, TET |
| 3 | orange | 580 nm | 610 nm | ROX, Tx Red, CFR610 |
| 4 | red | 630 nm | 670 nm | Cy 5, Quasar 670 |

One advantage of the described modular, multiplex detection architecture is the flexibility in optimizing detection for a wide variety of dyes and/or for determining whether a material, or a selected volume of material, is present in particular chambers of the disk 13. Conceivably a user may have a bank of several different optical modules 16 that can be plugged into device 10 as needed, of which N can used at any one time, where N is the maximum number of channels supported by the device. In addition, one or more of the optical channels of one or more of the optical modules 16 can be dedicated to sensing (e.g., optically interrogating) whether material, or a selected volume of material, is present in particular chambers of the disk 13. For example, in some embodiments, a FAM optical channel can be particularly suitable for detecting backscattered reflection of an electromagnetic signal that is directed at the disk 13, and in some embodiments, a CFR610 optical channel can be particularly suitable for detecting the presence of material, or a selected volume of material, in the detection chamber using fluorescence. Therefore, device 10 and optical modules 16 may be used with any fluorescent dye and PCR detection method. A larger fiber optic bundle may be used to support a larger number of detection channels. Moreover, multiple fiber optic bundles may be used with multiple detectors. For example, two 4-legged fiber optic bundles may be used with eight optical modules 16 and two detectors 18.

Figure 3:
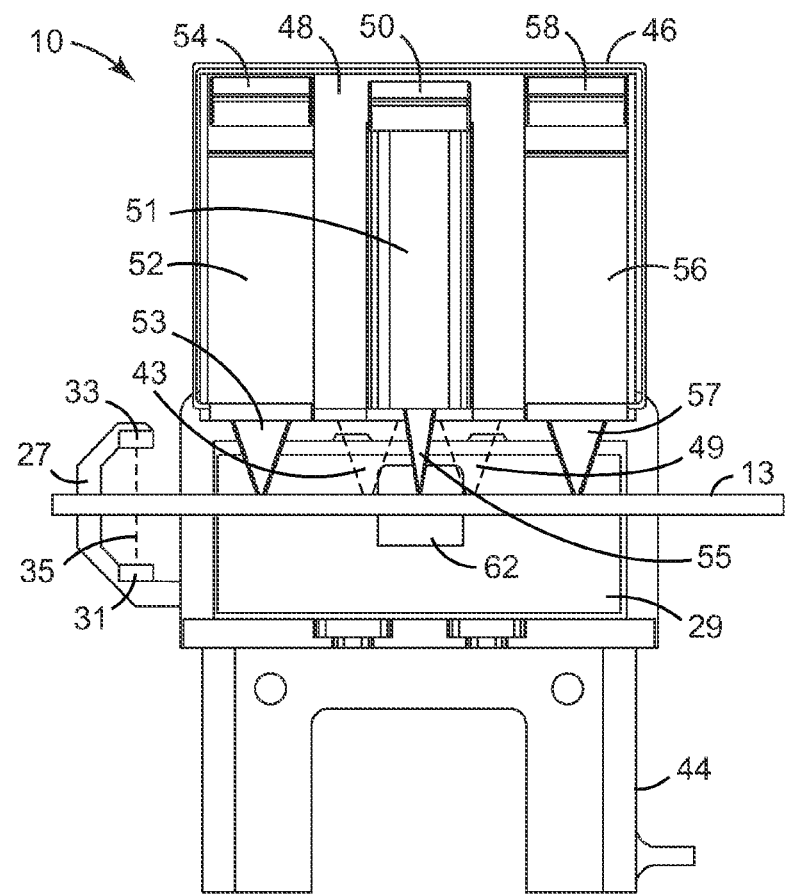
FIG. 3 is a front elevational view of a detection device according to one embodiment of the present disclosure, the detection device including a set of removable optical modules within a housing, including a main removable optical module and two supplementary removable optical modules.

FIG. 3 illustrates a front view of an exemplary set of removable optical modules within a housing. In the example of FIG. 3, device 10 includes base arm 44 and module housing 46. Main optical module 48, supplemental optical module 52 and supplemental optical module 56 are contained within module housing 46. Optical modules 48, 52 and 56 produce optical output beams 43, 49, 53 and 57, respectively, that sequentially excite different process chambers of disk 13. In other words, output beams 43, 49, 53 and 57 follow the curvature of disk 13 to each excite the same radial position of the disk which contains the process chambers. Optical module 48 contains two optical channels which each output different beams 43 and 49. As shown, slot sensor trigger 27 can include infrared light source 31 which produces light 35 that is detected by detector 33.

Each of optical modules 48, 52 and 56 can include a respective release lever 50, 54 or 58, respectively, for engaging module housing 46. Each release lever may provide an upward bias to engage a respective latch formed within module housing 46. A technician or other user can depress release levers 50, 54 or 58, respectively, in order to unlatch and remove optical module 48, 52 or 56 from module housing 46. Barcode reader 29 can include laser 62 for identifying disk 13.

Base arm 44 extends from detection device 10 and provides support for module housing 46 and optical modules 48, 52 and 56. Module housing 46 may be securely mounted atop base arm 44. Module housing 46 may contain a location adapted to receive a respective one of optical modules 48, 52 and 56. Although described for exemplary purposes with respect to module housing 46, module housing 46 of detection device 10 may have a plurality of locations for receiving optical modules 48, 52 and 56. In other words, a separate housing need not be used for optical modules 48, 52 and 56.

Each location of module housing 46 may contain one or more tracks or guides which help to correctly position the associated optical module within the location when a technician or other user inserts the optical module. These guides may be located along the top, bottom, or sides of each locations. Each of optical modules 48, 52 and 56 may include guides or tracks that mate with the guides or tracks of the locations of module housing 46. For example, module housing 46 may have protruding guides which mate with recessed guides in optical modules 48, 52 and 56.

In some embodiments, module housing 46 may not completely enclose each of optical modules 48, 52 and 56. For example, module housing 46 may provide mounting points to secure each of optical modules 48, 52 and 56 to base arm 44, but portions or all of each optical module may be exposed. In other embodiments, module housing 46 may completely enclose each of optical modules 48, 52 and 56. For example, module housing 46 may include a single door that closes over optical modules 48, 52 and 56, or a respective door for each of the modules. This embodiment may be appropriate for applications where the modules are seldom removed or detection device 10 is subjected to extreme environmental conditions.

A technician may easily remove any of optical modules 48, 52 or 56, and this may be completed by using only one hand. For example, the technician may rest his or her forefinger under a molded lip located beneath release lever 54 of optical module 52. The technician's thumb may then press down release lever 54 to release optical module 52 from module housing 46. While grasping optical module 52 between the thumb and forefinger, the technician may pull back on the optical module to remove the optical module from detection device 10. Other methods may be used to remove any of optical module 48, 52 or 56, including methods utilizing two-handed removal. Inserting any of optical module 48, 52 or 56 may be accomplished in a reversed manner with one or two hands.

In the example of FIG. 3, the components of two optical modules are combined to form main optical module 48. Main optical module 48 may contain light sources that produce two different wavelengths of light and detectors for detecting each different wavelength of fluorescence from the samples in disk 13. Therefore, main optical module 48 may connect to two legs of fiber optic bundle 14. In this manner, main optical module 48 may be viewed as a dual-channeled optical module having two independent optical excitation and collection channels. In some embodiments, main optical module 48 may contain optical components for more than two optical modules. In other cases, module housing 46 contains a plurality (e.g., two or more) of single-channeled optical modules, such as supplemental optical modules 52 and 56. In still other cases, module housing 46 contains a combination of one or more dual-channeled optical modules 48 and one or more single-channeled optical modules 52, 56.

As illustrated in FIG. 3, main optical module 48 may also contain components for a laser valve control system 51 (located within optical module 48). Laser valve control system 51 detects disk 13 location by a small slot located near the outer edge of disk 13. A detector (not shown) detects low power laser light 55 to map the location of disk 13 with respect to the motor which spins the disk. The control unit 23 uses the map to locate valves (not shown in FIG. 3) on disk 13 and to rotate targeted valves in position for opening via laser valve control system 51.

Once a targeted valve is in position, laser valve control system 51 focuses laser light 55 on the valve using one or more short bursts of high power. The short bursts form a void in the targeted valve, e.g., by piercing, melting or ablating the valve, allowing contents of an inner holding chamber to flow to an outer process chamber as disk 13 rotates. Detection device 10 may then monitor the subsequent reaction in the process chamber and/or detect whether the contents, or a selected volume thereof, has effectively transferred to the process chamber. Contents within a chamber may include substances in a fluid or solid state.

In some embodiments, laser valve control system 51 may be contained within a single-channeled optical module, e.g., supplemental optical module 54 or supplemental optical module 56. In other embodiments, laser valve control system 51 may be mounted to detection device 10 separately from any of optical modules 48, 52 or 56. In this case, laser valve control system 51 may be removable and adapted to engage a location within module housing 46 or a different housing of detection device 10.

In the example of FIG. 3, slot sensor trigger 27 is located near the removable modules, on either side of disk 13. In one embodiment, slot sensor trigger 27 contains a light source 31 to emit infrared (IR) light 35. Detector 33 detects IR light 35 when the slot in disk 13 allows the light to pass through the disk to detector 33. Control unit 23 uses an output signal produced by detector 33 to synchronize data acquisition from optical modules 48, 54 and 56 with rotation of disk 13. In some embodiments, slot sensor trigger 27 may extend from base arm 44 to reach the outer edge of disk 13 during device 10 operation. In other embodiments, a mechanical detector may be used to detect the position of disk 13.

Barcode reader 29 uses laser 62 to read a barcode located on the side edge of disk 13. The barcode identifies the type of disk 13 to allow proper operation of device 10. In some embodiments, the barcode may identify the actual disk to assist a technician in tracking data to specific samples from multiple disks 13.

All surface components of optical modules 48, 52 and 56 may be constructed of a polymer, composite, or metal alloy. For example, high molecular weight polyurethane may be used in forming the surface components. In other cases, an aluminum alloy or carbon fiber structure may be created. In any case, the material may be resistant to heat, fatigue, stress, and corrosion. As detection device 10 may come into contact with biological materials, the structures may be sterilizable in the event chamber contents leak out of disk 13.

Figure 4:
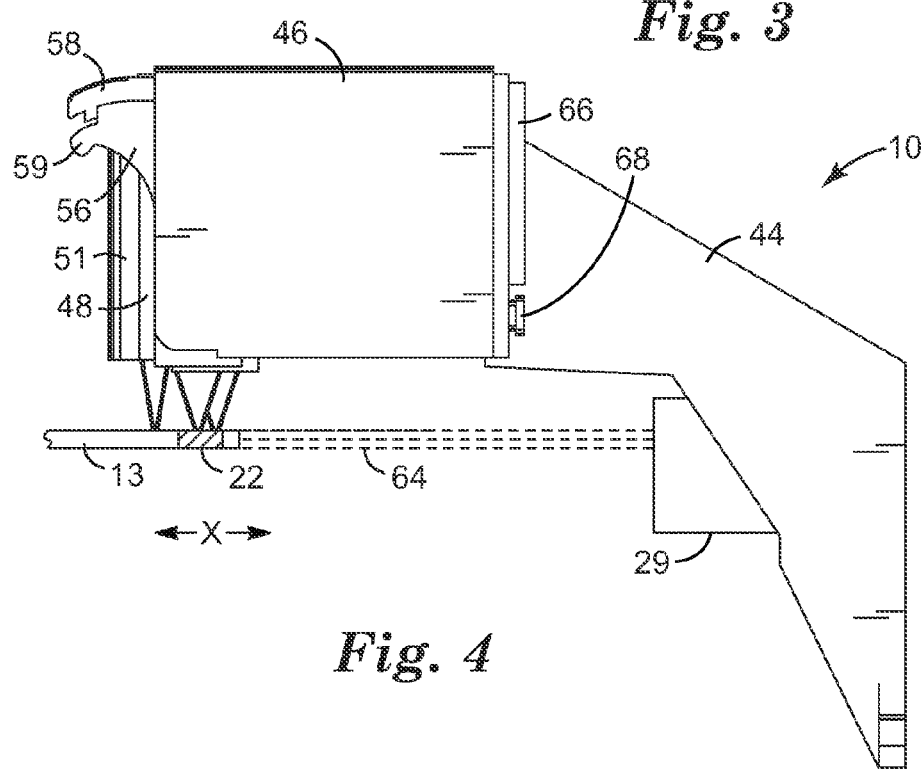
FIG. 4 is a side elevational view of the detection device of FIG. 3.

FIG. 4 illustrates a side view of the exemplary set of removable optical modules 48, 52 and 56 within module housing 46 of detection device 10. In the example of FIG. 4, base arm 44 supports barcode reader 29 as well as the removable optical modules 48, 52 and 56 attached within module housing 46. Disk 13 is located beneath optical modules 48, 52 and 56 with the samples 22 located under a respective optical path of each of the modules at different moments in time.

Within module housing 46, the fronts of supplementary module 56 and main optical module 48 can be seen. Supplementary module 56 contains molded lip 59 and release lever 58. As previously described, molded lip 59 may be used to grasp module 56 when removing or inserting the module into module housing 46. All of optical modules 48, 52 and 56 may have a respective molded lip and release lever, or a single release lever may be used to remove all of the optical modules. In some embodiments, optical modules 48, 52 and 56 may contain a different component for grasping the module. For example, each of optical modules 48, 52 and 56 may contain a handle for removing the respective module in a vertical or horizontal direction from module housing 46.

The location of optical modules 48, 52 and 56 within module housing 46 may be fixed in order to separately excite different samples within disk 13 at any particular moment in time. For example, main optical module 48 may be located slightly further toward base arm 44 than supplemental optical modules 52 and 56, which are offset to a location at either side of the main module. Moreover, optical modules 48, 52 and 56 may be offset in a horizontal direction (indicated by the arrow in FIG. 4, where X is the distance the outside light beams are offset from the inside light beams) so that the excitation light beams produced by the modules follows the curvature of disk 13. In this arrangement, the light beams produced by optical modules 48, 52 and 56 traverse the same path as disk 13 rotates, thereby exciting and collecting light from process chambers located along the path. In some embodiments, optical modules 48, 52 and 56 can be aligned such that the excitation light beams traverse different paths around rotating disk 13. In some embodiments, optical modules 48, 52 and 56 can be aligned such that the excitation light beams traverse different paths around rotating disk 13, same paths, or a combination thereof.

In this example, base arm 44 contains electrical contact board 66 which extends into module housing 46. Inside module housing 46, electrical contact board 66 may contain electrical contacts for each of optical modules 48, 52 and 56. Electrical contact board 66 may be electrically coupled to control unit 23. In some embodiments, each of optical modules 48, 52 and 56 may have a separate associated electrical contact board which is connected to control unit 23. In some embodiments, at least a portion of the control unit 23 and the data acquisition device 21 can be located externally of the device 10 of FIGS. 3-8. In some embodiments, at least a portion of the control unit 23 may be located within one or more of the optical modules 48, 52 and 56.

Fiber optic coupler 68 couples one leg of the fiber optic bundle 14 to an optical output port of optical module 56. Although not shown, each of optical modules 48, 52 and 56 include an optical output port adapted to engage a respective fiber optic coupler mounted to module housing 46. The connection between fiber optic coupler 68 and the leg of fiber optic bundle 14 may be a threaded screw lock, snap closure or friction fit.

Barcode reader 29 produces laser light 64 for reading the barcode of disk 13. The laser light 64 follows a direct path where it interacts with the outer edge of disk 13. The light 64 may spread out to cover a large area of disk 13 at one time. In some embodiments, barcode reader 29 can read the barcode on disk 13 when the disk is rotating at slow speeds. In other embodiments, barcode reader 29 can read the barcode periodically during operation to make sure a new disk has not been loaded in device 10. The barcode reader 29 may detect more than one barcode on disk 13 in other embodiments.

In some embodiments, base arm 44 may be movable with respect to disk 13, for example on a gantry system between various gantry positions. In this case, base arm 44 could be configurable to detect samples on different sized disks or samples located within an interior of disk 13. For example, a larger disk containing more process chambers or larger process chambers may be used by moving the base arm 44 further away from the center of disk 13. Module housing 46 may also have a configurable position for each of optical module 48, 52 or 56 so that each module may be movable to one or more circular paths of process chambers around disk 13. In some embodiments, base arm 44 can be movable radially inwardly and radially outwardly relative to a center of disk 13, and the gantry positions can generally be referred to as "radial gantry positions" or "radial positions."

Figure 5:
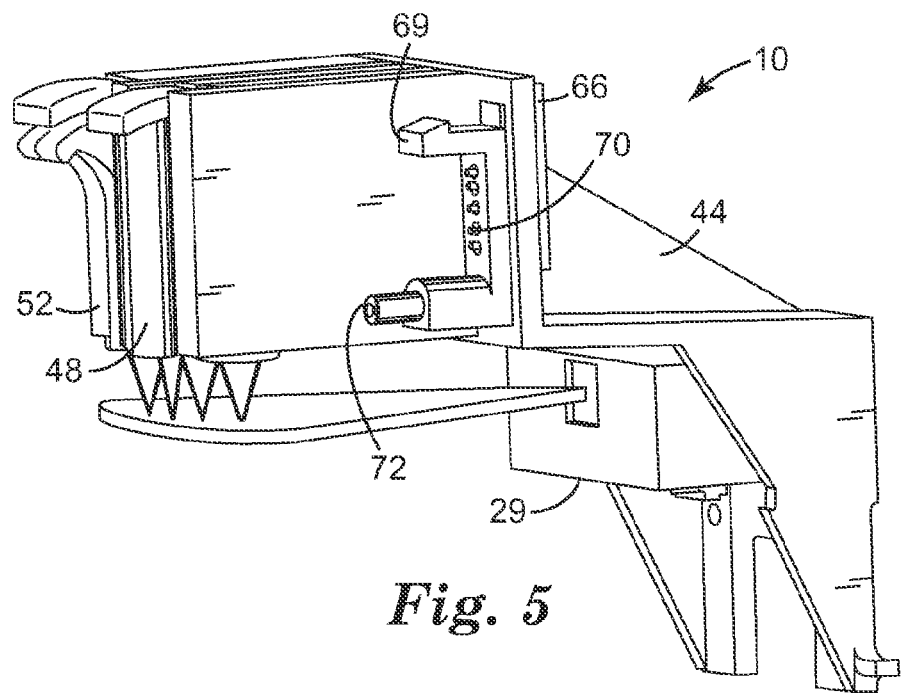
FIG. 5 is perspective view of the detection device of FIGS. 3-4, with one optical module removed to expose a module connector.

FIG. 5 shows the device 10 with one module removed to expose a module connector. In particular, module housing 46 is not shown in FIG. 5, and optical module 56 has been removed to expose optical modules 52 and 48 along with the connections for removed module 56.

Release lever 58 (FIG. 3) of optical module 56 securely attaches to attachment post 69 mounted to base arm 44. In this example, attachment post 69 extends into optical module 56 and couples to release lever 58. In other embodiments, other attachment mechanisms may be used to fix optical module 56 to base arm 44, such as a screw or snap fixation device.

Base arm 44 provides two different operational connections within module housing 46 for receiving and engaging optical module 56, once inserted. In particular, base arm 44 provides electrical contact board 66, which includes electrical connections 70 for coupling to the electrical contacts (not shown) contained within optical module 56. Electrical connections 70 allow control unit 23 to communicate with electrical components within module 56. For example, module 56 may include electrical circuits, hardware, firmware, or any combination thereof. In one example, the internal electrical components may store and output to control unit 23 unique identification information, such as a serial number. Alternatively, or in addition, the electrical components may provide information describing the specific characteristics of the optical components contained within the removable module 56. For example, the electrical components may include programmable read-only memory (PROM), flash memory, or other internal or removable storage media. Other embodiments may include a set of resistors, a circuit or an imbedded processor for outputting a unique signature of optical modules 48, 52 or 56 to control unit 23. In another example, optical module 56 may include a laser source and other components that form part of a laser valve control system, i.e. laser valve control system 51.

Electrical contact board 66 may be removed and replaced with another version associated with a different removable optical module. This option may support upgrades in device capability. In other embodiments, connections 70 may contain more or less connection pins.

In addition, base arm 44 and module housing 46 provide optical channel 72 within the location for receiving optical module 56. Optical channel 72 is connected to fiber optic coupler 68 (FIG. 4) that interfaces with a leg of fiber optic bundle 14. Optical channel 72 inserts into a location within optical module 56. The light captured by optical module 56 may be directed through optical channel 72, fiber optic coupler 68 and fiber optic bundle 15 to the detector 18. Fittings between these connections may be tight to ensure that light does not escape or enter the optical path.

In some embodiments, the connections to optical module 56 may be arranged in a different configuration. For example, the connections may be located in another position for accepting optical module 56 from another direction. In other embodiments, electrical connections may be located on one side of optical module 56 while an optical connection is located on a second surface of module 56. In any case, the electrical and optical connections located within the location of module housing 46 accommodate a removable optical module, i.e., optical module 56 in this example.

The optical and electrical connections of module 56 described in FIG. 5 may be used with any module, including optical modules 48 and 52. In addition, the connections for each optical module may not be identical. Since connections may be modified for coupling with a desired removable optical module, the connections utilized by any particular optical module inserted within a particular location of module housing 46 may vary at any time.

Figure 6:
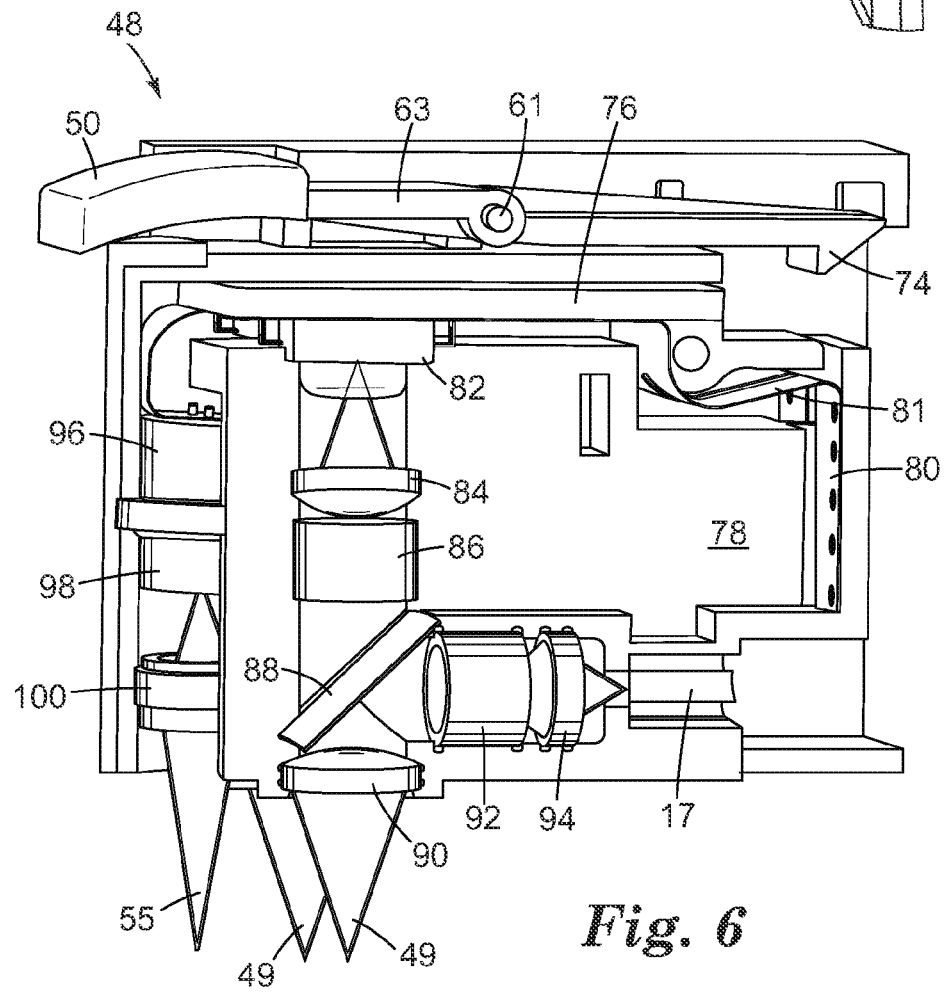
FIG. 6 is perspective view of internal components of an exemplary main removable optical module of the detection device of FIGS. 3-5.

FIG. 6 shows the internal components of the exemplary main removable optical module 48. In the example of FIG. 6, main optical module 48 includes release lever 50, pivot pin 61 and latch 74. Internal housing 78 separates each side of module 48 and contains electrical contacts pad 80 connected to ribbon 81. Optical components include LED 82, collimating lens 84, excitation filter 86, dichroic filter 88, focusing lens 90, detection filter 92 and lens 94. Optical output port 17 couples to a leg of fiber optic bundle 14. A separate set of optical components for a second optical channel (not shown) are located on the other side of internal housing 78. In addition, main module 48 includes connector 96, laser diode 98 and focusing lens 100 as part of a laser valve control system 51 controlled by control unit 23.

Release lever 50 is attached to optical module 48 by a pivot pin 61. Pivot pin 61 allows release lever 50 to rotate about the axis of the pin 61. When release lever 50 is depressed, arm 63 rotates counter-clockwise about the axis of the pin 61 to raise latch 74. Once latch 74 is raised, optical module 48 may be free for removal from module housing 46. There may be a spring or other mechanism maintaining a bias force against release lever 50 to maintain latch 74 in a down position. In some embodiments, a spring may be included around pivot pin 61 to provide a moment arm that keeps latch 74 in the down, or latched, position. In other embodiments, other mounting mechanisms may be added to or used in place of the described lever. For example, optical module 48 may be attached to module housing 46 by one or more screws or pins.

Mounting board 76 may be installed within optical module 48 for attaching communication ribbon 81 and LED 82. Ribbon 81 is connected to electrical contacts pad 80 and provides a connection between the pad and electrical components within optical module 48. Contacts pad 80 and ribbon 81 may carry the information required for both sides of main optical module 48, including laser valve control system 51 and any internal memory or other storage medium. Ribbon 81 may be flexible for weaving within optical module 48. Ribbon 81 may contain a plurality of electrically conductive wires to communicate signals between the electrical components and control unit 23 and/or to deliver power to the electrical components. In some embodiments, each electrical component may have a separate cable connecting the component with control unit 23. A technician may need to disconnect a cable or flex circuit from module housing 46 when removing optical module 48 from the housing.

In some embodiments, optical module 48 may contain a detector for detecting light from disk 13 and electronics for processing and storing the data. The electronics may contain a telemetry circuit for wirelessly transmitting data representing the detected light to control unit 23. Wireless communication may be performed by infrared light, radio frequency, Bluetooth, or other telemetry technique. Optical module 48 may also include a battery to power the electronics, which may, for example, be rechargeable by control unit 23.

LED 82 is affixed to mounting board 76 and electrically coupled to ribbon 81. LED 82 produces excitation light 49 of a predetermined wavelength to excite the sample 22. Excitation light 43 is produced by the second optical channel (not shown). After light 49 leaves LED 82, the light is expanded by collimating lens 84 before the light enters excitation filter 86. The light 49 of one wavelength band is passed by dichroic filter 88 and is focused on a sample by focusing lens 90. The light 49 excites the sample and fluorescence is collected by focusing lens 90 and delivered to detection filter 92 by dichroic filter 88. The resulting wavelength band of light is collected by lens 94 and delivered to optical output port 17 where the collected fluorescent light enters a leg of fiber optic bundle 14 for conveyance to detector 18. Such fluorescence can be indicative of the presence of an analyte of interest (e.g., as a result of the assay at hand), and/or such fluorescence can be indicative of the presence of a selected volume of material, for example, by optically interrogating a particular position (e.g., radial position) of the chamber to see if material is present at that particular location or height in the chamber. When the chamber is optically interrogated, the chamber is interrogated for an optical property of the material of interest to determine whether that material is present in the chamber. Such an optical property can include a variety of properties, including, but not limited to, absorption, fluorescence, backward Rayleigh scattering, backward scattered reflectance of an emitted electromagnetic signal, etc., or combinations thereof.

A "signal" can be created by interrogating for any of the above optical properties, and the signal can be an increase and/or decrease from a baseline. By way of example, the signal can come from the following modes:
 (i) Backscattering (or reflection)—Backscattering can be from detecting a meniscus in a liquid by the change in refractive index, from detecting particulates in the material being detected, from reflection from the backside of a chamber on the disk 13 that is being interrogated, or a combination thereof.

(ii) Fluorescence—by detecting fluorescence of the material detected or quenching of a background fluorescence (e.g., if a fluorophore is positioned in or on a surface forming the bottom of the detection chamber, such as by being incorporated into an adhesive, coating, or the like).

Both of these modes of detection, backscattering and fluorescence, can be impacted by refractive index differences between the material being detected and the air in the chamber and potentially the materials in the disk 13. The resulting refraction can either enhance or diminish signal. In some embodiments, a structured surface can be positioned on a surface forming the bottom or top of the chamber of interest to aid in focusing light or dispersing light. For example, a structured material with the same refractive index of the material being detected (=~1) could reflect light out of the detection path when dry, and allow straight path reflection when wet, i.e., in contact with the material to be detected.

In addition, both of these modes of detection can be impacted by absorbance of signal by the material being detected, and/or by a component of the disk 13. In some embodiments, the signal can be modulated by positioning a chromophore in or on a surface forming the bottom of the chamber (e.g., incorporated into an adhesive, coating, or the like). Alternatively, or additionally, in some embodiments, the signal can be modulated by adding a chromophore to the material being detected, either before or after that material is loaded onto the disk 13.

Light 49 can be backscattered by disk 13, or a portion thereof, such as a chamber on the disk 13 or a sample 22 positioned within a chamber on the disk 13, without necessarily exciting the sample and causing fluorescence. For example, an electromagnetic signal (e.g., light 49) can be emitted into the detection chamber, and a scan can be obtained by detecting backscattered reflection of the electromagnetic signal from the detection chamber. Such backscattered reflection can be collected and detected similarly as fluorescence would be. That is, the backscattered light can be collected by lens 94 and delivered to optical output port 17 where the collected backscattered light enters a leg of fiber optic bundle 14 for conveyance to detector 18. By way of example only, delivering and collecting backscattered light from disk 13 can be one way of determining (e.g., by optically interrogating) whether a sample, or a selected volume of a sample, is present in a particular chamber on disk 13. If calibrated, the backscattered electromagnetic signal can be used to quantify the amount of material in the chamber.

Internal housing 78 may support all components included in the excitation of the sample and detection of fluorescent light emitted by the sample for a selected wavelength. On the other side of internal housing 78, a similar configuration of optical components may be included to produce light of a different wavelength and detect the corresponding different fluorescent wavelength. Separation of each side may eliminate light contamination from one side entering the optical channel of the other side.

Housed partially between each side of module 48 may be the components of laser valve control system 51, including connector 96, laser diode 98 and focusing lens 100. Internal housing 78 may provide physical support for these components. Ribbon 81 is connected to connector 96 for communicating drive signals and power to the laser source. Laser diode 98 is connected to connector 96 and produces the laser energy 55 used to open valves on disk 13. Laser diode 98 can deliver this near-infrared (NIR) light to focusing lens 100 for directing the laser energy 55 to specific valves on disk 13. An NIR sensor may be located below disk 13 for locating particular valves that need to be opened. In other embodiments, these components may be housed separately from the optical components.

In some embodiments, emission lens 98 and focusing lens 100 of laser valve control system 51 may be contained within a single-channeled optical module, such as supplemental optical module 52 and 56 (FIG. 3).

Figure 7:
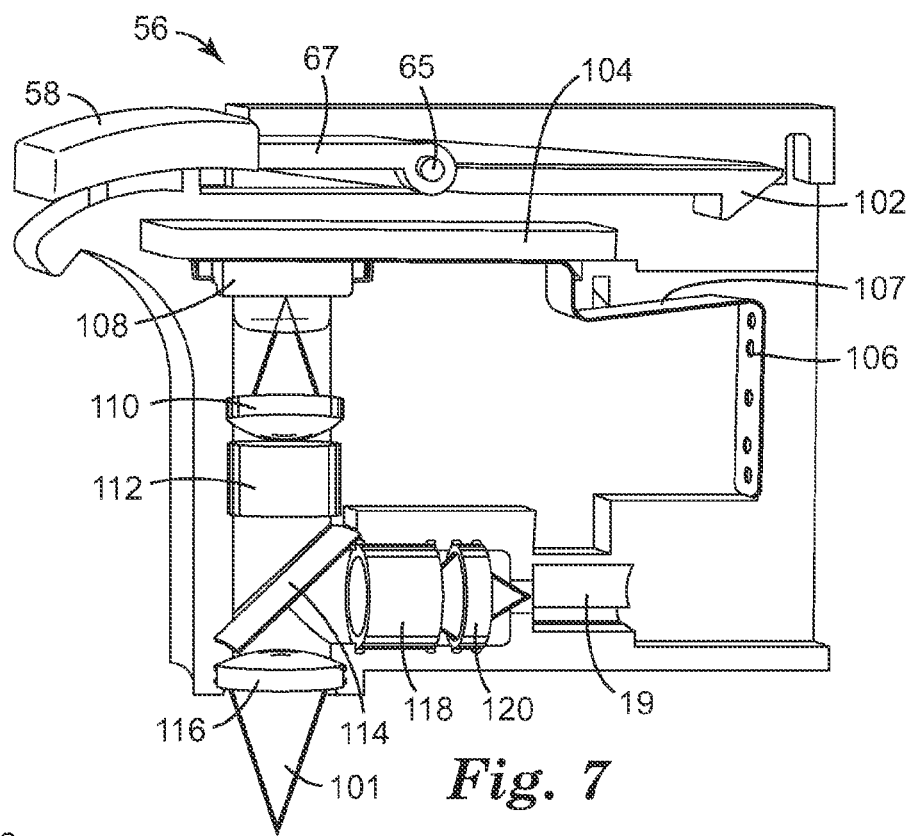
FIG. 7 is a perspective view of internal components of an exemplary supplemental removable optical module of the detection device of FIGS. 3-5.

FIG. 7 shows the internal components of an exemplary supplemental optical module that may be easily removed from or inserted into detection device 10. In the example of FIG. 7, optical module 56 includes release lever 58, pivot pin 59 and latch 102, similar to main optical module 48. Optical module 56 also includes electrical contacts pad 106 connected to ribbon 107. Ribbon 107 may also be connected to mounting board 104. Similar to main optical module 48, optical components include LED 108, collimating lens 110, excitation filter 112, dichroic filter 114, focusing lens 116, detection filter 118 and lens 120. Optical output port 19 couples to a leg of fiber optic bundle 14. Release lever 58 and latch 102 can operate substantially the same as that of the optical module 48 shown in FIG. 6 and described above.

Mounting board 104 may be installed within optical module 56 for attaching communication ribbon 107 and LED 108. Ribbon 107 is connected to electrical contacts pad 106 and provides a connection between the pad and electrical components within optical module 56. Contacts pad 106 and ribbon 107 may carry the information required for operating the optical components. Ribbon 107 may be flexible for weaving within optical module 56. Ribbon 107 may contain a plurality of electrically conductive wires to communicate signals between the components and control unit 23 and/or deliver power to the electrical components. In some embodiments, each electrical component may have a separate cable connecting the component with control unit 23. A technician may need to disconnect a cable or flex circuit from module housing 46 when removing optical module 56 from the housing.

Similar to optical module 48 described above and shown in FIG. 6, in some embodiments, optical module 56 may contain a detector for detecting light from disk 13 and electronics for processing and storing the data. The electronics may contain a telemetry circuit for wirelessly transmitting data representing the detected light to control unit 23 using any of the wireless communication modes or technologies described above. Optical module 56 may also include a battery to power the electronics, which may, for example, be rechargeable by control unit 23.

LED 108 is affixed to mounting board 104 and electrically coupled to ribbon 107. LED 108 produces excitation light 101 of a predetermined wavelength to excite the sample 22. After light 101 leaves LED 108, the light is expanded by collimating lens 110 before the light enters excitation filter 112. The light 101 of one wavelength band is passed by dichroic filter 114 and is focused on a sample by focusing lens 116. The light 101 excites the sample and fluorescence is collected by focusing lens 116 and delivered to detection filter 118 by dichroic filter 114. The resulting wavelength band of light is collected by lens 120 and delivered to optical output port 19 where the collected fluorescent light enters a leg of fiber optic bundle 14 for conveyance to detector 18.

Similar to optical module 48, optical module 56 (and/or optical module 52) can also (or instead of optical module 48)

be used to deliver and detect backscattered light from disk 13, or a portion thereof, such as from a chamber on the disk 13 or a sample 22 positioned within a chamber on the disk 13, without necessarily exciting the sample and causing fluorescence. Such backscattered light can be collected and detected similarly as fluorescence would be. That is, the backscattered light can be collected by lens 120 and delivered to optical output port 19 where the collected backscattered light enters a leg of fiber optic bundle 14 for conveyance to detector 18. As with optical module 48, fluorescence and/or backscattered light can be means for determining whether a selected volume of material is present in a particular chamber of disk 13.

Supplemental optical module 56 may also contain the components of laser valve control system 51. Laser valve control system 51 may be the only system used within device 10 or one of a plurality of laser valve control systems. The components used for this system may be similar to the components described in optical module 48 of FIG. 6.

The components of supplemental optical module 56 may be similar to any supplemental optical module or any optical module used to emit and detect one wavelength band of light. In some embodiments, the components may be altered in configuration to accommodate different experimental applications. For example, any optical modules may be modified to be inserted from a different direction or to be placed within the device at a different position with respect to disk 13. In any case, the optical modules may be removable to provide modification flexibility to device 10.

Figure 8:
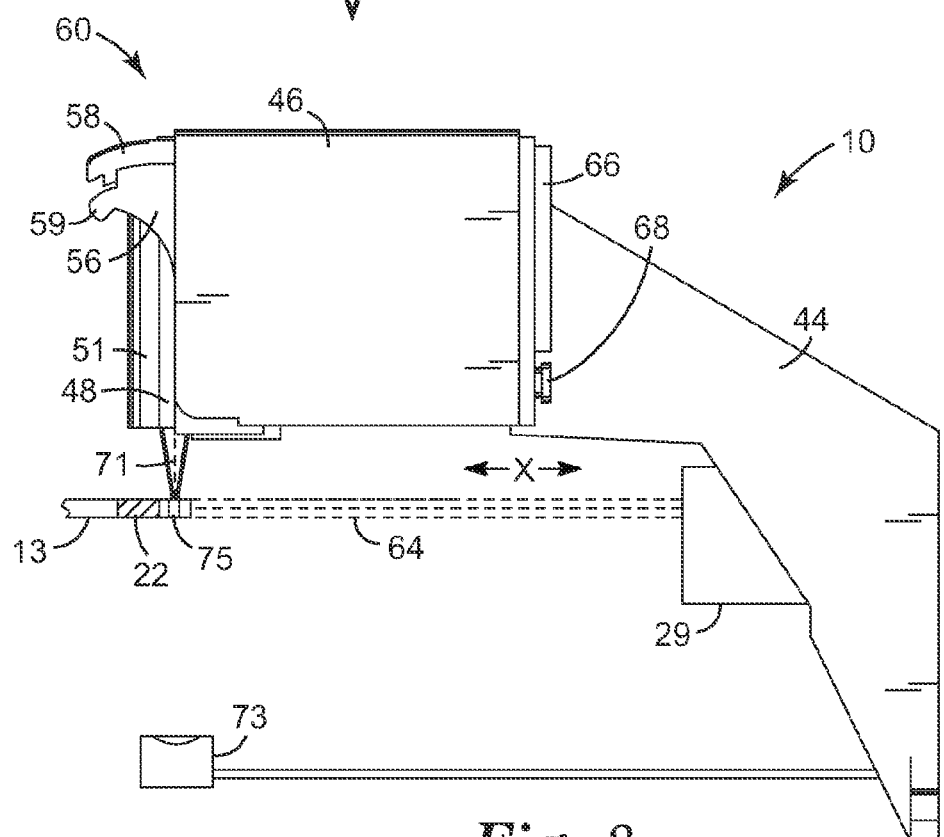
FIG. 8 is a side elevational view of the detection device of FIGS. 3-5, with a laser valve control system located over a slot on a disk, and a gantry system.

FIG. 8 is an illustration of the side view of an exemplary set of removable optical modules 48, 52 and 56 within the device housing with the laser valve control system located over a slot on the disk. The example of FIG. 8 is similar to FIG. 4. However, laser valve control system 51 has been positioned to aim laser light 71 from an energy source, i.e. a laser diode, through slot 75 in disk 13. Sensor 73 detects laser light 71 when the light passes through slot 75.

A gantry 60 can be used to move module housing 46 and the contained optical modules 48, 52 and 56 in a horizontal direction (shown as arrows and denoted by "X" in FIG. 8) relative to a center of disk 13. In other words, the module housing 46 and the contained optical modules 48, 52 and 56 can move radially with respect to the center of disk 13. Other directions of movement of the gantry 60 can also be employed, for example, in a two-dimensional plane, a three-dimensional space, etc. Laser light 71 may be emitted by the laser at a reduced current to produce low power radiation (e.g., near-infrared (NIR) light) for locating slot 75 in disk 13. In some cases, the gantry 60 may translate module housing 46 in the horizontal direction while laser valve control system 51 outputs laser light 71 in order to locate slot 75.

Sensor 73 may detect laser light 71 once the laser light travels through slot 75, causing sensor 73 to output an electrical signal representative of the sensed low-power laser light 71 to control unit 23. Upon receiving the electrical signal from sensor 73, control unit 23 maps the sensed disk position to a known location of rotating platform 25 and constructs a position map that identifies the position of each valve of disk 13 relative to the known position of rotating platform 25. Control unit 23 may subsequently use the constructed position map to move the laser, rotate the disk, or both, so as to target the desired valves of disk 13. In other embodiments, sensor 73 may be located on the same side of disk 13 as laser valve control system 51 to detect laser light 71 from a reflective portion or portions of disk 13.

Upon positioning laser valve control system 51 over a selected valve, control unit 23 directs the laser valve control system to deliver short pulses of high-power energy (e.g., 1 second at 1 Watt (W)) to open the selected valve. Valves may be constructed out of a polymer or similar material that absorbs the emitted electromagnetic energy, i.e., laser light 71, causing the polymer to rupture, thereby opening a channel between an inner holding chamber and an outer process chamber. Other energy sources may be used (e.g., radio frequency energy sources), and materials may be selected that absorb the produced energy and rupture (i.e., open). Once the valves are opened, rotation of disk 13 directs contents of the respective inner holding chamber to the respective outer process chamber.

In some embodiments, laser valve control system 51 and slot sensor trigger 27 may communicate for effective positioning of disk 13. For example, slot sensor trigger 27 may generally locate the radial position of disk 13 by sensing the presence of slot 75. Laser valve control system 51 may specifically detect each of the edges of slot 75 for a more accurate radial and angular position of disk 13. As the edges of slot 75 are smaller features than the slot 75 itself, laser valve control system 51 may provide a higher spatial resolution detection system than slot sensor trigger 27. Alternatively, slot sensor trigger 27 may be able to provide higher temporal resolution as slot 75 position may be detected at high rotational speeds. Edges of slot 75 may be undetectable by laser valve control system 51 at high rotational speeds.

Further, some embodiments may not include a gantry 60 to horizontally (or radially) move components for aligning light paths with structures on disk 13. For example, laser valve control system 51 and optical modules 48, 52 and 56 may be fixed at appropriate radial distances from a center of disk 13. As another example, laser valve control system 51 and/or optical modules 48, 52 and 56 may pivot under the direction of control unit 23 to aim laser light at different radial positions of disk 13.

Figure 9:
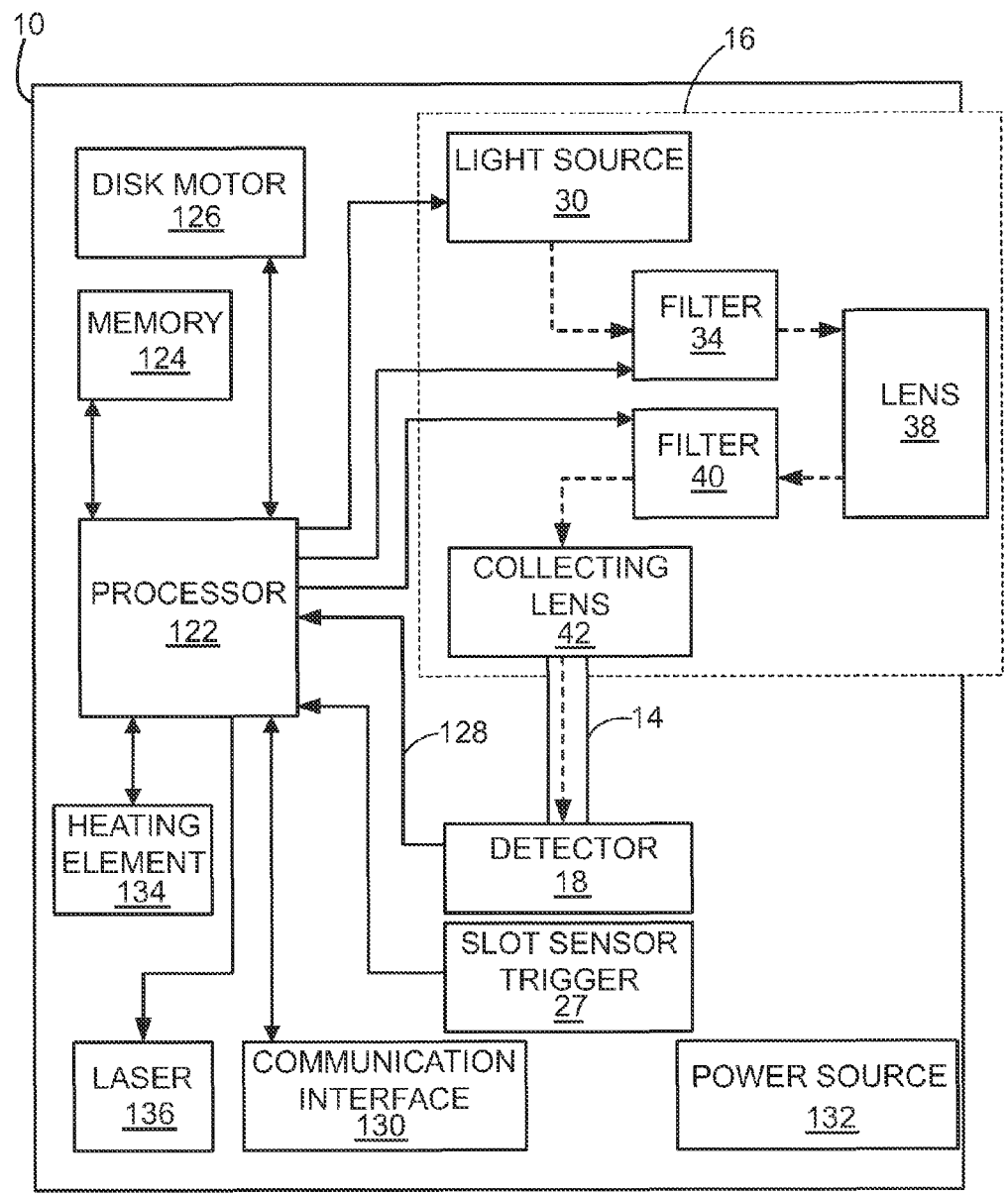
FIG. 9 is a schematic block diagram illustrating an example embodiment of the multiplex fluorescence detection device in further detail.

FIG. 9 is a functional block diagram of the multiplex fluorescence detection device 10. In particular, FIG. 9 indicates the electrical connections between device components (shown in solid arrows) and the general paths of light through the components (shown in broken arrows). In the example of FIG. 9, device 10 includes at least one processor 122 or other control logic, memory 124, disk motor 126, light source 30, excitation filter 34, lens 38, detection filter 40, collecting lens 42, detector 18, slot sensor trigger 27, communication interface 130, heating element 134, laser 136 and power source 132. As shown in FIG. 9, lens 38 and collecting lens 42 need not be electrically connected to another component. Further, light source 30, filters 34 and 40, lens 38 and collecting lens 42 are representative of one optical module 16. Although not illustrated in FIG. 9, device 10 may contain additional optical modules 16, as described previously. In that case, each additional optical module may include components arranged substantially similarly as to those shown in FIG. 9.

Light follows a certain path through several components in FIG. 9. Once light is emitted by light source 30, it enters excitation filter 34 and leaves as light of a discrete wavelength. It then passes through lens 38 where it leaves detection device 10 and excites sample 22 within a process chamber (not shown). Sample 22 responds by fluorescing at a different wavelength or backscattering the light, at which time this light enters lens 38 and is filtered by detection filter 40. Filter 40 removes background light of wavelengths outside of the desired fluorescence or backscattered light from sample 22. The remaining light is sent through collecting lens 42 and enters a leg of fiber optic bundle 14 before being detected by detector 18. Detector 18 subsequently amplifies the received light signal.

Processor 122, memory 124 and communication interface 130 may be part of control unit 23, and as mentioned above, one or more components of the control unit 23 may be located within the optical module 16. Processor 122 controls disk motor 126 to rotate or spin disk 13 as needed to collect optical (e.g., fluorescence) information or move fluid through disk 13. Processor 122 may use disk position information received from slot sensor trigger 27 to identify the location of chambers on disk 13 during rotation and synchronize the acquisition of optical data received from the disk. Processor 122 may also pause, cancel and/or output and error code, alert or notification if a selected volume of material is not detected when necessary in a particular chamber of disk 13.

Processor 122 may also control when the light source 30 within optical module 16 is powered on and off. In some embodiments, processor 122 controls excitation filter 34 and detection filter 40. Depending on the sample being illuminated, processor 122 may change the filter to allow a different wavelength of excitation light to reach the sample or a different wavelength of fluorescence to reach collecting lens 42. In some embodiments, one or both filters may be optimized for the light source 30 of the particular optical module 16 and not changeable by processor 122.

Collecting lens 42 is coupled to one leg of fiber bundle 14 that provides an optical path for the light from the collecting lens to detector 18. Processor 122 may control the operation of detector 18. While detector 18 may constantly be detecting all light, some embodiments may utilize other acquisition modes. Processor 122 may determine when detector 18 collects data and may programmatically set other configuration parameters of detector 18. In one embodiment, detector 18 is a photomultiplier tube that captures fluorescence information from light provided by collecting lens 42. In response, detector 18 produces an output signal 128 (e.g., an analog output signal) representative of the received light. Although not shown in FIG. 9, detector 18 may concurrently receive light from other optical modules 16 of device 10. In that case, output signal 128 electrically represents a combination of the optical input received by detector 18 from the various optical modules 16, and can also include information relating to the presence of a selected volume of material in a particular chamber on disk 13.

Processor 122 may also control data flow from device 10. Data such as sampled fluorescence or detected backscattered light from detector 18 (e.g., at particular positions (e.g., gantry positions) relative to particular chambers on disk 13 for determining whether a selected volume of material is present in particular chamber(s)), sampled fluorescence from detector 18 (e.g., for determining the results of a particular assay), temperature of the samples from heating element 134 and related sensors, and disk rotation information may be stored into memory 124 for analysis. Processor 122 may comprise any one or more of a microprocessor, digital signal processor (DSP), application specific integrated circuit (ASIC), field-programmable gate array (FPGA), or other digital logic circuitry. Moreover, processor 122 can provide an operating environment for firmware, software, or combinations thereof, stored on a computer-readable medium, such as memory 124.

Memory 124 may include one or more memories for storing a variety of information. For example, one memory may contain specific configuration parameters, executable instructions, and one may contain collected data. Therefore, processor 122 may use data stored in memory 124 for controlling device operation and calibration. Memory 124 may include any one or more of a random access memory (RAM), read-only memory (ROM), electronically-erasable programmable ROM (EEPROM), flash memory, or the like.

Processor 122 may additionally control heating element 134. Based upon the instructions contained within memory 124, the heating element 134 may be selectively driven to control the temperature of one or more chambers according to desired heating profiles. Generally, heating element heats one radial section of disk 13 as the disk spins. Heating element 134 may comprise a halogen bulb and reflector for focusing heating energy on a specific area of disk 13, or more particularly, on the rotating platform 25, or a specific area thereof, such that heat can then be conducted from the platform 25 to a specific area of the disk 13. In some embodiments, heating element 134 may heat one or more chambers sequentially. Such embodiments would require disk 13 to be stationary while a portion of the platform 25 and/or the disk 13 is heated. In any embodiment, heating element 134 may be capable of turning on and off extremely quickly as needed.

Laser 136 is used to control valve opening which allows contents of a holding chamber to flow to another chamber on disk 13, e.g., a process or detection chamber. Processor 122 and supporting hardware drives laser 136 to selectively open specific valves contained within disk 13. Processor 122 may interact with a laser sensor (such as sensor 73 of FIG. 8) positioned underneath, or otherwise relative to, disk 13 for determining the position of the laser relative to the desired valve. Processor 122 may then interact with disk motor 126 to rotate the rotating platform 25, and accordingly, disk 13, into position. When in position, processor 122 outputs signals to direct laser 136 to produce a burst of energy targeted at the valve. In some cases, the burst may last for approximately 0.5 seconds, while other embodiments may include opening times of shorter or greater duration. A laser energy and pulse duration may be controlled by processor 122 through communication with laser 136.

Processor 122 utilizes communication interface 130 to communicate with data acquisition system 21. The communication interface 130 may include a single method or combination of methods to transfer data. Some methods may include a universal serial bus (USB) port or IEEE 1394 port for hardwire connectivity with high data transfer rates. In some embodiments, a storage device may be directly attached to one of these ports for data storage or post processing. The data may be pre-processed by processor 122 and ready for viewing, or the raw data may need to be completely processed before analyzing can begin.

Communications with detection device 10 may also be accomplished by radio frequency (RF) communication or a local area network (LAN) connection. Moreover, connectivity may be achieved by direct connection or through a network access point, such as a hub or router, which may support wired or wireless communications. For example detection device 10 may transmit data on a certain RF frequency for reception by the target data acquisition device 21. Data acquisition device 21 may be a general purpose computer, a notebook computer, a handheld computing device, or an application-specific device. Further, multiple data acquisition devices may receive the data simultaneously. In other embodiments, the data acquisition device 21 may be included with detection device 10 as one integrated detection and acquisition system.

In addition, detection device 10 may be able to download updated software, firmware, and calibration data from a remote device over a network, such as the internet. Communication interface 130 may also enable processor 122 to monitor inventory or report any failures or errors. If operational problems occur, processor 122 may be able to output error information to assist a user in trouble shooting the problems by providing operational data. For example, processor 122 may provide information to help the user diagnose a failing heating element, a synchronization problem, or a failure in various metering and/or valving structures in disk 13 (e.g., by receiving information from detector 18 indicating that a selected volume of material is not present in one or more chambers of disk 13).

Power source 132 delivers operating power to the components of device 10. Power source 132 may utilize electricity from a standard 115 Volt electrical outlet or include a battery and a power generation circuit to produce the operating power. In some embodiments, the battery may be rechargeable to allow extended operation. For example, device 10 may be portable to detection of biological samples in an emergency, such as a disaster area. Recharging may be accomplished through the 115 Volt electrical outlet. In other embodiments, traditional batteries may be used.

Figure 10:
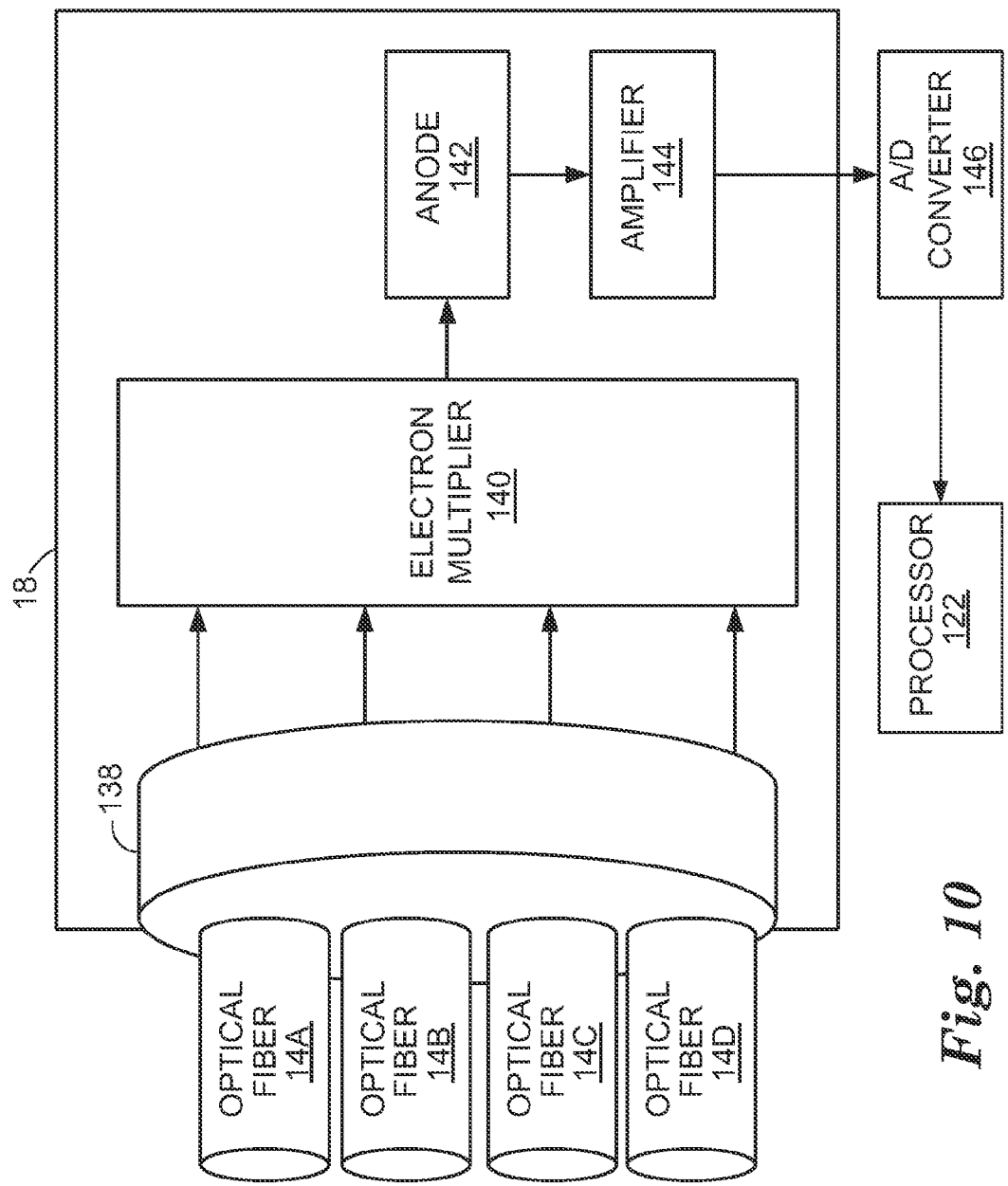
FIG. 10 is a block diagram of a single detector coupled to four optical fibers of an optical fiber bundle.

FIG. 10 is a functional block diagram of the single detector 18 coupled to four optical fibers of the optical fiber bundle 14. In this embodiment, detector 18 is a photomultiplier tube. Each leg of fiber optic bundle 14, optical fiber 14A, optical fiber 14B, optical fiber 14C and optical fiber 14D, couples to an optical input interface 138 of detector 18. In this manner, light carried by any of optical fibers 14 is provided to a single optical input interface 138 of detector 18. The optical input interface 138 provides the aggregate light to electron multiplier 140. Anode 142 collects the electrons and produces a corresponding analog signal as output signal.

In other words, as shown, the optical fibers 14 fit within the input optical aperture for detector 18. Consequently, detector 18 may be used to detect light from each leg of optic bundle 14 simultaneously. Optical input interface 138 provides the light to electron multiplier 140. For a photomultiplier tube, the photons from the optical fibers first hit a photoemissive cathode, which in turn releases photoelectrons. The photoelectrons then cascade by hitting a series of dynodes, more photoelectrons being emitted upon contact with each dynode. The resulting group of electrons has essentially multiplied the small light signals originally transmitted by the optical fibers 14. The increased number of electrons finally are collected by anode 142. This current from anode 142 is transferred by a current to voltage amplifier 144 as an analog output signal which is representative of the optical florescent signals from the sample provided by the plurality of optical modules 16.

In some embodiments, control unit 23 can include an analog to digital (A/D) converter 146 that converts the analog signal to a stream of sampled digital data, i.e., a digital signal. Processor 122 receives the digital signal and stores the sampled data in memory 124 for communication to data acquisition device 21, as described above. In some embodiments, A/D converter 146 may be contained within detector 18 instead forming a portion of control unit 23.

In this manner, a single detector 18 may be utilized to collect all light from the optic bundle 14 and produce a signal representative thereof. Once the signal is amplified by amplifier 144 and converted to a digital signal, it may be digitally separated into data corresponding to the light collected by each individual optical module 16. The entire (i.e., aggregate) signal may be separated by frequency range into each detected signal representative of each fluorescence. These frequencies may be separated by a digital filter applied by data acquisition device 21 or within device 10.

In other embodiments, the amplified signal may be separated by frequency using analog filters and sent to separate channels before A/D converter 146. Each channel may then be separately digitized and sent to the data acquisition device. In either case, the single detector is able to capture all florescence information, or other optical signals or information, from each optical module 16. Data acquisition device 21 may then plot and analyze the signal acquired from each well of disk 13 in real-time without the need for multiple detectors.

In some embodiments, detector 18 may not be a photomultiplier tube. In general, detector 18 may be any type of analog or digital detection device capable of capturing light from multiple legs of an optical delivery mechanism, i.e., fiber bundle 14, and producing a transmittable representation of the captured light.

Figure 11:
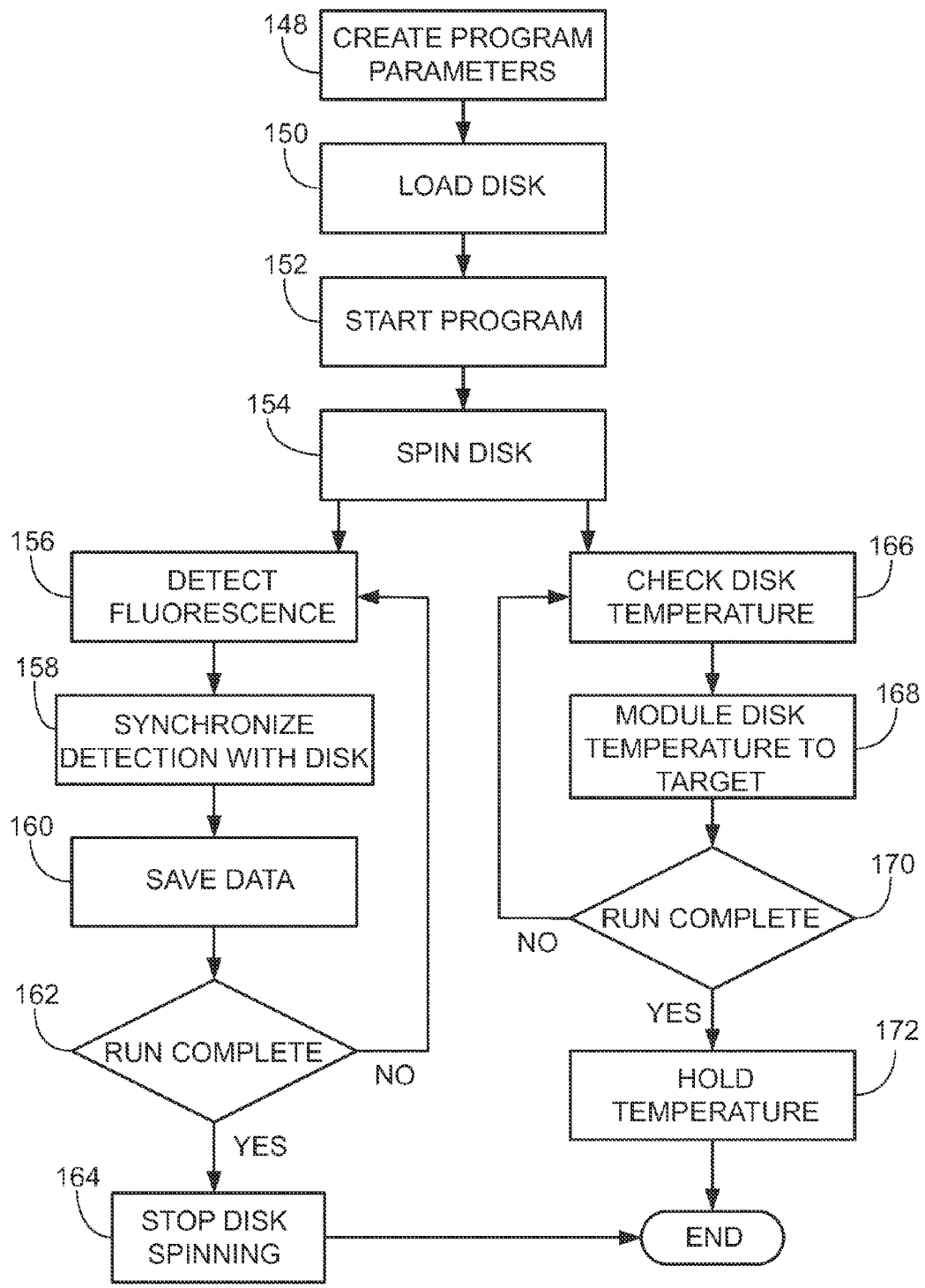
FIG. 11 is a flow diagram illustrating exemplary operation of the multiplex fluorescence detection device.

FIG. 11 is a flow diagram illustrating the operation of the multiplex fluorescence detection device 10. Initially, at step 148, a user specifies program parameters on the data acquisition device 21 or via an interface with control unit 23. For example, these parameters may include a velocity and time period for rotating disk 13, define temperature profiles for the reaction, and sample locations on disk 13.

Next, at step 150, the user can load disk 13 into the detection device 10. Upon securing the device 10, the user can start the program (152), causing control unit 23 to begin spinning the disk (154) at the specified rate. After the disk has begun to spin, two concurrent processes may occur.

First, at step 156, the detection device 10 can start to detect fluorescence or other optical signals or information from the excitation light produced by one or more reactions within one or more samples. The detector 18 amplifies the optical (e.g., fluorescence) signals from each sample, which are synchronized to each respective sample and time at which the fluorescence was emitted (158). During this process, processor 122 saves the captured data to memory 124 and may communicate the data to data acquisition device 21 in real-time to monitor the progress of the run and for additional processing (160). Alternatively, processor 122 may save the data within device 10 until the program is complete. The processor 122 continues to detect florescence of the samples and save data until the program is complete (162). Once the run is complete, control unit 23 stops the disk from spinning (164).

During this process, control unit 23 can monitor the disk temperature (166) and modulate the disk, or each sample, temperature to attain the target temperature for that time (168). The control unit 23 can continue to monitor and control the temperatures until the program is complete (170). Once the run is complete, control unit 23 holds the temperature of the samples to a target storage temperature, usually 4 degrees Celsius (172).

The operation of device 10 may vary from the example of FIG. 11. For example, the disk revolutions per minute may be modified throughout the program, various chambers on disk 13 can be monitored to determine whether a selected volume of a material is present, and/or laser 136 may be utilized to open valves between chambers on the disk to allow for multiple reactions and/or material movement. These steps may occur in any order within the operation, depending on the program the user defines.

Figure 12:
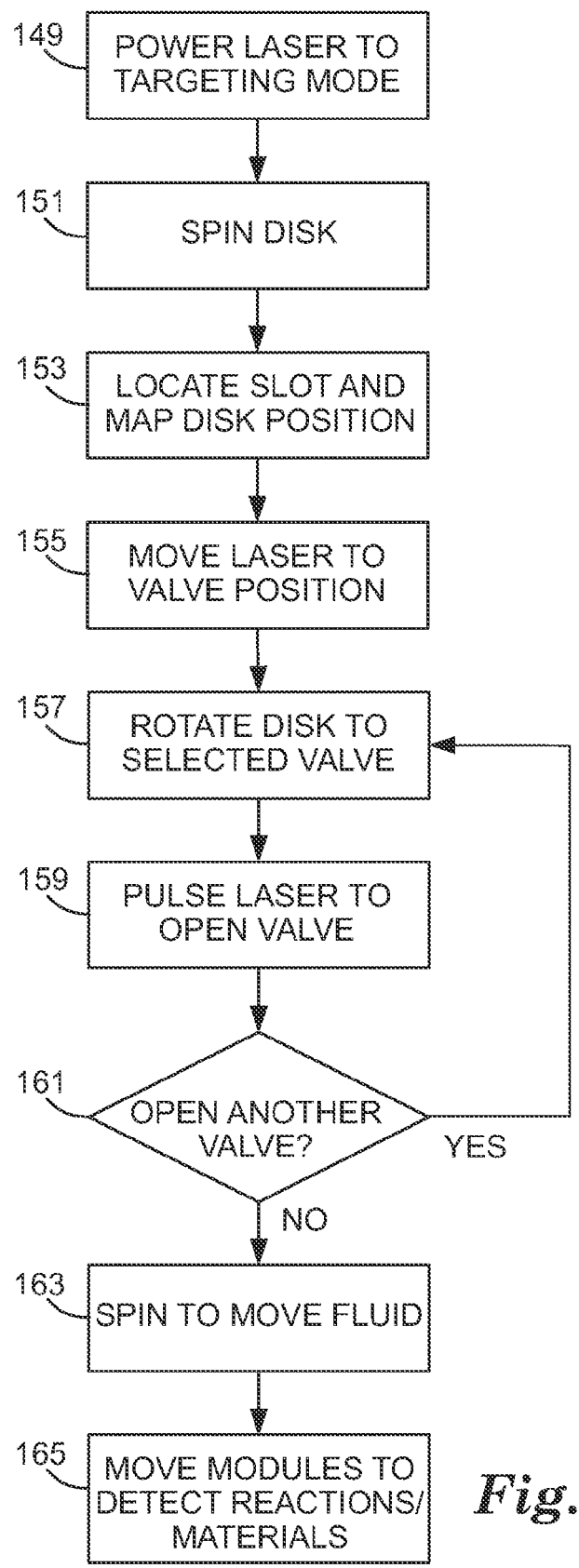
FIG. 12 is a flow diagram illustrating exemplary operation of the laser valve control system for the detection device.

FIG. 12 is a flow diagram illustrating exemplary operation of laser valve control system 51 of detection device 10. For exemplary purposes, FIG. 12 will be described in reference to disk 13 and device 10, with particular reference to FIG. 8.

Initially, control unit 23 places laser valve control system 51 in a low-power mode (also referred to as a "targeting mode") that utilizes a reduced current (149). Next, control unit 23 initiates the rotation of disk 13A (151). Sensor 73 (e.g., an NIR sensor) outputs a trigger signal to control unit 23 upon detecting the edges of slot 75 as disk 13 rotates, allowing control unit 23 to accurately map the orientation of disk 13 and the locations of the valves on disk 13 to the known position of rotating platform 25 of device 10 (153).

Using the mapping, control unit 23 engages the gantry 60 to move laser valve control system 51 to the known location of the valves relative to a center or axis of rotation of disk 13 (i.e., positioned to the left of FIG. 8). Control unit 23 then rotates disk 13 to the first selected valve to be opened (157). Next, control unit 23 places laser valve control system 51 in a high-power mode and directs the system to produce a pulse of high energy laser light 71 to open the valve (159). If an additional valve needs to be opened (161), control unit 23 rotates disk 13 to the next valve (157) and opens the valve (159). This process continues until all valves that are desired to be opened have been opened. Then, control unit 23 spins the disk 13 to move fluid, e.g., from a chamber located closer to an axis of rotation of disk 13 (sometimes referred to as "input chambers" or "holding chambers"), through an open valve, and into a chamber (sometimes referred to as a "process chamber" or a "detection chamber") located further from the axis of rotation, such as toward a periphery of disk 13 (163). In other embodiments, control unit 23 may continuously spin disk 13 while directing laser valve control system 51 to open valves.

Finally, control unit 23 can engage the gantry 60 to move the optical modules 48, 52 and/or 56 to a radial position over the process chambers and commence detection of fluorescence or other optical signals from the materials and/or reactions in the process chambers (165). In some embodiments, the contents of the holding chambers may act to deactivate or stabilize products in the process chambers. In such cases, the detection device 10 may or may not need to monitor the new samples or reactions.

Figure 13A:
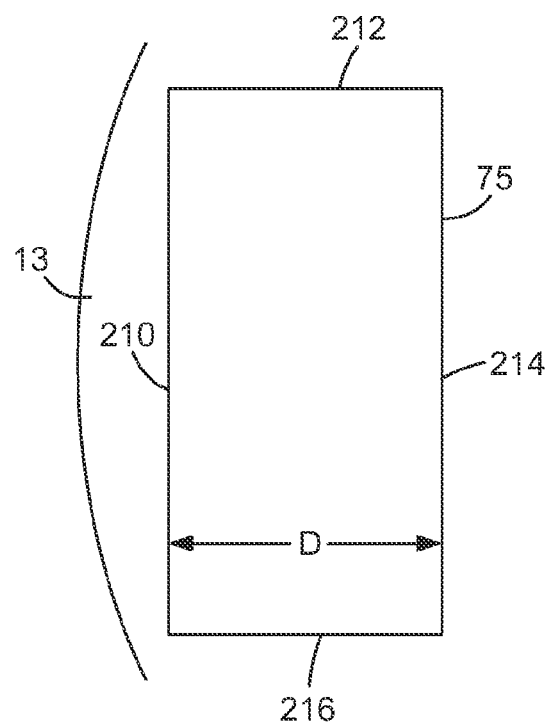
FIG. 13A is an exemplary diagram of a slot in a disk.
Figure 13B:
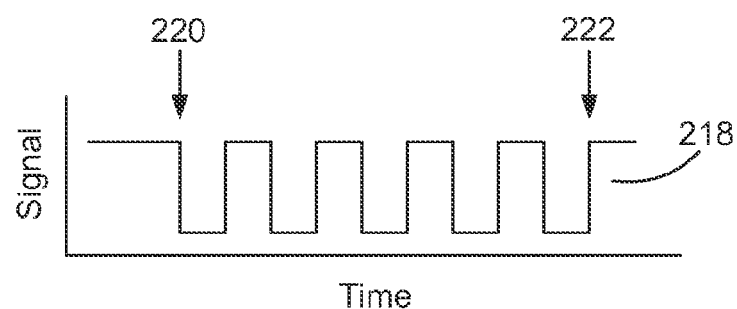
FIG. 13B is a timing diagram illustrating an exemplary method for detecting inner and outer edges of a slot in a disk.
Figure 13C:
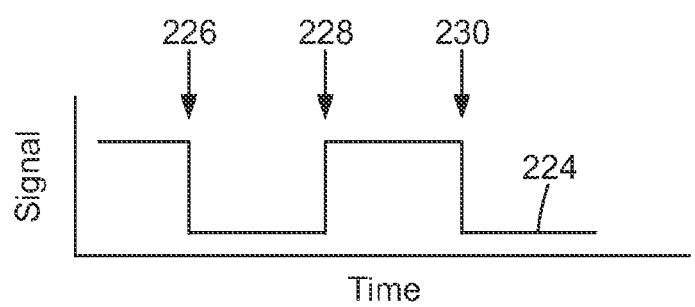
FIG. 13C is a timing diagram illustrating an exemplary method for determining a home position of a laser valve control system.

FIG. 13A shows an exemplary diagram of a slot 75 in a disk. In FIGS. 13A, 13B and 13C, disk 13 will be used as an exemplary disk in device 10. Slot 75 includes outer edge 210, inner edge 214, leading edge 212 and trailing edge 216. Laser valve control system 51 detects each edge to provide an accurate map of disk 13 position. Distance D is the inner edge radial position subtracted from the outer edge radial position of slot 75. Each edge 210, 212, 214 and 216 create the detectable boundary between disk 13 material and the void in the disk described as slot 75. In some embodiments, slot 75 may be of any shape or size.

FIG. 13B illustrates a timing diagram illustrating an exemplary method for detecting the inner and outer edges of a slot in a disk. Control unit 23 moves laser valve control system 51 away from disk 13. Disk 13 is spun while the gantry 60 moves laser valve control system 51 towards the center, or axis of rotation, of disk 13.

Sensor 73 detects laser light 71 (FIG. 8) only when slot 75 allows laser light 71 to pass through disk 13. A signal 218 from sensor 73 changes at spike 220 as outer edge 210 of slot 75 is detected while the gantry 60 is advancing inward. Signal 218 continues to modulate as slot 75 intermittently passes through laser light 71. Spike 222 indicates the last signal change which control unit 23 marks as inner edge 214 of slot 75. The gantry positions of the outer and inner edges 210 and 214 of the slot 75 are recorded. Control unit 23 now has a radial component of the map of disk 13 position. Control unit 23 moves laser valve control system 51 to the radial position halfway between the inner and outer edge radial positions. This position would be the radial position of inner edge 214 plus half of distance D. Positioning laser valve control system 51 to this location of slot 75 allows the system to detect the angular position of slot 75 without roundness of a corner of slot 75, e.g. the corner between inner edge 214 and trailing edge 216, causing error in the angular position of an edge of the slot 75. In some embodiments, disk 13 may not need to be rotated for laser valve control system 51 to detect the inner and outer edges of slot 75.

FIG. 13C illustrates a timing diagram illustrating an exemplary method for determining the home position of a laser valve control system 51. Signal 224 is delivered to control unit 23 which indicates the presence of laser light 71. Laser valve control system 51 locates leading edge 212 and trailing edge 216 of slot 75 on disk 13.

Signal 224 is constant as disk 13 is stationary. Once disk 13 is slowly rotated clock-wise, spike 226 indicates the angular position of leading edge 212 of slot 75. Laser light 71 is detected by sensor 73 until trailing edge 216 is detected as spike 228. Control unit 23 then stops disk 13 and slowly rotates disk 13 counter-clockwise until spike 230 indicates the presence of trailing edge 216 once more. Control unit 23 stores this angular position as the home angular position. Laser valve control system 51 now uses the radial position from FIG. 13B and angular position from FIG. 13C to locate valves or other structures on disk 13. In other embodiments, laser valve control system 51 may only detect leading edge 212 or trailing edge 216 for effective positioning of disk 13.

In some embodiments, the drive system (e.g., including a motor) and/or rotating platform 25 can be operated in two different modes—a velocity mode and a position mode. The radial home position, or gantry home, can be determined under constant velocity when the drive system is in the velocity mode (e.g., at 1500 rpm). After the gantry home is determined, the motor can be slowed to a stop and switched to position mode, in which it can slowly raster from one tick (i.e., position) to the next, looking for the gantry home position. The difference between the velocity mode and the position mode can be the proportional integral derivative (PID) constants that are used by the drive system. The position mode can allow for tight control at any position, which, for example, can be used for valving. The velocity mode can be used when a stable velocity is needed, for example, during fluorescence data acquisition.

In some embodiments, disk 13 may be rotated in the opposite direction. In other embodiments, the exemplary signals from FIGS. 13B and 13C may be inverted and in any proportion relating the signal intensity to time. In other embodiments, laser valve control system 51 may first detect the angular position of disk 13 before detecting the radial position of disk 13. The order of the described positioning method may be changed to accommodate certain applications, disks or technician preference.

Figure 14:
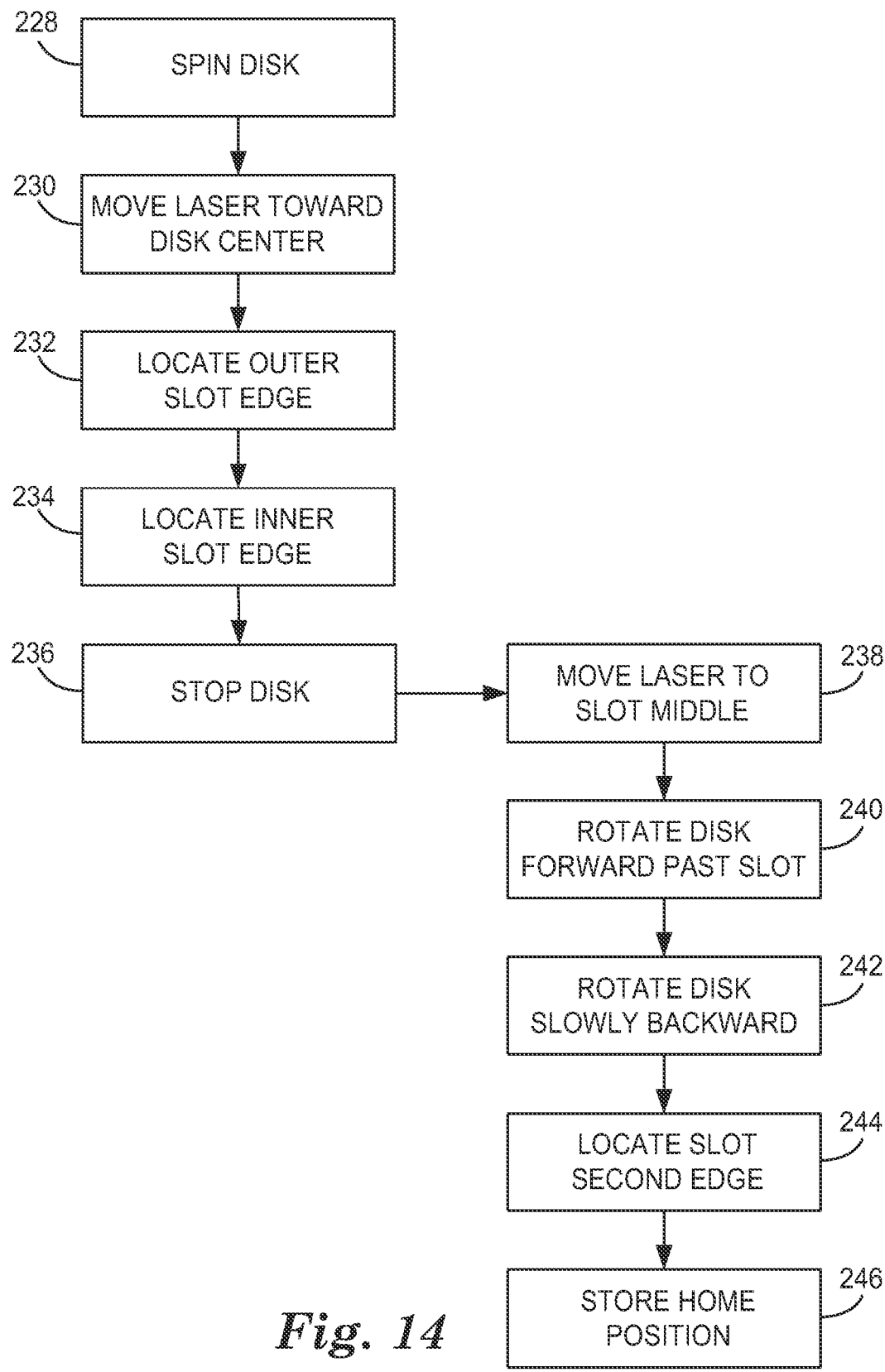
FIG. 14 is a flow diagram illustrating exemplary determination of a home position of a laser valve control system.

FIG. 14 is a flow diagram illustrating an exemplary determination of the home position of a laser valve control system. Control unit 23 can begin by spinning disk 13 (228). From outside of disk 13, the gantry 60 can move laser valve control system 51 toward the center of disk 13 (230). Laser valve control system 51 can locate outer edge 210 of slot 75 in disk 13 and save that outer radial position (232). As the gantry 60 continues to move, laser valve control system 51 can locate inner edge 214 of slot 75 when laser light 71 is no longer detected by sensor 73 and saves that inner radial position (234). Control unit 23 can store the two radial positions and stops the rotation of disk 13 (236).

Control unit 23 can then move laser valve control system 51 to the radial position directly in the middle between the inner and outer radial positions (238). Control unit 23 can slowly rotate disk 13 to move both leading edge 212 and trailing edge 216 of slot 75 past laser valve control system 51 (240). Once trailing edge 216 is detected, the control unit can slowly rotate disk 13 in the opposite direction (242). Upon detection of trailing edge 216 of slot 75 again, control unit 23 can save the location of the trailing edge (244) as the zero angular position or home angular position. Control unit 23 now has radial and angular positions of slot 75 and can store this information as the home position of disk 13 (246).

In some cases, slot sensor trigger 27 may work together with laser valve control system 51 to accurately limp disk 13 position. For example, slot sensor trigger 27 may provide high resolution temporal position information while laser valve control system 51 provides high resolution spatial position information. Since both systems use the same structure of disk 13, cooperative positioning may provide more accurate positioning information.

Figure 15:
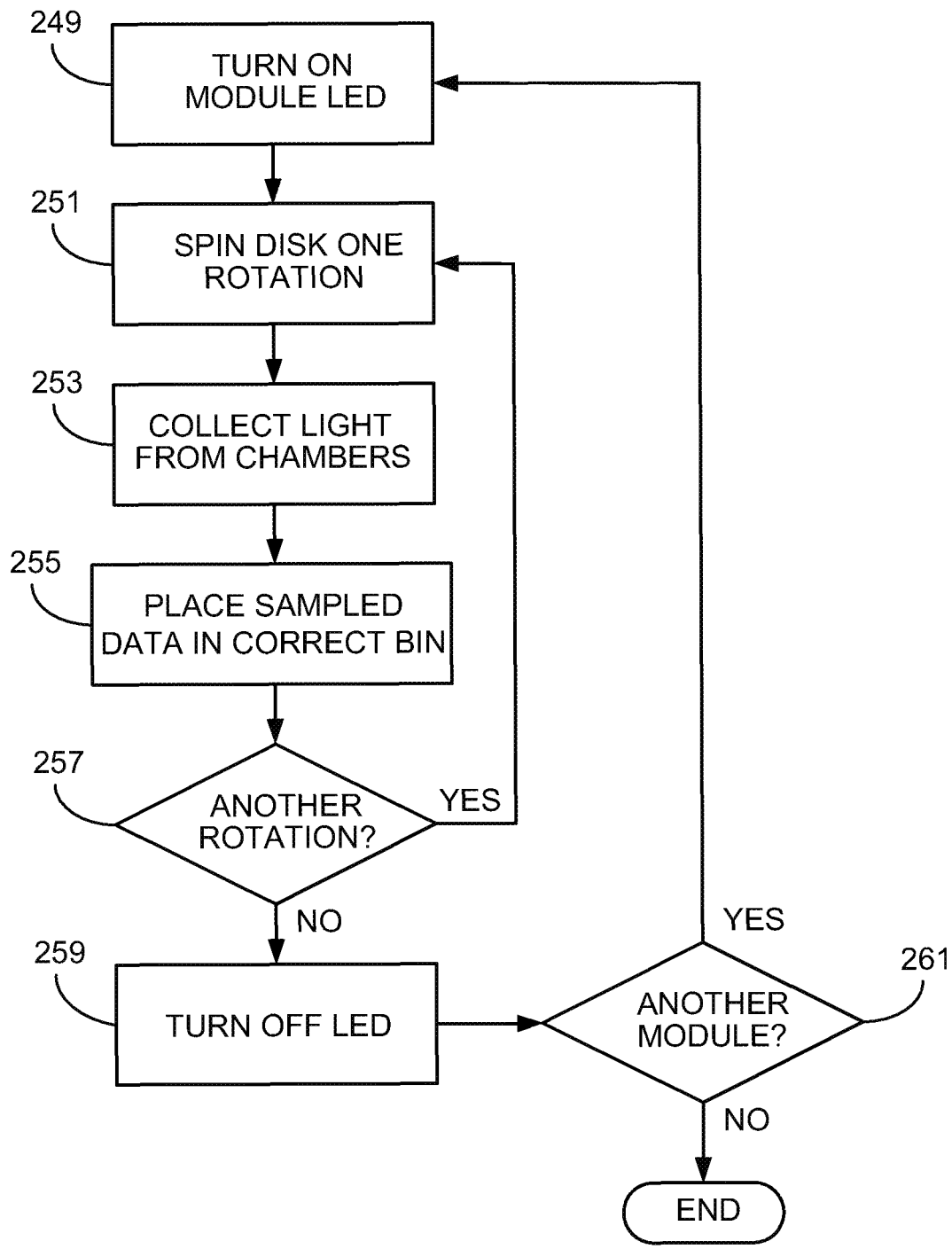
FIG. 15 is a flow diagram illustrating an exemplary method of detecting light and sampling data from a disk.

FIG. 15 is a flow diagram illustrating an exemplary method of detecting light and sampling data from the disk 13. Initially, a user specifies which optical modules 48, 52, 56 will detect fluorescence from disk 13, and control unit 23 turns on the LED of a module (249). Once the LED has warmed to steady state, control unit 23 spins disk 13, e.g., at the rate of approximately 1470 revolutions per minute (251) until the disk slot 75 is detected by slot sensor 27. The control unit 23 can begin data acquisition of the fluorescence for one full rotation. During that rotation, the module collects light fluoresced from the process (or "detection") chambers of disk 13 (253), and control unit 23 places a desired number of samples (e.g., 16) from each process chamber in the memory BIN associated with each process chamber (255). The control unit 23 can detect the second passage of the slot 75 to ensure that the data was acquired at the correct motor speed, and control unit 23 can place the time-dependent data in memory.

If disk 13 needs to be spun another rotation (257), control unit 23 executes another revolution of disk 13 (251). If the desired number of revolutions have been sampled, the module has completed detection with the LED. For example, if 16 revolutions have been sampled, and each revolution acquires 16 samples from each process chamber, each process chamber was sampled a total of 256 times. After the desired number of revolutions have been completed, control unit 23 can turn the LED off (259). If another module is needed to continue detection (261), control unit 23 can turn on the next module LED (249). If no other modules are needed to collect data, control unit 23 can discontinue the collection of data from disk 13. The data acquisition device 21 can integrate the individual scans of each module and calculate a histogram value for each well and module, which can be recorded to a data file.

In some embodiments, each process chamber may be sampled more or less times than 16 samples and 16 revolutions. Control unit 23 may spin disk 13 at a faster rate to provide quicker results or spin disk 13 slower to acquire more samples.

The process illustrated in FIG. 15 can be used to detect the presence or absence of an analyte of interest (e.g., using fluorescence detection), and can also be used to collect information relating to whether a selected volume of material is present in a particular chamber on the disk 13, for example, using fluorescence detection and/or backscattered light, as described above. While the disk 13 is spinning, material present in a chamber in the disk 13 will be forced against a radially outermost edge of the chamber. As a result, the gantry 60 can index one or more optical modules from a radially outward position to a radially inward position, for example, beginning past the radially outermost edge of the chamber, and moving toward a center of the disk 13 along a radius. Because the material will be forced against the outermost edge of the chamber while the disk 13 is rotating, if the volume of the material in the chamber is less than the internal volume of the chamber, a meniscus layer or fluid level of the material will be present at a position (e.g., a radial position) that is between a radially innermost edge of the chamber and a radially outermost edge of the chamber. Such a fluid level can be detected, for example, by a change in fluorescence or by a refraction of reflected backscattered electromagnetic energy.

The gantry 60 can move an optical module radially (e.g., inward) along that radius as the disk 13 is spinning, collecting data at a plurality of gantry positions (e.g., at a plurality of radial positions), according to the process of FIG. 15. Such data can then be analyzed for such a fluid level or meniscus. For example, a background scan can be run for each chamber of interest on the disk 13 when it is known that no material is present in the chamber(s) of interest, and another scan can be run for the chamber(s) after it is assumed that material, or a selected volume of material, should be present in the chamber(s). The two scans can then be compared to determine the radial position at which a fluid level (e.g., a meniscus layer) is detected. Alternatively, or additionally, the gantry (e.g., radial) position can be extrapolated (e.g., based on a prior calibration) to a volume. Alternatively, or additionally, a particular gantry position can be used as a threshold, such that if the gantry position at which the fluid level is detected is less than a threshold number, the data acquisition device 21 can output a result (e.g., an invalid assay, an error code, an assay failure or interruption, etc.) that a sufficient amount of a material was not present for the assay, but if the gantry position at which the fluid level is detected is greater than or equal to the threshold number, the desired volume of the material can be confirmed.

Sample Processing Devices

One exemplary sample processing device, or disk, 300 of the present disclosure is shown in FIGS. 16-22. Additional details and features of the sample processing device 300 can be found in U.S. Design patent application Ser. No. 29/392,223, filed May 18, 2011, which is incorporated herein by reference in its entirety.

The sample processing device 300 is shown by way of example only as being circular in shape. The sample processing device 300 can include a center 301, and the sample processing device 300 can be rotated about an axis of rotation A-A that extends through the center 301 of the sample processing device 300.

Figure 22:
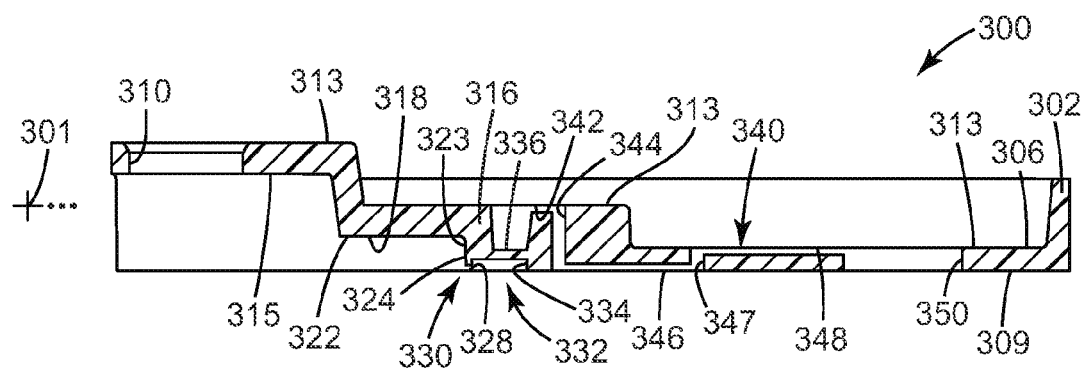
FIG. 22 is a cross-sectional side view of the sample processing device of FIGS. 16-21, taken along line 22-22 of FIG. 21.

The sample processing device 300 can be a multilayer composite structure formed of a substrate or body 302, one or more first layers 304 coupled to a top surface 306 of the substrate 302, and one or more second layers 308 coupled to a bottom surface 309 of the substrate 302. As shown in FIG. 22, the substrate 302 includes a stepped configuration with three steps or levels 313 in the top surface 306. As a result, fluid structures (e.g., chambers) designed to hold a volume of material (e.g., sample) in each step 313 of the sample processing device 300 can be at least partially defined by the substrate 302, a first layer 304, and a second layer 308. In addition, because of the stepped configuration comprising three steps 313, the sample processing device 300 can include three first layers 304, one for each step 313 of the sample processing device 300. This arrangement of fluid structures and stepped configuration is shown by way of example only, and the present disclosure is not intended to be limited by such design.

The substrate 302 can be formed of a variety of materials, including, but not limited to, polymers, glass, silicon, quartz, ceramics, or combinations thereof. In embodiments in which the substrate 302 is polymeric, the substrate 302 can be formed by relatively facile methods, such as molding. Although the substrate 302 is depicted as a homogeneous, one-piece integral body, it may alternatively be provided as a non-homogeneous body, for example, being formed of layers of the same or different materials. For those sample processing devices 300 in which the substrate 302 will be in direct contact with sample materials, the substrate 302 can be formed of one or more materials that are non-reactive with the sample materials. Examples of some suitable polymeric materials that could be used for the substrate in many different bioanalytical applications include, but are not limited to, polycarbonate, polymethyl methacrylate (PMMA), polypropylene (e.g., isotactic polypropylene), polyethylene, polyester, etc., or combinations thereof. These polymers generally exhibit hydrophobic surfaces that can be useful in defining fluid structures, as described below. Polypropylene is generally more hydrophobic than some of the other polymeric materials, such as polycarbonate or PMMA; however, all of the listed polymeric materials are generally more hydrophobic than silica-based microelectromechanical system (MEMS) devices.

Figure 17:
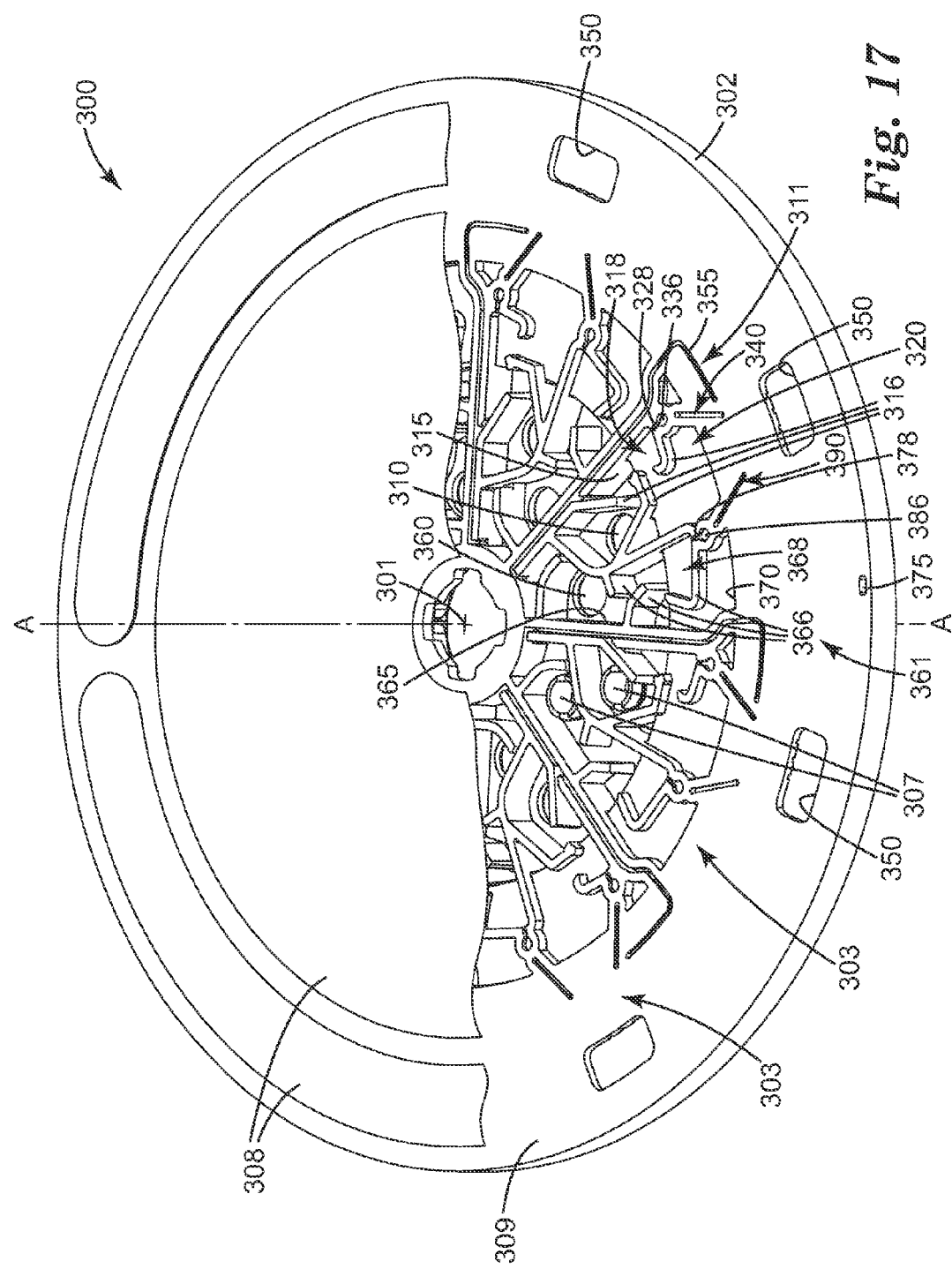
FIG. 17 is a bottom perspective view of the sample processing device of FIG. 16.
Figure 18:
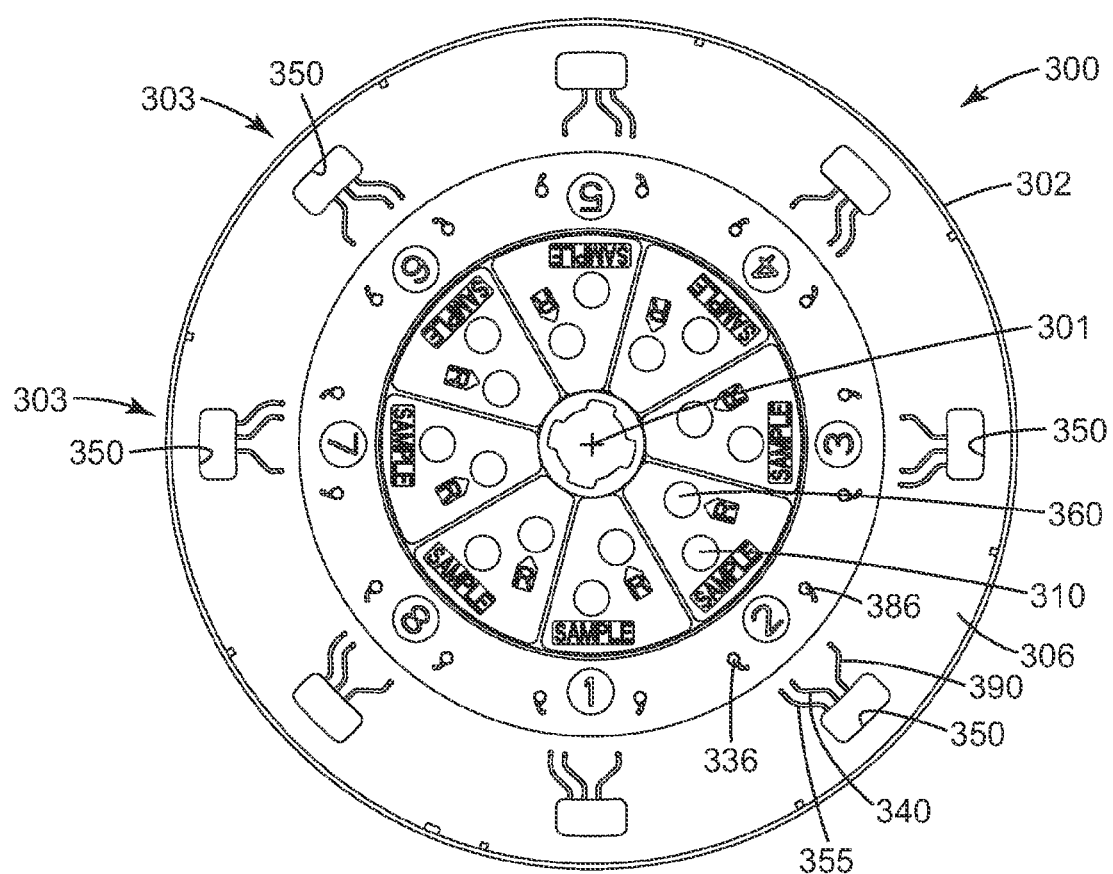
FIG. 18 is a top plan view of the sample processing device of FIGS. 16-17.
Figure 19:
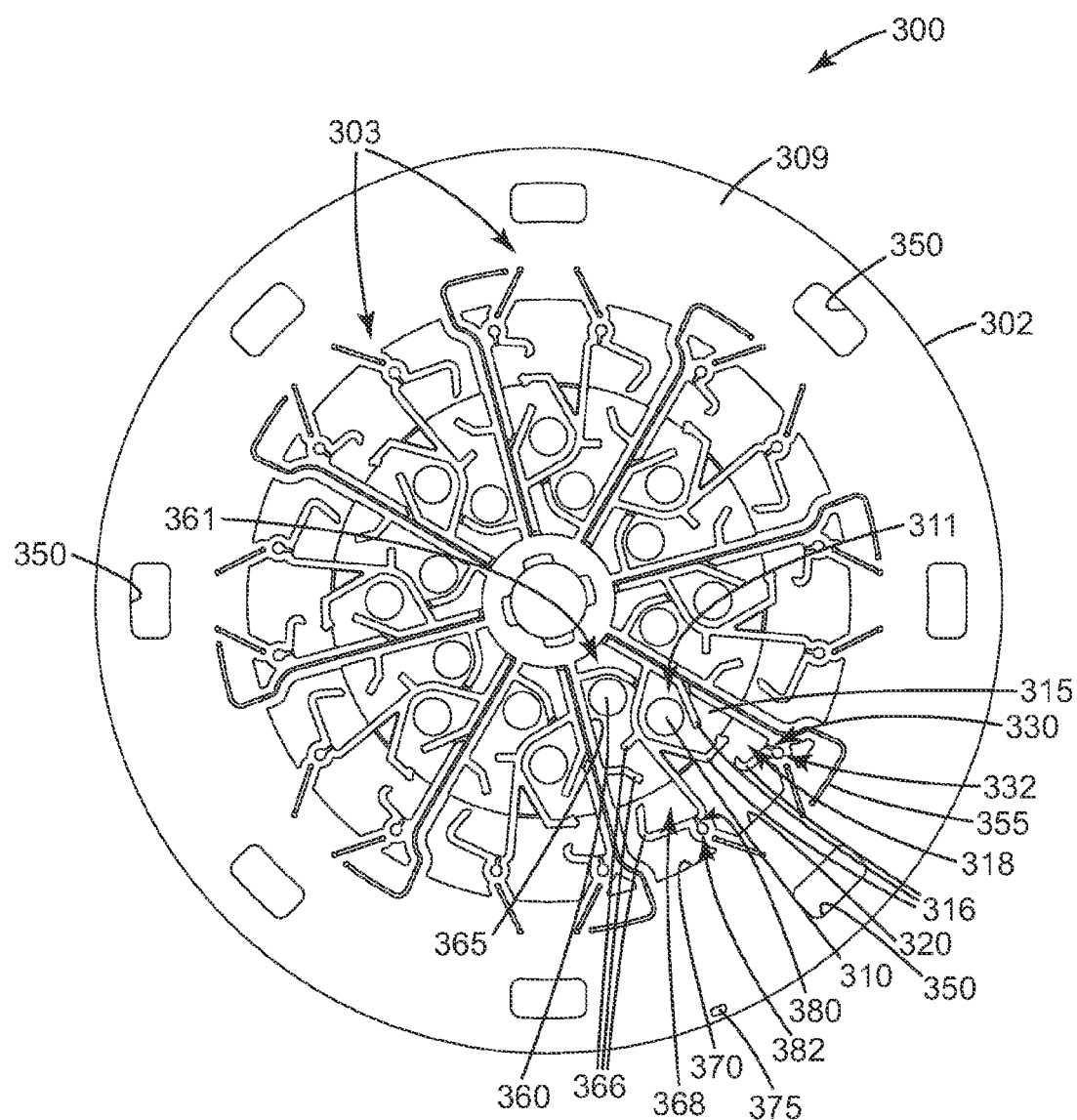
FIG. 19 is a bottom plan view of the sample processing device of FIGS. 16-18.

As shown in FIGS. 17 and 19, the sample processing device 300 can include a slot 375 formed through the substrate 302 or other structure (e.g., reflective tab, etc.) for homing and positioning the sample processing device 300, for example, relative to electromagnetic energy sources, optical modules, and the like, as described above with respect to FIGS. 12-14.

The sample processing device 300 includes a plurality of process or detection chambers 350, each of which defines a volume for containing a sample and any other materials that are to be thermally processed (e.g., cycled) with the sample. As used in connection with the present disclosure, "thermal processing" (and variations thereof) means controlling (e.g., maintaining, raising, or lowering) the temperature of sample materials to obtain desired reactions. As one form of thermal processing, "thermal cycling" (and variations thereof) means sequentially changing the temperature of sample materials between two or more temperature setpoints to obtain desired reactions. Thermal cycling may involve, e.g., cycling between lower and upper temperatures, cycling between lower, upper, and at least one intermediate temperature, etc.

The illustrated device 300 includes eight detection chambers 350, one for each lane 303, although it will be understood that the exact number of detection chambers 350 provided in connection with a device manufactured according to the present disclosure may be greater than or less than eight, as desired.

The detection chambers 350 in the illustrative device 300 are in the form of chambers, although the detection chambers in devices of the present disclosure may be provided in the form of capillaries, passageways, channels, grooves, or any other suitably defined volume.

In some embodiments, the substrate 302, the first layers 304, and the second layers 308 of the sample processing device 300 can be attached or bonded together with sufficient strength to resist the expansive forces that may develop within the detection chambers 350 as, e.g., the constituents located therein are rapidly heated during thermal processing. The robustness of the bonds between the components may be particularly important if the device 300 is to be used for thermal cycling processes, e.g., PCR amplification. The repetitive heating and cooling involved in such thermal cycling may pose more severe demands on the bond between the sides of the sample processing device 300. Another potential issue addressed by a more robust bond between the components is any difference in the coefficients of thermal expansion of the different materials used to manufacture the components.

The first layers 304 can be formed of a transparent, opaque or translucent film or foil, such as adhesive-coated polyester, polypropylene or metallic foil, or combinations thereof, such that the underlying structures of the sample processing device 300 are visible. The second layers 308 can be transparent, or opaque but are often formed of a thermally-conductive metal (e.g., a metal foil) or other suitably thermally conductive material to transmit heat or cold by conduction from a platen and/or thermal structure (e.g., coupled to or forming a portion of the rotating platform 25) to which the sample processing device 300 is physically coupled (and/or urged into contact with) to the sample processing device 300, and particularly, to the detection chambers 350, when necessary.

The first and second layers 304 and 308 can be used in combination with any desired passivation layers, adhesive layers, other suitable layers, or combinations thereof, as described in U.S. Pat. No. 6,734,401, and U.S. Patent Application Publication Nos. 2008/0314895 and 2008-0152546. In addition, the first and second layers 304 and 308 can be coupled to the substrate 302 using any desired technique or combination of techniques, including, but not limited to, adhesives, welding (chemical, thermal, and/or sonic), etc., as described in U.S. Pat. No. 6,734,401, and U.S. Patent Application Publication Nos. 2008/0314895 and 2008/0152546.

By way of example only, the sample processing device 300 is shown as including eight different lanes, wedges, portions or sections 303, each lane 303 being fluidly isolated from the other lanes 303, such that eight different samples can be processed on the sample processing device 300, either at the same time or at different times (e.g., sequentially). To inhibit cross-contamination between lanes 303, each lane can be fluidly isolated from ambience, both prior to use and during use, for example, after a raw sample has been loaded into a given lane 303 of the sample processing device 300. For example, as shown in FIG. 16, in some embodiments, the sample processing device 300 can include a pre-use layer 305 (e.g., a film, foil, or the like comprising a pressure-sensitive adhesive) as the innermost first layer 304 that can be adhered to at least a portion of the top surface 306 of the sample processing device 300 prior to use, and which can be selectively removed (e.g., by peeling) from a given lane 303 prior to use of that particular lane.

Figure 16:
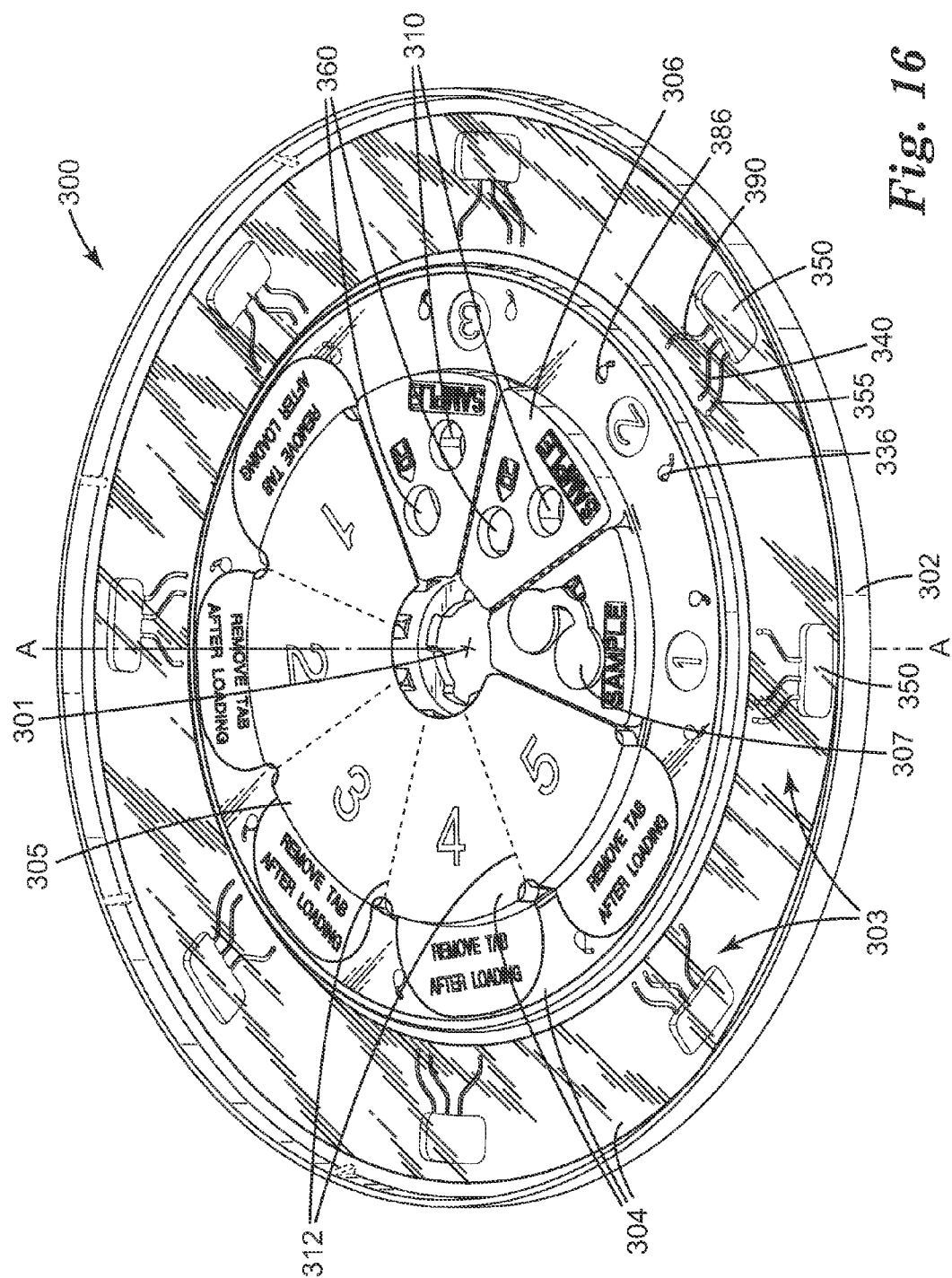
FIG. 16 is a top perspective view of a sample processing device according to one embodiment of the present disclosure.

As shown in FIG. 16, in some embodiments, the pre-use layer 305 can include folds, perforations or score lines 312 to facilitate removing only a portion of the pre-use layer 305 at a time to selectively expose one or more lanes 303 of the sample processing device 300 as desired. In addition, in some embodiments, as shown in FIG. 16, the pre-use layer 305 can include one or more tabs (e.g., one tab per lane 303) to facilitate grasping an edge of the pre-use layer 305 for removal. In some embodiments, the sample processing device 300 and/or the pre-use layer 305 can be numbered adjacent each of the lanes 303 to clearly differentiate the lanes 303 from one another. As shown by way of example in FIG. 16, the pre-use layer 305 has been removed from lane numbers 1-3 of the sample processing device 300, but not from lane numbers 4-8. Where the pre-use layer 305 has been removed from the sample processing device 300, a first input aperture or port 310 designated "SAMPLE" and a second input aperture or port 360 designated "R" for reagent are revealed.

In addition, to further inhibit cross-contamination between lanes 303, between a reagent material handling portion of a lane 303 and a sample material handling portion of the lane 303, and/or between ambience and the interior of the sample processing device 300, one or both of the first and second input apertures 310 and 360 can be plugged or stopped, for example, with a plug 307 such as that shown in FIG. 16. A variety of materials, shapes and constructions can be employed to plug the input apertures 310 and 360, and the plug 307 is shown by way of example only as being a combination plug that can be inserted with one finger-press into both the first input aperture 310 and the second input aperture 360. Alternatively, in some embodiments, the pre-use layer 305 can also serve as a seal or cover layer and can be reapplied to the top surface 306 of a particular lane 303 after a sample and/or reagent has been loaded into that lane 303 to re-seal the lane 303 from ambience. In such embodiments, the tab of each section of the pre-use layer 305 can be removed from the remainder of the layer 305 (e.g., torn along perforations) after the layer 305 has been reapplied to the top surface 306 of the corresponding lane 303. Removal of the tab can inhibit any interference that may occur between the tab and any processing steps, such as valving, disk spinning, etc. In addition, in such embodiments, the pre-use layer 305 can be peeled back just enough to expose the first and second input apertures 310 and 360, and then laid back down upon the top surface 306, such that the pre-use layer 305 is never fully removed from the top surface 306. For example, in some embodiments, the perforations or score lines 312 between adjacent sections of the pre-use layer 305 can end at a through hole that can act as a tear stop. Such a through-hole can be positioned radially outwardly of the innermost edge of the pre-use layer 305, such that the innermost portion of each section of the pre-use layer 305 need not be fully removed from the top surface 306.

Figure 20:
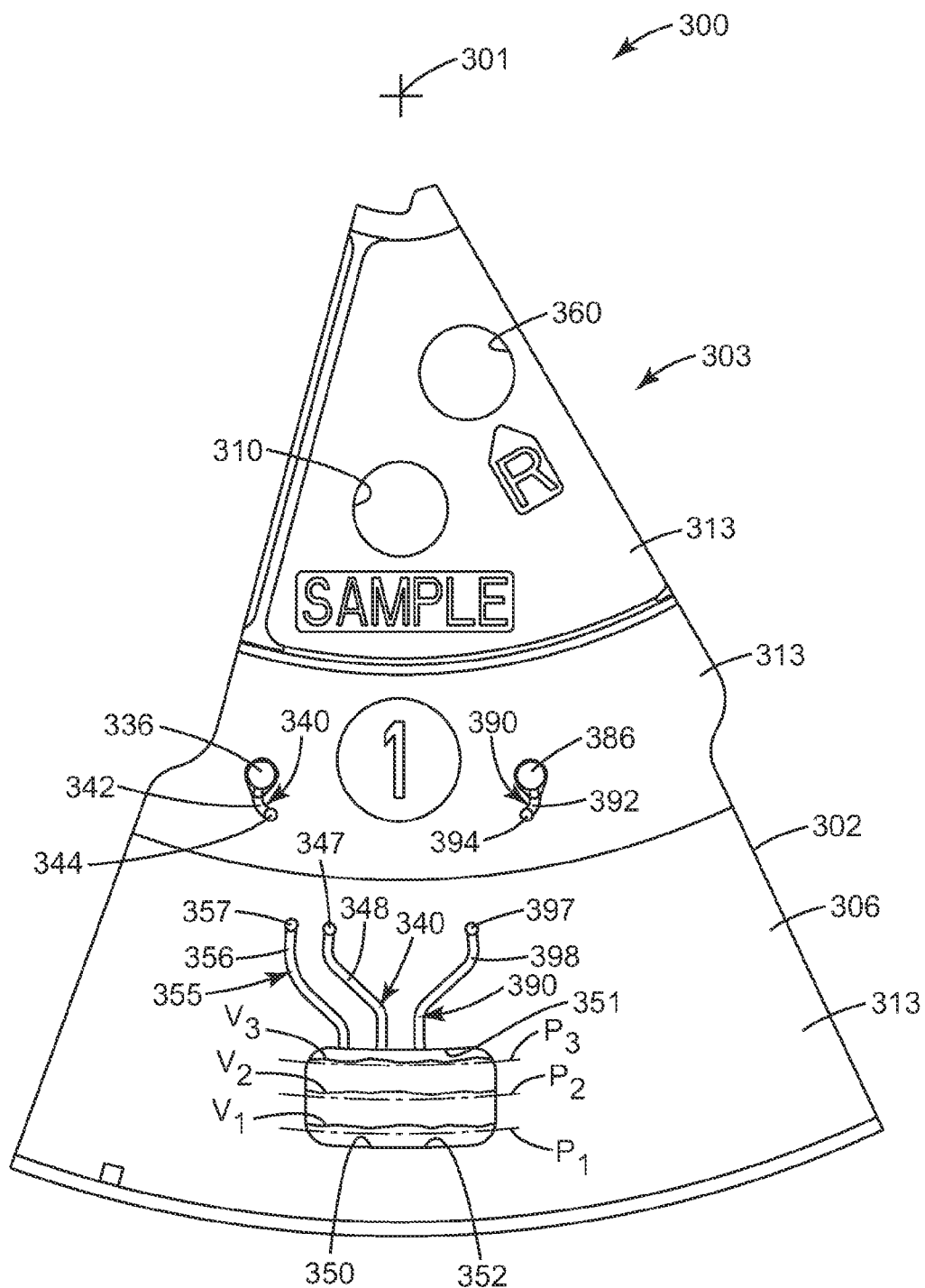
FIG. 20 is a close-up top plan view of a portion of the sample processing device of FIGS. 16-19.
Figure 21:
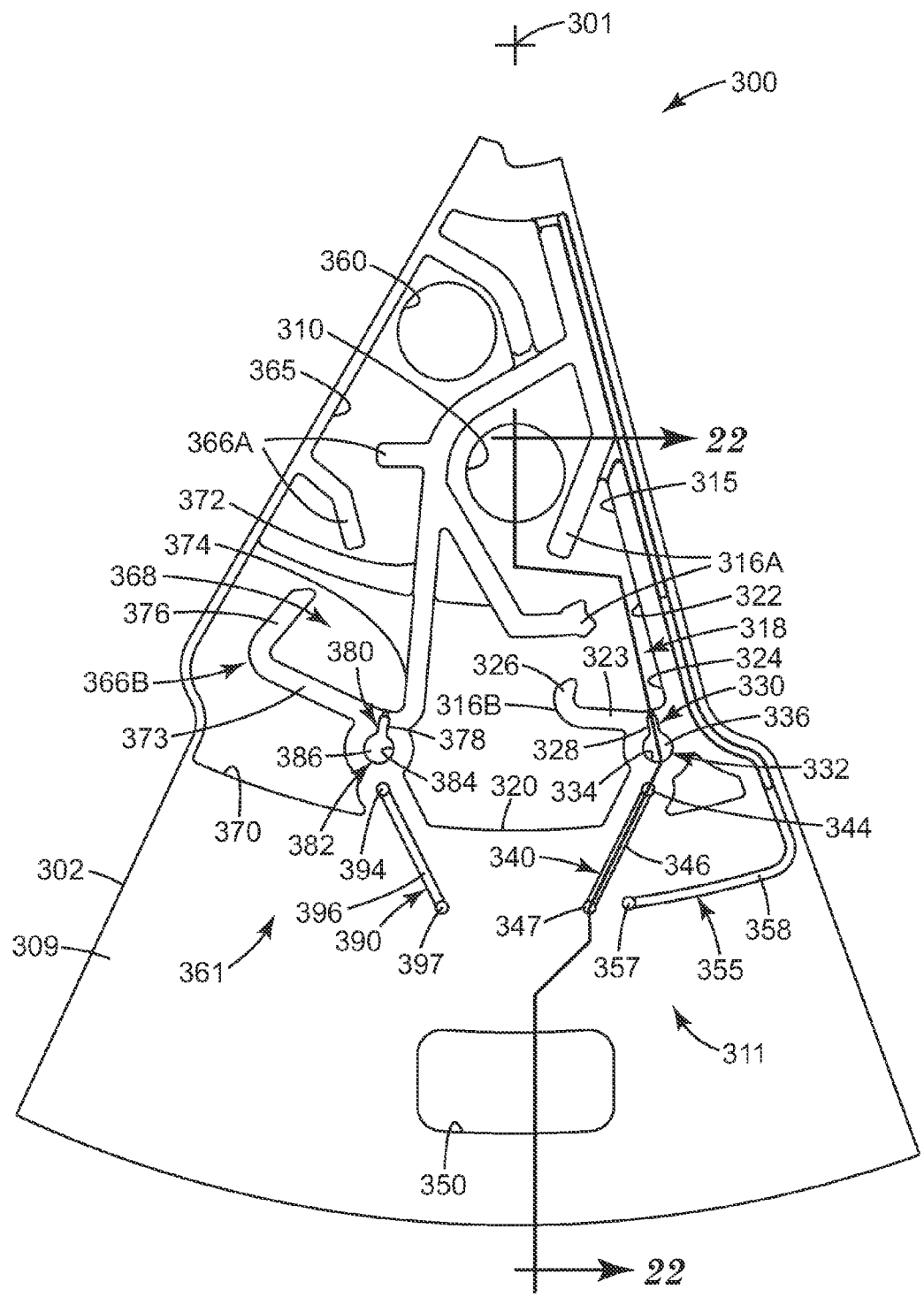
FIG. 21 is a close-up bottom plan view of the portion of the sample processing device shown in FIG. 20.

As shown in FIGS. 17, 19 and 21, in the illustrated embodiment of FIGS. 16-22, each lane 303 of the sample processing device 300 includes a sample handling portion or side 311 of the lane 303 and a reagent handling portion or side 361 of the lane 303, and the sample handling portion 311 and the reagent handling portion 361 can be fluidly isolated from one another, until the two sides are brought into fluid communication with one another, for example, by opening one or more valves, as described below. Each lane 303 can sometimes be referred to as a "distribution system" or "processing array," or in some embodiments, each side 311, 361 of the lane 303 can be referred to as a "distribution system" or "processing array." Generally, however, a "processing array" refers to an input chamber, a detection chamber, and any fluid connections therebetween.

With reference to FIGS. 17, 19 and 21, the first input aperture 310 opens into an input well or chamber 315. A similar input chamber 365 is located on the reagent handling side 361 of the lane 303 into which the second input aperture 360 opens. The separate sample and reagent input apertures 310 and 360, input chambers 315 and 365, and handling sides 311 and 361 of each lane 303 allow for raw, unprocessed samples to be loaded onto the sample processing device 300 for analysis without requiring substantial, or any, pre-processing, diluting, measuring, mixing, or the like. As such, the sample and/or the reagent can be added without precise measurement or processing. As a result, the sample processing device 300 can sometimes be referred to as a "moderate complexity" disk, because relatively complex "on-board" processing can be performed on the sample processing device 300 without requiring much or any pre-processing. That is, the sample processing device 300 can include on-board metering structures that can be used to deliver a selected volume of a sample and/or a reagent medium from an input chamber 315, 365 to a detection chamber 350. By delivering the selected volumes to the detection chamber 350, the desired ratios of sample to reagent can be achieved, without requiring a user to precisely measure and load specific volumes of sample or reagent onto the sample processing device 300. Rather, the user can load a nonspecific amount of sample and/or reagent onto the sample processing device 300, and the sample processing device 300 can itself meter a desired amount of the materials to the detection chamber 350. The sample handling side 311 will be described first.

As shown, in some embodiments, the input chamber 315 can include one or more baffles or walls 316 or other suitable fluid directing structures that are positioned to divide the input chamber 315 into at least a metering portion, chamber, or reservoir 318 and a waste portion, chamber or reservoir 320. The baffles 316 can function to direct and/or contain fluid in the input chamber 315.

As shown in the illustrated embodiment, a sample can be loaded onto the sample processing device 300 into one or more lanes 303 via the input aperture 310. As the sample processing device 300 is rotated about the axis of rotation A-A, the sample would then be directed (e.g., by the one or more baffles 316) to the metering reservoir 318. The metering reservoir 318 is configured to retain or hold a selected volume of a material, any excess being directed to the waste reservoir 320. In some embodiments, the input chamber 315, or a portion thereof, can be referred to as a "first chamber" or a "first process chamber," and the detection chamber 350 can be referred to as a "second chamber" or a "second process chamber."

As shown in FIGS. 21 and 22, the metering reservoir 318 includes a first end 322 positioned toward the center 301 of the sample processing device 300 and the axis of rotation A-A, and a second end 324 positioned away from the center 301 and the axis of rotation A-A (i.e., radially outwardly of the first end 322), such that as the sample processing device 300 is rotated, the sample is forced toward the second end 324 of the metering reservoir 318. The one or more baffles or walls 316 defining the second end 324 of the metering reservoir 318 can include a base 323 and a sidewall 326 (e.g., a partial sidewall; see FIG. 21) that are arranged to define a selected volume. The sidewall 326 is arranged and shaped to allow any volume in excess of the selected volume to overflow the sidewall 326 and run off into the waste reservoir 320. As a result, at least a portion of the waste reservoir 320 can be positioned radially outwardly of the metering reservoir 318 or of the remainder of the input chamber 315, to facilitate moving the excess volume of material into the waste reservoir 320 and inhibit the excess volume from moving back into the metering reservoir 318 under a radially-outwardly-directed force (e.g., while the sample processing device 300 is rotated about the axis of rotation A-A).

In other words, with continued reference to FIG. 21, the input chamber 315 can include one or more first baffles 316A that are positioned to direct material from the input aperture 310 toward the metering reservoir 318, and one or more second baffles 316B that are positioned to contain fluid of a selected volume and/or direct fluid in excess of the selected volume into the waste reservoir 320.

As shown, the base 323 can include an opening or fluid pathway 328 formed therein that can be configured to four at least a portion of a capillary valve 330. As a result, the cross-sectional area of the fluid pathway 328 can be small enough relative to the metering reservoir 318 (or the volume of fluid retained in the metering reservoir 318) that fluid is inhibited from flowing into the fluid pathway 328 due to capillary forces. As a result, in some embodiments, the fluid pathway 328 can be referred to as a "constriction" or "constricted pathway."

In some embodiments, the metering reservoir 318, the waste reservoir 320, one or more of the baffles 316 (e.g., the base 323, the sidewall 326, and optionally one or more first baffles 316A), and the fluid pathway 328 (or the capillary valve 330) can together be referred to as a "metering structure" responsible for containing a selected volume of material, for example, that can be delivered to downstream fluid structures when desired.

By way of example only, when the sample processing device 300 is rotated about the axis of rotation A-A at a first speed (e.g., angular velocity, RPM), a first centrifugal force is exerted on material in the sample processing device 300. The metering reservoir 318 and the fluid pathway 328 can be configured (e.g., in terms of surface energies, relative dimensions and cross-sectional areas, etc.) such that the first centrifugal force is insufficient to cause the sample of a given surface tension to be forced into the relatively narrow fluid pathway 328. However, when the sample processing device 300 is rotated at a second speed (e.g., angular velocity, RPM), a second centrifugal force is exerted on material in the sample processing device 300. The metering reservoir 318 and the fluid pathway 328 can be configured such that the second centrifugal force is sufficient to cause the sample of a given surface tension to be forced into the fluid pathway 328. Alternatively, additives (e.g., surfactants) could be added to the sample to alter its surface tension to cause the sample to flow into the fluid pathway 328 when desired. In some embodiments, the first and second forces can be at least partially controlled by controlling the acceleration profiles and speeds at which the sample processing device 300 is rotated at different processing stages. Such speeds and accelerations are described in greater detail with respect to FIG. 26.

In some embodiments, the aspect ratio of a cross-sectional area of the fluid pathway 328 relative to a volume of the input chamber 315 (or a portion thereof, such as the metering reservoir 318) can be controlled to at least partially ensure that fluid will not flow into the fluid pathway 328 until desired, e.g., for a fluid of a given surface tension.

For example, in some embodiments, the ratio of the cross-sectional area of the fluid pathway ($A_p$) (e.g., at the inlet of the fluid pathway 328 at the base 323 of the metering reservoir 318) to the volume (V) of the reservoir (e.g., the input chamber 315, or a portion thereof, such as the metering reservoir 318) from which fluid may move into the fluid pathway 328, i.e., $A_p$: V, can range from about 1:25 to about 1:500, in some embodiments, can range from about 1:50 to about 1:300, and in some embodiments, can range from about 1:100 to about 1:200. Said another way, in some embodiments, the fraction of $A_p/V$ can be at least about 0.01, in some embodiments, at least about 0.02, and in some embodiments, at least about 0.04. In some embodiments, the fraction of $A_p/V$ can be no greater than about 0.005, in some embodiments, no greater than about 0.003, and in some embodiments, no greater than about 0.002. Reported in yet another way, in some embodiments, the fraction of $V/A_p$, or the ratio of V to $A_p$, can be at least about 25 (i.e., 25 to 1), in some embodiments, at least about 50 (i.e., about 50 to 1), and in some embodiments, at least about 100 (i.e., about 100 to 1). In some embodiments, the fraction of $V/A_p$, or the ratio of V to $A_p$, can be no greater than about 500 (i.e., about 500 to 1), in some embodiments, no greater than about 300 (i.e., about 300 to 1), and in some embodiments, no greater than about 200 (i.e., about 200 to 1).

In some embodiments, these ratios can be achieved by employing various dimension in the fluid pathway 328. For example, in some embodiments, the fluid pathway 328 can have a transverse dimension (e.g., perpendicular to its length along a radius from the center 101, such as a diameter, a width, a depth, a thickness, etc.) of no greater than about 0.5 mm, in some embodiments, no greater than about 0.25 mm, and in some embodiments, no greater that about 0.1 mm. In some embodiments, the cross-sectional area 4, fluid pathway 328 can be no greater than about 0.1 mm$^2$, in some embodiments, no greater than about 0.075 mm$^2$, and in some embodiments, no greater than about 0.5 mm$^2$. In some embodiments, the fluid pathway 328 can have a length of at least about 0.1 mm, in some embodiments, at least about 0.5 mm, and in some embodiments, at least about 1 mm. In some embodiments, the fluid pathway 328 can have a length of no greater than about 0.5 mm, in some embodiments, no greater than about 0.25 mm, and in some embodiments, no greater than about 0.1 mm. In some embodiments, for example, the fluid pathway 328 can have a width of about 0.25 mm, a depth of about 0.25 mm (i.e., a cross-sectional area of about 0.0625 mm$^2$) and a length of about 0.25 mm.

As shown in the FIGS. 17, 19, 21 and 22, the capillary valve 330 can be located in fluid communication with the second end 324 of the metering reservoir 318, such that the fluid pathway 328 is positioned radially outwardly of the metering reservoir 318, relative to the axis of rotation A-A. The capillary valve 330 can be configured to inhibit fluid (i.e., liquid) from moving from the metering reservoir 318 into the fluid pathway 328, depending on at least one of the dimensions of the fluid pathway 328, the surface energy of the surfaces defining the metering reservoir 318 and/or the fluid pathway 328, the surface tension of the fluid, the force exerted on the fluid, any backpressure that may exist (e.g., as a result of a vapor lock formed downstream, as described below), and combinations thereof. As a result, the fluid pathway 328 (e.g., the constriction) can be configured (e.g., dimensioned) to inhibit fluid from entering the valve chamber 334 until a force exerted on the fluid (e.g., by rotation of the sample processing device 300 about the axis of rotation A-A), the surface tension of the fluid, and/or the surface energy of the fluid pathway 328 are sufficient to move the fluid past the fluid pathway 328.

As shown in the illustrated embodiment, the capillary valve 330 can be arranged in series with a septum valve 332, such that the capillary valve 330 is positioned radially inwardly of the septum valve 332 and in fluid communication with an inlet of the septum valve 332. The septum valve 332 can include a valve chamber 334 and a valve septum 336. In a given orientation (e.g., substantially horizontal) on a rotating platform, the capillary force can be balanced and offset by centrifugal to control fluid flow. The septum valve 332 (also sometimes referred to as a "phase-change-type valve") can be receptive to a heat source (e.g., electromagnetic energy) that can cause melting of the valve septum 336 to open a pathway through the valve septum 336.

The septum 336 can be located between the valve chamber 334 and one or more downstream fluid structures in the sample processing device 300. As such, the detection chamber 350 can be in fluid communication with an outlet of the septum valve 332 (i.e., the valve chamber 334) and can be positioned at least partially radially outwardly of the valve chamber 334, relative to the axis of rotation A-A and the center 301. The septum 336 can include (i) a closed configuration wherein the septum 336 is impermeable to fluids (and particularly, liquids), and positioned to fluidly isolate the valve chamber 334 from any downstream fluid structures; and (ii) an open configuration wherein the septum 336 is permeable to fluids, particularly, liquids (e.g., includes one or more openings sized to encourage the sample to flow therethrough) and allows fluid communication between the valve chamber 334 and any downstream fluid structures. That is, the valve septum 336 can prevent fluids (i.e., liquids) from moving between the valve chamber 334 and any downstream fluid structures when it is intact.

Various features and details of the valving structure and process are described in U.S. Patent Application Nos. 61/487,669, filed May 18, 2011, and 61/490,012, filed May 25, 2011, each of which is incorporated herein by reference in its entirety.

The valve septum 336 can include or be formed of an impermeable barrier that is opaque or absorptive to electromagnetic energy, such as electromagnetic energy in the visible, infrared and/or ultraviolet spectrums. As used in connection with the present disclosure, the term "electromagnetic energy" (and variations thereof) means electromagnetic energy (regardless of the wavelength/frequency) capable of being delivered from a source to a desired location or material in the absence of physical contact. Nonlimiting examples of electromagnetic energy include laser energy, radio-frequency (RF), microwave radiation, light energy (including the ultraviolet through infrared spectrum), etc. In some embodiments, electromagnetic energy can be limited to energy falling within the spectrum of ultraviolet to infrared radiation (including the visible spectrum).

The valve septum 336, or a portion thereof, may be distinct from the substrate 302 (e.g., made of a material that is different than the material used for the substrate 302). By using different materials for the substrate 302 and the valve septum 336, each material can be selected for its desired characteristics. Alternatively, the valve septum 336 may be integral with the substrate 302 and made of the same material as the substrate 302. For example, the valve septum 336 may simply be molded into the substrate 302. If so, it may be coated or impregnated to enhance its ability to absorb electromagnetic energy.

The valve septum 336 may be made of any suitable material, although it may be particularly useful if the material of the septum 336 forms voids (i.e., when the septum 336 is opened) without the production of any significant byproducts, waste, etc. that could interfere with the reactions or processes taking place in the sample processing device 300. One example of a class of materials that can be used as the valve septum 336, or a portion thereof, include pigmented oriented polymeric films, such as, for example, films used to manufacture commercially available can liners or bags. A suitable film may be a black can liner, 1.18 mils thick, available from Himolene Incorporated, of Danbury, Conn. under the designation 406230E. However, in some embodiments, the septum 336 can be formed of the same material as the substrate 302 itself, but may have a smaller thickness than other portions of the substrate 302. The septum thickness can be controlled by the mold or tool used to form the substrate 302, such that the septum is thin enough to sufficiently be opened by absorbing energy from an electromagnetic signal.

In some embodiments, the valve septum 336 can have a cross-sectional area of at least about 1 mm$^2$, in some embodiments, at least about 2 mm$^2$, and in some embodiments, at least about 5 mm$^2$. In some embodiments, the valve septum 336 can have a cross-sectional area of no greater than about 10 mm$^2$, in some embodiments, no greater than about 8 mm$^2$, and in some embodiments, no greater than about 6 mm$^2$.

In some embodiments, the valve septum 336 can have a thickness of at least about 0.1 min, in some embodiments, at least about 0.25 mm, and in some embodiments, at least about 0.4 mm. In some embodiments, the valve septum 336 can have a thickness of no greater than about 1 mm, in some embodiments, no greater than about 0.75 mm, and in some embodiments, no greater than about 0.5 mm.

In some embodiments, the valve septum 336 can be generally circular in shape, can have a diameter of about 1.5 mm (i.e., a cross-sectional area of about 5.3 mm$^2$), and a thickness of about 0.4 mm.

In some embodiments, the valve septum 336 can include material susceptible of absorbing electromagnetic energy of selected wavelengths and converting that energy to heat, resulting in the formation of a void in the valve septum 336. The absorptive material may be contained within the valve septum 336, or a portion thereof (e.g., impregnated in the material (resin) forming the septum), or coated on a surface thereof. For example, as shown in. FIG. 20, the valve septum 336 can be configured to be irradiated with electromagnetic energy from the top (i.e., at the top surface 306 of the substrate 302). As a result, the first layer 304 over the valve septum region (see FIG. 16) can be transparent to the selected wavelength, or range of wavelengths, of electromagnetic energy used to create a void in the valve septum 336, and the valve septum 336 can be absorptive of such wavelength(s).

The capillary valve 330 is shown in the embodiment illustrated in FIGS. 16-22 as being in series with the septum valve 332, and particularly, as being upstream of and in fluid communication with an inlet or upstream end of the septum valve 332. Such a configuration of the capillary valve 330 and the septum valve 332 can create a vapor lock (i.e., in the valve chamber 334) when the valve septum 336 is in the closed configuration and a sample is moved and pressures are allowed to develop in the sample processing device 300. Such a configuration can also allow a user to control when fluid (i.e., liquid) is permitted to enter the valve chamber 334 and collect adjacent the valve septum 336 (e.g., by controlling the speed at which the sample processing device 300 is rotated, which affects the centrifugal force exerted on the sample, e.g., when the surface tension of the sample remains constant; and/or by controlling the surface tension of the sample). That is, the capillary valve 330 can inhibit fluid (i.e., liquids) from entering the valve chamber 334 and pooling or collecting adjacent the valve septum 336 prior to opening the septum valve 332, i.e., when the valve septum 336 is in the closed configuration.

The capillary valve 330 and the septum valve 332 can together, or separately, be referred to as a "valve" or "valving structure" of the sample processing device 300. That is, the valving structure of the sample processing device 300 is generally described above as including a capillary valve and a septum valve; however, it should be understood that in some embodiments, the valve or valving structure of the sample processing device 300 can simply be described as including the fluid pathway 328, the valve chamber 334, and the valve septum 336. Furthermore, in some embodiments, the fluid pathway 328 can be described as forming a portion of the input chamber 315 (e.g., as forming a portion of the metering reservoir 318), such that the downstream end 324 includes a fluid pathway 328 that is configured to inhibit fluid from entering the valve chamber 334 until desired.

By inhibiting fluid (i.e., liquid) from collecting adjacent one side of the valve septum 336, the valve septum 336 can be opened, i.e., changed form a closed configuration to an open configuration, without the interference of other matter. For example, in some embodiments, the valve septum 336 can be opened by forming a void in the valve septum 336 by directing electromagnetic energy of a suitable wavelength at one side of the valve septum 336 (e.g., at the top surface 306 of the sample processing device 300). The present inventors discovered that, in some cases, if liquid has collected on the opposite side of the valve septum 336, the liquid may interfere with the void forming (e.g., melting) process by functioning as a heat sink for the electromagnetic energy, which can increase the power and/or time necessary to form a void in the valve septum 336. As a result, by inhibiting fluid (i.e., liquid) from collecting adjacent one side of the valve septum 336, the valve septum 336 can be opened by directing electromagnetic energy at a first side of the valve septum 336 when no fluid (e.g., a liquid, such as a sample or reagent) is present on a second side of the valve septum 336. By inhibiting fluid (e.g., liquid) from collecting on the back side of the valve septum 336, the septum valve 332 can be reliably opened across a variety of valving conditions, such as laser power (e.g., 440, 560, 670, 780, and 890 milliwatts (mW)), laser pulse width or duration (e.g., 1 or 2 seconds), and number of laser pulses (e.g., 1 or 2 pulses).

As a result, the capillary valve 330 functions to (i) effectively form a closed end of the metering reservoir 318 so that a selected volume of a sample can be metered and delivered to the downstream detection chamber 350, and (ii) effectively inhibit fluids (e.g., liquids) from collecting adjacent one side of the valve septum 336 when the valve septum 336 is in its closed configuration, for example, by creating a vapor lock in the valve chamber 334.

In some embodiments, the valving structure can include a longitudinal direction oriented substantially radially relative to the center 301 of the sample processing device 300. In some embodiments, the valve septum 336 can include a length that extends in the longitudinal direction greater than the dimensions of one or more openings or voids that may be formed in the valve septum 336, such that one or more openings can be formed along the length of the valve septum 336 as desired. That is, in some embodiments, it may be possible to remove selected aliquots of a sample by forming openings at selected locations along the length in the valve septum 336. The selected aliquot volume can be determined based on the radial distance between the openings (e.g., measured relative to the axis of rotation A-A) and the cross-sectional area of the valve chamber 334 between openings. Other embodiments and details of such a "variable valve" can be found in U.S. Pat. No. 7,322,254 and U.S. Patent Application Publication No. 2010/0167304.

After an opening or void has been formed in the valve septum 336, the valve chamber 334 becomes in fluid communication with downstream fluid structures, such as the detection chamber 350, via the void in the valve septum 336.

As mentioned above, after a sample has been loaded into the sample handling side 311 of the lane 303, the first input aperture 310 can be closed, sealed and/or plugged. As such, the sample processing device 300 can be sealed from ambience or "unvented" during processing.

As used in connection with the present disclosure, an "unvented processing array" or "unvented distribution system" is a distribution system (i.e., "process chamber array," "processing array," or "lane" 303) in which the only openings leading into the volume of the fluid structures therein are located in the input chamber 315 for the sample (or the input chamber 365 for the reagent). In other words, to reach the detection chamber 350 within an unvented distribution system, sample (and/or reagent) materials are delivered to the input chamber 315 (or the input chamber 365), and the input chamber 315 is subsequently sealed from ambience. As shown in FIGS. 16-22, such an unvented distribution system may include one or more dedicated channels to deliver the sample materials to the detection chamber 350 (e.g., in a downstream direction) and one or more dedicated channels to allow air or another fluid to exit the detection chamber 350 via a separate path than that in which the sample is moving. In contrast, a vented distribution system would be open to ambience during processing and would also likely include air vents positioned in one or more locations along the distribution system, such as in proximity to the detection chamber 350. As mentioned above, an unvented distribution system inhibits contamination between an environment and the interior of the sample processing device 300 (e.g., leakage from the sample processing device 300, or the introduction of contaminants from an environment or user into the sample processing device 300), and also inhibits cross-contamination between multiple samples or lanes 303 on one sample processing device 300.

As shown in FIGS. 17, 19, and 21, to facilitate fluid flow in the sample processing device 300 during processing, the lane 303 can include one or more equilibrium channels 355 positioned to fluidly couple a downstream or radially outward portion of the lane 303 (e.g., the detection chamber 350) with one or more fluid structures that are upstream or radially inward of the detection chamber 350 (e.g., at least a portion of the input chamber 315, at least a portion of the input chamber 365 on the reagent handling side 361, or both).

By way of example only, each lane 303 of the illustrated sample processing device 300, as shown in FIGS. 20 and 21, includes an equilibrium channel 355 positioned to fluidly couple the detection chamber 350 with an upstream, or radially inward (i.e., relative to the center 301) portion of the reagent input chamber 365 on the reagent handling side 361 of the lane 303. The equilibrium channel 355 is an additional channel that allows for upstream movement of fluid (e.g., gases, such as trapped air) from otherwise vapor locked downstream portions of the fluid structures to facilitate the downstream movement of other fluid (e.g., a sample material, liquids, etc.) into those otherwise vapor locked regions of the sample processing device 300. Such an equilibrium channel 355 allows the fluid structures on the sample processing device 300 to remain unvented or closed to ambience during sample processing, i.e., during fluid movement on the sample processing device 300. As a result, in some embodiments, the equilibrium channel 355 can be referred to as an "internal vent" or a "vent channel," and the process of releasing trapped fluid to facilitate material movement can be referred to as "internally venting."

Said another way, in some embodiments, the flow of a sample (or reagent) from an input chamber 315 (or the reagent input chamber 365) to the detection chamber 350 can define a first direction of movement, and the equilibrium channel 355 can define a second direction of movement that is different from the first direction. Particularly, the second direction is opposite, or substantially opposite, the first direction. When a sample (or reagent) is moved to the detection chamber 350 via a force (e.g., centrifugal force), the first direction can be oriented generally along the direction of force, and the second direction can be oriented generally opposite the direction of force.

When the valve septum 336 is changed to the open configuration (e.g., by emitting electromagnetic energy at the septum 336), the vapor lock in the valve chamber 334 can be released, at least partly because of the equilibrium channel 355 connecting the downstream side of the septum 336 back up to the input chamber 365. The release of the vapor lock can allow fluid (e.g., liquid) to flow into the fluid pathway 328, into the valve chamber 334, and to the detection chamber 350. In some embodiments, this phenomenon can be facilitated when the channels and chambers are hydrophobic, or generally defined by hydrophobic surfaces. This is, in some embodiments, the substrate 302 and any covers or layers 304, 305, and 308 (or adhesives coated thereon, for example, comprising silicone polyurea) that at least partially define the channel and chambers can be formed of hydrophobic materials or include hydrophobic surfaces, particularly, as compared to aqueous samples and/or reagent materials.

In some embodiments, hydrophobicity of a material surface can be determined by measuring the contact angle between a droplet of a liquid of interest and the surface of interest. In the present case, such measurements can be made between various sample and/or reagent materials and a material that would be used in forming at least some surface of a sample processing device that would come into contact with the sample and/or reagent. In some embodiments, the sample and/or reagent materials can be aqueous liquids (e.g., suspensions, or the like). In some embodiments, the contact angle between a sample and/or reagent of the present disclosure and a substrate material forming at least a portion of the sample processing device 300 can be at least about 70°, in some embodiments, at least about 75°, in some embodiments, at least about 80°, in some embodiments, at least about 90°, in some embodiments, at least about 95°, and in some embodiments, at least about 99°.

In some embodiments, fluid can flow into the fluid pathway 328 when a sufficient force has been exerted on the fluid (e.g., when a threshold force on the fluid has been achieved, e.g., when the rotation of the sample processing device 300 about the axis of rotation A-A has exceeded a threshold acceleration or rotational acceleration). After the fluid has overcome the capillary forces in the capillary valve 330, the fluid can flow through the open valve septum 336 to downstream fluid structures (e.g., the detection chamber 350).

As discussed throughout the present disclosure, the surface tension of the sample and/or reagent material being moved through the sample processing device 300 can affect the amount of force needed to move that material into the fluid pathway 328 and to overcome the capillary forces. Generally, the lower the surface tension of the material being moved through the sample processing device 300, the lower the force exerted on the material needs to be in order to overcome the capillary forces. In some embodiments, the surface tension of the sample and/or reagent material can be at least about 40 mN/m, in some embodiments, at least about 43 mN/m, in some embodiments, at least about 45 mN/m, in some embodiments, at least about 50 mN/m, in some embodiments, at least about 54 mN/m. In some embodiments, the surface tension can be no greater than about 80 nM/m, in some embodiments, no greater than about 75 mN/m, in some embodiments, no greater than about 72 mN/m, in some embodiments, no greater than about 70 mN/m, and in some embodiments, no greater than about 60 mN/m.

In some embodiments, the density of the sample and/or reagent material being moved through the sample processing device 300 can be at least about 1.00 g/mL, in some embodiments, at least about 1.02 g/mL, in some embodiments, at least about 1.04 g/mL. In some embodiments, the density can be no greater than about 1.08 g/mL, in some embodiments, no greater than about 1.06 g/mL, and in some embodiments, no greater than about 1.05 g/mL.

In some embodiments, the viscosity of the sample and/or reagent material being moved through the sample processing device can be at least about 1 centipoise (nMs/m$^2$), in some embodiments, at least about 1.5 centipoise, and in some embodiments, at least about 1.75 centipoise. In some embodiments, the viscosity can be no greater than about 2.5 centipoise, in some embodiments, no greater than about 2.25 centipoise, and in some embodiments, no greater than about 2.00 centipoise. In some embodiments, the viscosity can be 1.0019 centipoise or 2.089 centipoise.

The following table includes various data for aqueous media that can be employed in the present disclosure, either as sample diluents and/or reagents. One example is a Copan Universal Transport Media ("UTM") for Viruses, *Chlamydia*, *Mycoplasma*, and *Ureaplasma*, 3.0 mL tube, part number 330C, lot 39P505 (Copan Diagnostics, Murrietta, Ga.). This UTM is used as the sample in the Examples. Another example is a reagent master mix ("Reagent"), available from Focus Diagnostics (Cypress, Calif.). Viscosity and density data for water at 25° C. and 25% glycerol in water are included in the following table, because some sample and/or reagent materials of the present disclosure can have material properties ranging from that of water to that of 25% glycerol in water, inclusive. The contact angle measurements in the following table were measured on a black polypropylene, which was formed by combining, at the press, Product No. P4G3Z-039 Polypropylene, natural, from Flint Hills Resources (Wichita, Kans.) with Clariant Colorant UN0055P, Deep Black (carbon black), 3% LDR, available from Clariant Corporation (Muttenz, Switzerland). Such a black polypropylene can be used in some embodiments to form at least a portion (e.g., the substrate 302) of a sample processing device of the present disclosure (e.g., the sample processing device 300).

| Medium | Contact angle (degrees °) | Surface Tension (mN/m) | Viscosity (centipoise) | Density (g/mL) |
| --- | --- | --- | --- | --- |
| UTM | 99 | 54 | — | 1.02 |
| Reagent | 71 | 43 | — | 1.022 |
| Water at 25° C. | — | 72 | 1.0019 | 1.00 |
| 25% glycerol in water | — | — | 2.089 | 1.061 |

Moving sample material within sample processing devices that include unvented distribution systems may be facilitated by alternately accelerating and decelerating the device during rotation, essentially burping the sample materials through the various channels and chambers. The rotating may be performed using at least two acceleration/ deceleration cycles, i.e., an initial acceleration, followed by deceleration, second round of acceleration, and second round of deceleration.

The acceleration/deceleration cycles may not be necessary in embodiments of processing devices (e.g., the sample processing device 300) that include distribution systems with equilibrium channels such as the equilibrium channel 355. The equilibrium channel 355 may help prevent air or other fluids from interfering with the flow of the sample materials through the fluid structures. The equilibrium channel 355 may provide paths for displaced air or other fluids to exit the detection chamber 350 to equilibrate the pressure within the distribution system, which may minimize the need for the acceleration and/or deceleration to "burp" the distribution system. However, the acceleration and/or deceleration technique may still be used to further facilitate the distribution of sample materials through an unvented distribution system. The acceleration and/or deceleration technique may also be useful to assist in moving fluids over and/or around irregular surfaces such as rough edges created by EM induced valving, imperfect molded channels/chambers, etc.

It may further be helpful if the acceleration and/or deceleration are rapid. In some embodiments, the rotation may only be in one direction, i.e., it may not be necessary to reverse the direction of rotation during the loading process. Such a loading process allows sample materials to displace the air in those portions of the system that are located farther from the center 301 of rotation of the sample processing device 300 than the opening(s) into the system.

The actual acceleration and deceleration rates may vary based on a variety of factors such as temperature, size of the device, distance of the sample material from the axis of rotation, materials used to manufacture the devices, properties of the sample materials (e.g., viscosity), etc. One example of a useful acceleration/deceleration process may include an initial acceleration to about 4000 revolutions per minute (rpm), followed by deceleration to about 1000 rpm over a period of about 1 second, with oscillations in rotational speed of the device between 1000 rpm and 4000 rpm at 1 second intervals until the sample materials have traveled the desired distance.

Another example of a useful loading process may include an initial acceleration of at least about 20 revolutions/sec$^2$ to first rotational speed of about 500 rpm, followed by a 5-second hold at the first rotational speed, followed by a second acceleration of at least about 20 revolutions/sec$^2$ to a second rotational speed of about 1000 rpm, followed by a 5-second hold at the second rotational speed. Another example of a useful loading process may include an initial acceleration of at least about 20 revolutions/sec$^2$ to a rotational speed of about 1800 rpm, followed by a 10-second hold at that rotational speed.

As shown in FIGS. 20 and 21, the equilibrium channel 355 can be formed of a series of channels on the top surface 306 and/or the bottom surface 309 of the substrate 302, and one or more vias that extend between the top surface 306 and the bottom surface 309, which can aid in traversing stepped portions in the top surface 306 of the substrate 302. Specifically, as shown in FIG. 20, the illustrated equilibrium channel 355 includes a first channel or portion 356 that extends along the top surface 306 of an outermost step 313; a first via 357 extending from the top surface 306 to the bottom surface 309 to avoid the equilibrium channel 355 having to traverse the stepped portion of the top surface 306; and a second channel or portion 358 (see FIG. 21) that extends to a radially inward portion of the input chamber 365.

Air or another fluid within the detection chamber 350 may be displaced when the detection chamber 350 receives a sample material or other material. The equilibrium channel 355 may provide a path for the displaced air or other displaced fluid to pass out of the detection chamber 350. The equilibrium channel 355 may assist in more efficient movement of fluid through the sample processing device 300 by equilibrating the pressure within each distribution system of the sample processing device 300 (e.g., the input chamber 315 and the detection chamber 350, and the various channels connecting the input chamber 315 and the detection chamber 350) by enabling some channels of the distribution system to be dedicated to the flow of a fluid in one direction (e.g., an upstream or downstream direction). In the embodiment illustrated in FIGS. 16-22, the sample generally flows downstream and radially outwardly (e.g., when the sample processing device 300 is rotated about the center 301) from the input chamber 315, through the capillary valve 330 and the septum valve 332, and through the distribution channel 340, to the detection chamber 350. Other fluid (e.g., gases present in the detection chamber 350) can generally flow upstream or radially inwardly, i.e., generally opposite that of the direction of sample movement, from the detection chamber 350, through the equilibrium channel 355, to the input chamber 365.

Returning to the valving structure, the downstream side of the valve septum 336 (i.e., which faces the top surface 306 of the illustrated sample processing device 300; see FIGS. 20 and 22) faces and eventually opens into (e.g., after an opening or void is formed in the valve septum 336) a distribution channel 340 that fluidly couples the valve chamber 334 (and ultimately, the input chamber 315 and particularly, the metering reservoir 318) and the detection chamber 350. Similar to the equilibrium channel 355, the distribution channel 340 can be formed of a series of channels on the top surface 306 and/or the bottom surface 309 of the substrate 302 and one or more vias that extend between the top surface 306 and the bottom surface 309, which can aid in traversing stepped portions in the top surface 306 of the substrate 302. For example, as shown in FIGS. 20-22, in some embodiments, the distribution channel 340 can include a first channel or portion 342 (see FIGS. 20 and 22) that extends along the top surface 306 of the middle step 313 of the substrate 302; a first via 344 (see FIGS. 20-22) that extends from the top surface 306 to the bottom surface 309; a second channel or portion 346 (see FIGS. 21 and 22) that extends along the bottom surface 309 to avoid traversing the stepped top surface 306; a second via 347 (see FIGS. 20-22) that extends from the bottom surface 309 to the top surface 306, and a third channel or portion 348 (see FIGS. 20 and 22) that extends along the top surface 306 and empties into the detection chamber 350.

All layers and covers are removed from the sample processing device 300 in FIGS. 18-22 for simplicity, such that the substrate 302 alone is shown; however, it should be understood that any channels and chambers formed on the bottom surface 309 can also be at least partially defined by the second layer(s) 308, and that any channels and chambers formed on the top surface 306 can also be at least partially defined by the first layer(s) 304, as shown in FIGS. 16-17.

Force can be exerted on a sample to cause it to move from the input chamber 315 (i.e., the metering reservoir 318), through the fluid pathway 328, into the valve chamber 334, through a void in the valve septum 336, along the distribution channel 340, and into the detection chamber 350. As mentioned above, such force can be centrifugal force that can be generated by rotating the sample processing device 300, for example, about the axis of rotation A-A, to move the sample radially outwardly from the axis of rotation A-A (i.e., because at least a portion of the detection chamber 350 is located radially outwardly of the input chamber 315). However, such force can also be established by a pressure differential (e.g., positive and/or negative pressure), and/or gravitational force. Under an appropriate force, the sample can traverse through the various fluid structures, including the vias, to ultimately reside in the detection chamber 350. Particularly, a selected volume, as controlled by the metering reservoir 318 (i.e., and baffles 316 and waste reservoir 320), of the sample will be moved to the detection chamber 350 after the septum valve 332 is opened and a sufficient force is exerted on the sample to move the sample through the fluid pathway 328 of the capillary valve 330.

In the embodiment illustrated in FIGS. 16-22, the valve septum 336 is located between the valve chamber 334 and the detection (or process) chamber 350, and particularly, is located between the valve chamber 334 and the distribution channel 340 that leads to the detection chamber 350. While the distribution channel 340 is shown by way of example only, it should be understood that in some embodiments, the valve chamber 334 may open directly into the detection chamber 350, such that the valve septum 336 is positioned directly between the valve chamber 334 and the detection chamber 350.

The reagent handling side 361 of the lane 303 can be configured substantially similarly as that of the sample handling side 311 of the lane 303. Therefore, any details, features or alternatives thereof of the features of the sample handling side 311 described above can be extended to the features of the reagent handling side 361. As shown in FIGS. 17, 19 and 21, the reagent handling side 361 includes the second input aperture 360 which opens into the input chamber or well 365. As shown, in some embodiments, the input chamber 365 can include one or more baffles or walls 366 or other suitable fluid directing structures that are positioned to divide the input chamber 365 into at least a metering portion, chamber, or reservoir 368 and a waste portion, chamber or reservoir 370. The baffles 366 can function to direct and/or contain fluid in the input chamber 365. As shown in the illustrated embodiment, a reagent can be loaded onto the sample processing device 300 into the same lane 303 as the corresponding sample via the input aperture 360. In some embodiments, the reagent can include a complete reagent cocktail or master mix that can be loaded at the desired time for a given assay. However, in some embodiments, the reagent can include multiple portions that are loaded at different times, as needed for a particular assay. Particular advantages have been noted where the reagent is in the form of an assay cocktail or master mix, such that all enzymes, fluorescent labels, probes, and the like, that are needed for a particular assay can be loaded (e.g., by a non-expert user) at once and subsequently metered and delivered (by the sample processing device 300) to the sample when appropriate.

After the reagent is loaded onto the sample processing device 300, the sample processing device 300 can be rotated about the axis of rotation A-A, directing (e.g., by the one or more baffles 366) the reagent to the metering reservoir 368. The metering reservoir 368 is configured to retain or hold a selected volume of a material, any excess being directed to the waste reservoir 370. In some embodiments, the input chamber 365, or a portion thereof, can be referred to as a "first chamber," a "first process chamber" and the detection chamber 350 can be referred to as a "second chamber" or a "second process chamber."

As shown in FIG. 21, the metering reservoir 368 includes a first end 372 positioned toward the center 301 of the sample processing device 300 and the axis of rotation A-A, and a second end 374 positioned away from the center 301 and the axis of rotation A-A (i.e., radially outwardly of the first end 372), such that as the sample processing device 300 is rotated, the reagent is forced toward the second end 374 of the metering reservoir 368. The one or more baffles or walls 366 defining the second end 374 of the metering reservoir 368 can include a base 373 and a sidewall 376 (e.g., a partial sidewall) that are arranged to define a selected volume. The sidewall 376 is arranged and shaped to allow any volume in excess of the selected volume to overflow the sidewall 376 and run off into the waste reservoir 370. As a result, at least a portion of the waste reservoir 370 can be positioned radially outwardly of the metering reservoir 368 or of the remainder of the input chamber 365, to facilitate moving the excess volume of material into the waste reservoir 370 and inhibit the excess volume from moving back into the metering reservoir 368, as the sample processing device 300 is rotated.

In other words, with continued reference to FIG. 21, the input chamber 365 can include one or more first baffles 366A that are positioned to direct material from the input aperture 360 toward the metering reservoir 368, and one or more second baffles 366B that are positioned to contain fluid of a selected volume and/or direct fluid in excess of the selected volume into the waste reservoir 370.

As shown, the base 373 can include an opening or fluid pathway 378 formed therein that can be configured to form at least a portion of a capillary valve 180. The capillary valve 380 and metering reservoir 368 can function the same as the capillary valve 330 and the metering reservoir 318 of the sample handling side 311 of the lane 303. In addition, the fluid pathway 378 aspect ratios, and ranges thereof, can be the same as those described above with respect to the capillary valve 330.

As shown in FIGS. 17, 19 and 21, in some embodiments, the reagent metering reservoir 368 can be configured to retain a larger volume than the sample metering reservoir 318. As a result, a desired (and relatively smaller) volume of sample needed for a particular assay can be retained by the sample metering reservoir 318 and sent downstream (e.g., via the valving structure 330, 332 and distribution channel 340) to the detection chamber 350 for processing, and a desired (and relatively larger) volume of the reagent needed for a particular assay (or a step thereof) can be retained by the reagent metering reservoir 368 and sent downstream to the detection chamber 350 for processing via structures that will now be described.

Similar to the sample handling side 311, the capillary valve 380 on the reagent handling side 361 can be arranged in series with a septum valve 382. The septum valve 382 can include a valve chamber 384 and a valve septum 386. As described above with respect to the septum 336, the septum 386 can be located between the valve chamber 384 and one or more downstream fluid structures in the sample processing device 300, and the septum 386 can include a closed and an open configuration, and can prevent fluids (i.e., liquids) from moving between the valve chamber 384 and any downstream fluid structures when it is intact.

The valve septum 386 can include or be formed of any of the materials described above with respect to the valve septum 336, and can be configured and operated similarly. In some embodiments, the reagent valve septum 386 can be susceptible to a different wavelength or range of wavelengths of electromagnetic energy than the sample valve septum 336, but in some embodiments, the two valve septums 336 and 386 can be substantially the same and susceptible to the same electromagnetic energy, such that one energy source (e.g., a laser) can be used for opening all of the septum valves 330 and 380 on the sample processing device 300.

After an opening or void has been formed in the valve septum 386, the valve chamber 384 becomes in fluid communication with downstream fluid structures, such as the detection chamber 350, via the void in the valve septum 386, wherein the reagent can be combined with the sample. After a reagent has been loaded into the reagent handling side 361 of the lane 303, the second input aperture 360 can be closed, sealed and/or plugged. As such, the sample processing device 300 can be sealed from ambience or "unvented" during processing.

In the embodiment illustrated in FIGS. 16-22, the same equilibrium channel 355 can facilitate fluid movement in a downstream direction in both the sample handling side 311 and the reagent handling side 361 to assist in moving both the sample and the reagent to the detection chamber 350, which can occur simultaneously or at different times.

The downstream side of the valve septum 386 (i.e., which faces the top surface 306 of the illustrated sample processing device 300; see FIG. 20) faces and eventually opens into (e.g., after an opening or void is formed in the valve septum 336) a distribution channel 390 that fluidly couples the valve chamber 384 (and ultimately, the input chamber 365 and particularly, the metering reservoir 368) and the detection chamber 350. Similar to the equilibrium channel 355 and the sample distribution channel 340, the distribution channel 390 can be formed of a series of channels on the top surface 306 and/or the bottom surface 309 of the substrate 302, and one or more vias that extend between the top surface 306 and the bottom surface 309, which can aid in traversing stepped portions in the top surface 306 of the substrate 302. For example, as shown in FIGS. 20 and 21, in some embodiments, the distribution channel 390 can include a first channel or portion 392 (see FIG. 20) that extends along the top surface 306 of the middle step 313 of the substrate 302; a first via 394 (see FIGS. 20 and 21) that extends from the top surface 306 to the bottom surface 309; a second channel or portion 396 (see FIG. 21) that extends along the bottom surface 309 to avoid traversing the stepped top surface 306; a second via 397 (see FIGS. 20 and 21) that extends from the bottom surface 309 to the top surface 306, and a third channel or portion 398 (see FIG. 20) that extends along the top surface 306 and empties into the detection chamber 350.

Force can be exerted on a reagent to cause it to move from the input chamber 365 (i.e., the metering reservoir 368), through the fluid pathway 378, into the valve chamber 384, through a void in the valve septum 386, along the distribution channel 390, and into the detection chamber 350, where the reagent and a sample can be combined. As mentioned above, such force can be centrifugal force that can be generated by rotating the sample processing device 300, for example, about the axis of rotation A-A, but such force can also be established by a pressure differential (e.g., positive and/or negative pressure), and/or gravitational force. Under an appropriate force, the reagent can traverse through the various fluid structures, including the vias, to ultimately reside in the detection chamber 350. Particularly, a selected volume, as controlled by the metering reservoir 368 (i.e., and baffles 366 and waste reservoir 370), of the reagent will be moved to the detection chamber 350 after the septum valve 382 is opened and a sufficient force is exerted on the reagent to move the reagent through the fluid pathway 378 of the capillary valve 380.

In the embodiment illustrated in FIGS. 16-22, the valve septum 386 is located between the valve chamber 384 and the detection (or process) chamber 350, and particularly, is located between the valve chamber 384 and the distribution channel 390 that leads to the detection chamber 350. While the distribution channel 390 is shown by way of example only, it should be understood that in some embodiments, the valve chamber 384 may open directly into the detection chamber 350, such that the valve septum 386 is positioned directly between the valve chamber 384 and the detection chamber 350. In addition, in some embodiments, neither the sample distribution channel 340 nor the reagent distribution channel 390 is employed, or only one of the distribution channels 340, 390 is employed, rather than both, as illustrated in the embodiment of FIGS. 16-22.

Figure 31:
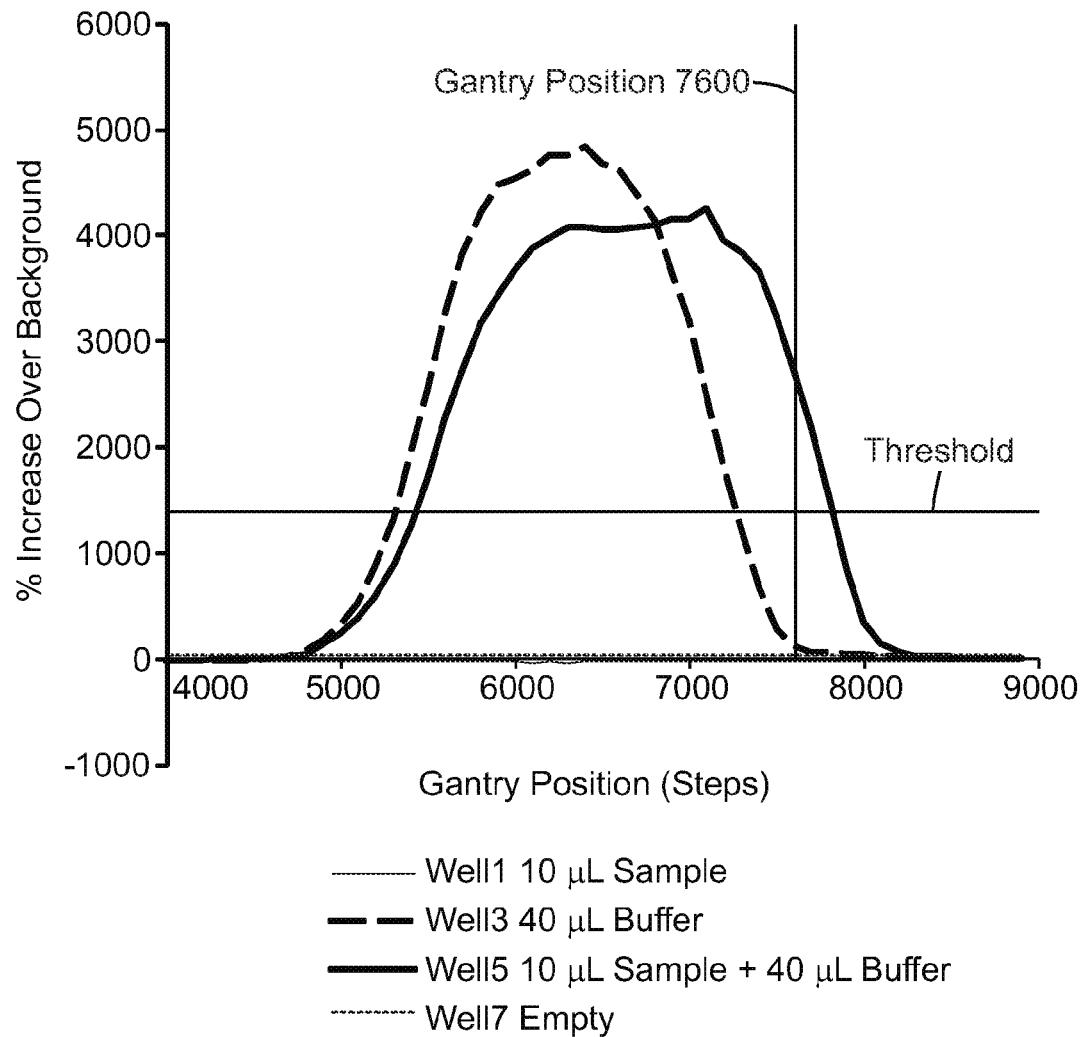
FIG. 31 shows a graphical representation of total fluid level detection using fluorescence detection, as reported in Example 3, Approach 2; each plot showing percent increase in fluorescence over background versus gantry position.

The sample processing device 300 was used in Examples 2 and 3 and FIG. 31.

Figure 23:
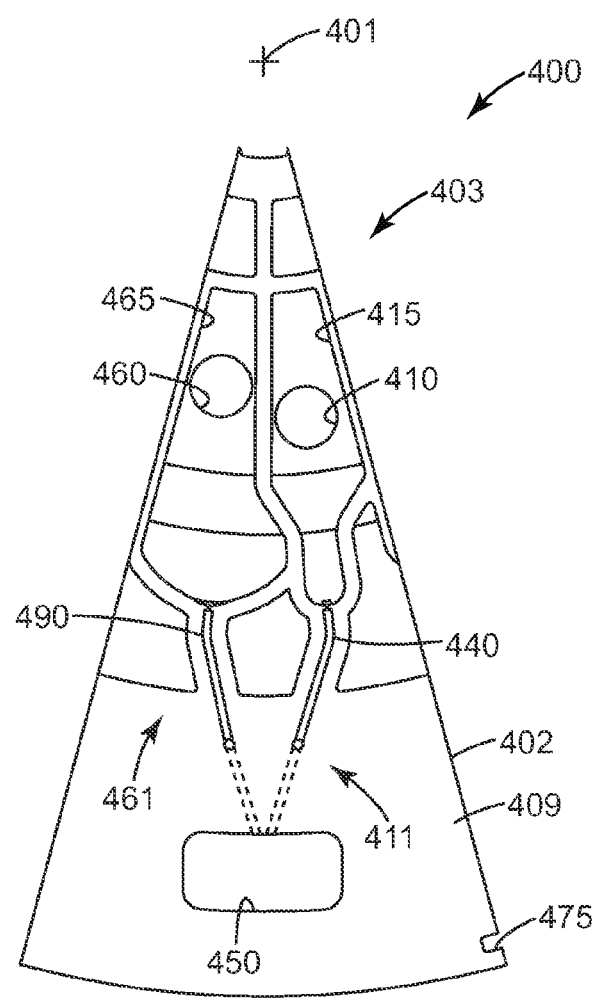
FIG. 23 is a bottom plan view of a sample processing device according to another embodiment of the present disclosure.

FIG. 23 illustrates one lane 403 of another sample processing device 400 according to another embodiment of the present disclosure, wherein like numerals represent like elements. The sample processing device 400 shares many of the same elements and features described above with reference to the illustrated embodiment of FIGS. 16-22. Accordingly, elements and features corresponding to elements and features in the illustrated embodiment of FIGS. 16-22 are provided with the same reference numerals in the 400 series. Reference is made to the description above accompanying FIGS. 16-22 for a more complete description of the features and elements (and alternatives to such features and elements) of the embodiment illustrated in FIG. 23.

The sample processing device 400 is also generally circular or disk-shaped, and one lane 403 is shown by way of example only in FIG. 23. The sample processing device 400 includes a center 401 about which the sample processing device 400 can be rotated to move material therethrough. The sample processing device 400 includes a sample handling side 411 and a reagent handling side 461. The sample processing device 400 includes a substrate 402, a bottom surface 409 of which is shown in FIG. 23, and can further include first and second layers (including pre-use layers), such as those described above with respect to the sample processing device 300 of FIGS. 16-22. The sample processing device 400 can include a slot 475 formed through the substrate 402 or other structure (e.g., reflective tab, etc.) for homing and positioning the sample processing device 400, for example, relative to electromagnetic energy sources, optical modules, and the like, as described above with respect to FIGS. 12-14.

Each side 411, 461 includes an input aperture 410, 460, an input chamber 415, 465, and a distribution channel 440, 490 for transporting the sample and the reagent, respectively, to a detection chamber 450, wherein the sample and the reagent can be combined. As shown in FIG. 23, in some embodiments, the reagent input chamber 465 can be sized larger than the sample input chamber 415 to accommodate a greater volume of reagent than sample.

Unlike the sample processing device 300, the sample processing device 400 includes no specific metering or valving structures. However, the aspect ratios of the cross-sectional area of an inlet of the distribution channels 440, 490 relative to the volume of the respective input chambers 415, 465 can be the same as that described above with respect to the fluid pathway 328 of the sample processing device 300, such that the timing of transfer of the sample and/or the reagent from the input chamber 415, 465 to the detection chamber 450 can be controlled. In addition, the aspect ratio of the sample distribution channel 440 need not be the same as that of the reagent distribution channel 490, such that even if the sample and the reagent are simultaneously loaded onto the sample processing device 400, the sample and the reagent can still be transferred to the detection chamber 450 at different times, depending on the force exerted on the materials (e.g., due to rotation speed).

In some embodiments, the sample can first be loaded onto the sample processing device 400 and transferred to the detection chamber 450 by spinning the sample processing device 400, and then the reagent can be loaded, and the sample processing device 400 can be spun to transfer the reagent to the detection chamber 450 where it can be combined with the sample, and optionally thermally processed.

In some cases, the sample processing device 400 of FIG. 23 can be used for testing of processes and systems for determining whether a material, or a selected volume of material, is present in a particular chamber of a sample processing device, because the variable of metering and valving structures is removed. The sample processing device 400 was used in Example 1 and FIGS. 27-30.

Exemplary Disk Handling System Including an Exemplary Sample Processing Device

Some embodiments of the sample processing systems of the present disclosure can include a disk handling system. Such disk handling systems can include base plates (such as the previously described rotating platform 25) attached to a drive system in a manner that provides for rotation of the base plate about an axis of rotation. When a sample processing device is secured to the base plate, the sample processing device can be rotated with the base plate. The base plate can include at least one thermal structure that can be used to heat portions of the sample processing device and may include a variety of other components as well, e.g., temperature sensors, resistance heaters, thermoelectric modules, light sources, light detectors, transmitters, receivers, etc.

Other elements and features of systems and methods for processing sample processing and/or handling devices can be found in U.S. Patent Application Publication No. 2011/0117607, which is incorporated herein by reference in its entirety.

One illustrative disk handling system 500 is shown in FIG. 24. The system 500 shown in FIG. 24 is generally configured for handing a sample processing device (e.g., the sample processing device 300), including rotating the sample processing device and positioning the sample processing device in a location relative to the other components of the sample processing system 12 (e.g., optical modules, etc., not shown in FIG. 24). In addition, the system 500 can be configured to heat and/or cool the sample processing device, for example, for thermal processing.

As shown in FIG. 24, the system 500 can include a base plate 510 that rotates about an axis of rotation 511. The base plate 510 can also be attached to a drive system 520, for example, via a shaft 522. It will, however, be understood that the base plate 510 may be coupled to the drive system 520 through any suitable alternative arrangement, e.g., belts or a drive wheel operating directly on the base plate 510, etc.

Also depicted in FIG. 24 is the sample processing device 300 and an annular cover 560 that can be used in connection with the base plate 510. In some embodiments, disk handling systems and/or sample processing systems of the present disclosure may not actually include a sample processing device because, in some instances, sample processing devices are consumable devices that are used to perform a variety of tests, etc. and are then discarded. As a result, the systems of the present disclosure may be used with a variety of different sample processing devices, and the sample processing device 300 is shown by way of example only.

As shown in FIG. 24, the depicted base plate 510 includes a thermal structure 530 that can include a thermal transfer surface 532 exposed on the top surface 512 of the base plate 510. By "exposed" it is meant that the transfer surface 532 of the thermal structure 530 can be placed in physical contact with a portion of the sample processing device 300 such that the thermal structure 530 and the sample processing device 550 are thermally coupled to transfer thermal energy via conduction. In some embodiments, the transfer surface 532 of the thermal structure 530 can be located directly beneath selected portions of the sample processing device 300 during sample processing. For example, in some embodiments, the selected portions of the sample processing device 300 can include one or more process chambers, such as the process chambers 350, that can be considered "thermal process chambers." The process chambers, for example, can include those discussed in, e.g., U.S. Pat. No. 6,734,401 titled ENHANCED SAMPLE PROCESSING DEVICES SYSTEMS AND METHODS (Bedingham et al.). By way of further example, the sample processing device 300 can include various features and elements, such as those described in U.S. Patent Publication No. 2007/0009391 titled COMPLIANT MICROFLUIDIC SAMPLE PROCESSING DISKS (Bedingham et al.).

As a result, by way of example only, the input chambers 315, 365 of the sample processing device 300 can sometimes be referred to as "non-thermal" chambers or "non-thermal" process chambers, positioned in fluid communication with the thermal process chambers 350. A sample can be loaded onto the sample processing device 300 and moved via channels (e.g., microfluidic channels) and/or valves, as described above with respect to FIGS. 16-22, to other chambers and/or ultimately to the thermal process chambers 350.

In some embodiments, as shown in FIG. 24, the input apertures 310, 360 can be positioned between a center 301 of the sample processing device 300 and at least one of the thermal process chambers 350. In addition, the annular cover 560 can be configured to allow access to a portion of the sample processing device 300 that includes the input apertures 310, 360, such that the input apertures 310, 360 can be accessed when the cover 560 is positioned adjacent to or coupled to the sample processing device 300.

As shown in FIG. 24, the annular cover 560 can, together with the base plate 510, compress the sample processing device 300 located therebetween, for example, to enhance thermal coupling between the thermal structure 530 on the base plate 510 and the sample processing device 300. In addition, the annular cover 560 can function to hold and/or maintain the sample processing device 300 on the base plate 510, such that the sample processing device 300 and/or the cover 560 can rotate with the base plate 510 as it is rotated about axis 511 by drive system 520. The rotation axis 511 can define a z-axis of the system 500.

As used herein, the term "annular" or derivations thereof can refer to a structure having an outer edge and an inner edge, such that the inner edge defines an opening. For example, an annular cover can have a circular or round shape (e.g., a circular ring) or any other suitable shape, including, but not limited to, triangular, rectangular, square, trapezoidal, polygonal, etc., or combinations thereof. Furthermore, an "annulus" of the present invention need not necessarily be symmetrical, but rather can be an asymmetrical or irregular shape; however, certain advantages may be possible with symmetrical and/or circular shapes.

The compressive forces developed between the base plate 510 and the cover 560 may be accomplished using a variety of different structures or combination of structures. One exemplary compression structure depicted in the embodiment of FIG. 24 includes magnetic elements 570 located on (or at least operatively coupled to) the cover 560 and corresponding magnetic elements 572 located on (or at least operatively coupled to) the base plate 510. Magnetic attraction between the magnetic elements 570 and 572 may be used to draw the cover 560 and the base plate 510 towards each other, thereby compressing, holding, and/or deforming the sample processing device 300 located therebetween. As a result, the magnetic elements 570 and 572 can be configured to attract each other to force the annular cover 560 in a first direction $D_1$ along the z-axis of the system 500, such that at least a portion of the sample processing device 300 is urged into contact with the transfer surface 532 of the base plate 510.

As used herein, a "magnetic element" is a structure or article that exhibits or is influenced by magnetic fields. In some embodiments, the magnetic fields can be of sufficient strength to develop the desired compressive force that results in thermal coupling between the sample processing device 300 and the thermal structure 530 of the base plate 510 as discussed herein. The magnetic elements can include magnetic materials, i.e., materials that either exhibit a permanent magnetic field, materials that are capable of exhibiting a temporary magnetic field, and/or materials that are influenced by permanent or temporary magnetic fields.

Some examples of potentially suitable magnetic materials include, e.g., magnetic ferrite or "ferrite" which is a substance including mixed oxides of iron and one or more other metals, e.g., nanocrystalline cobalt ferrite. However, other ferrite materials may be used. Other magnetic materials which may be used in the system 500 may include, but are not limited to, ceramic and flexible magnetic materials made from strontium ferrous oxide which may be combined with a polymeric substance (such as, e.g., plastic, rubber, etc.); NdFeB (this magnetic material may also include Dysprosium); neodymium boride; SmCo (samarium cobalt); and combinations of aluminum, nickel, cobalt, copper, iron, titanium, etc.; as well as other materials. Magnetic materials may also include, for example, stainless steel, paramagnetic materials, or other magnetizable materials that may be rendered sufficiently magnetic by subjecting the magnetizable material to a sufficient electric and/or magnetic field.

In some embodiments, the magnetic elements 570 and/or the magnetic elements 572 can include strongly ferromagnetic material to reduce magnetization loss with time, such that the magnetic elements 570 and 572 can be coupled with a reliable magnetic force, without substantial loss of that force over time.

Furthermore, in some embodiments, the magnetic elements of the present disclosure may include electromagnets, in which the magnetic fields can be switched on and off between a first magnetic state and a second non-magnetic state to activate magnetic fields in various areas of the system 500 in desired configurations when desired.

In some embodiments, the magnetic elements 570 and 572 can be discrete articles operatively coupled to the cover 560 and the base plate 510, as depicted in FIG. 24 (in which the magnetic elements 570 and 572 are individual cylindrically-shaped articles). However, in some embodiments, the base plate 510, the thermal structure 530, and/or the cover 560 can include sufficient magnetic material (e.g., molded or otherwise provided in the structure of the component), such that separate discrete magnetic elements are not required. In some embodiments, a combination of discrete magnetic elements and sufficient magnetic material (e.g., molded or otherwise) can be employed.

As shown in FIG. 24, the annular cover 560 includes a center 501, which, in the illustrated embodiment is in line with the rotation axis 511 when the cover 560 is coupled to the base plate 510, an inner edge 563 that at least partially defines an opening 566, and an outer edge 565. As described above, the opening 566 can facilitate accessing at least a portion of the sample processing device 300 (e.g., a portion comprising the input apertures 310, 360), for example, even when the annular cover 560 is positioned adjacent to or coupled to the sample processing device 300. As shown in FIG. 24, the inner edge 563 of the annular cover 560 can be configured to be positioned inwardly (e.g., radially inwardly) of the thermal process chambers 350, relative to the center 501 of the annular cover 560, for example, when the annular cover 560 is positioned adjacent the sample processing device 300. In addition, the inner edge 563 of the annular cover 560 can be configured to be positioned radially outwardly of the input apertures 310, 360. Furthermore, in some embodiments, as shown in FIG. 24, the outer edge 565 of the annular cover 560 can be configured to be positioned outwardly (e.g., radially outwardly) of the thermal process chambers 350 (and also outwardly of the input apertures 310, 360).

The inner edge 563 can be positioned a first distance $d_1$ (e.g., a first radial distance or "first radius") from the center 501 of the annular cover 560. In such embodiments, if the annular cover 560 has a substantially circular ring shape, the opening 566 can have a diameter equal to twice the first distance $d_1$. In addition, the outer edge 565 can be positioned a second distance $d_2$ (e.g., a second radial distance or "second radius") from the center 501 of the annular cover 560.

In addition, the annular cover 560 can include an inner wall 562 (e.g., an "inner circumferential wall" or "inner radial wall"; which can function as an inner compression ring, in some embodiments, as described below) and an outer wall 564 (e.g., an "outer circumferential wall" or "outer radial wall"; which can function as an outer compression ring, in some embodiments, as described below). In some embodiments, inner and outer walls 562 and 564 can include or define the inner and outer edges 563 and 565, respectively, such that the inner wall 562 can be positioned inwardly (e.g., radially inwardly) of the thermal process chambers 350, and the outer wall 564 can be positioned outwardly (e.g., radially outwardly) of the thermal process chambers 350. As further shown in FIG. 24, in some embodiments, the inner wall 562 can include the magnetic elements 570, such that the magnetic elements 570 form a portion of or are coupled to the inner wall 562. For example, in some embodiments, the magnetic elements 570 can be embedded (e.g., molded) in the inner wall 562. As shown in FIG. 24, the annular cover 560 can further include an upper wall 567 that can be positioned to cover a portion of the sample processing device 300, such as a portion that comprises the thermal process chambers 350.

In some embodiments, the upper wall 567 can extend inwardly (e.g., radially inwardly) of the inner wall 562 and the magnetic elements 570. In the embodiment illustrated in FIG. 24, the upper wall 567 does not extend much inwardly of the inner wall 562. However, in some embodiments, the upper wall 567 can extend further inwardly of the inner wall 562 and/or the magnetic elements 570 (e.g., toward the center 501 of the cover 560), for example, such that the size of the opening 566 is smaller than what is depicted in FIG. 24. Furthermore, in some embodiments, the upper wall 567 can define the inner edge 563 and/or the outer edge 565.

In some embodiments, at least a portion of the cover 560, such as one or more of the inner wall 562, the outer wall 564, and the upper wall 567, can be optically clear. As used herein, the phrase "optically clear" can refer to an object that is transparent to electromagnetic radiation ranging from the infrared to the ultraviolet spectrum (e.g., from about 10 nm to about 10 nm (10,000 nm)); however, in some embodiments, the phrase "optically clear" can refer to an object that is transparent to electromagnetic radiation in the visible spectrum (e.g., about 400 nm to about 700 nm). In some embodiments, the phrase "optically clear" can refer to an object with a transmittance of at least about 80% within the wavelength ranges above.

Such configurations of the annular cover 560 can function to effectively or substantially isolate the thermal process chambers 350 of the sample processing device 300 when the cover 560 is coupled to or positioned adjacent the sample processing device 300. For example, the cover 560 can physically, optically, and/or thermally isolate a portion of the sample processing device 300, such as a portion comprising the thermal process chambers 350. In some embodiments, the sample processing device 300 can include one or more thermal process chambers 350, and further, in some embodiments, the one or more thermal process chambers 350 can be arranged in an annulus about the center 301 of the sample processing device 300, which can sometimes be referred to as an "annular processing ring." In such embodiments, the annular cover 560 can be adapted to cover and/or isolate a portion of the sample processing device 300 that includes the annular processing ring or the thermal process chambers 350. For example, the annular cover 560 includes the inner wall 562, the outer wall 564, and the upper wall 567 to cover and/or isolate the portion of the sample processing device 300 that includes the thermal process chambers 350. In some embodiments, one or more of the inner wall 562, the outer wall 564, and the upper wall 567 can be a continuous wall, as shown, or can be formed of a plurality of portions that together function as an inner or outer wall (or inner or outer compression ring), or an upper wall. In some embodiments, enhanced physical and/or thermal isolation can be obtained when at least one of the inner wall 562, the outer wall 564 and the upper wall 567 is a continuous wall.

In addition, in some embodiments, the ability of the annular cover 560 to cover and effectively thermally isolate the thermal process chambers 350 from ambience and/or from other portions of the system 500 can be important, because otherwise, as the base plate 510 and the sample processing device 300 are rotated about the rotation axis 511, air can be caused to move quickly past the thermal process chambers 350, which, for example, can undesirably cool the thermal process chambers 350 when it is desired for the chambers 350 to be heated. Thus, in some embodiments, depending on the configuration of the sample processing device 300, one or more of the inner wall 562, the upper wall 567 and the outer wall 564 can be important for thermal isolation.

As shown in FIG. 24, in some embodiments, the substrate 302 of the sample processing device 300 can include an outer lip, flange or wall 395. In some embodiments, as shown, the outer wall 395 can include a portion 391 adapted to cooperate with the base plate 510 and a portion 399 adapted to cooperate with the annular cover 560. For example, as shown, the annular cover 560 (e.g., the outer wall 564) can be dimensioned to be received within the area circumscribed by the outer wall 395 of the sample processing device 300. As a result, in some embodiments, the outer wall 395 of the sample processing device 300 can cooperate with the annular cover 560 to cover and/or isolate the thermal process chambers 350. Such cooperation can also facilitate positioning of the annular cover 560 with respect to the sample processing device 300 such that the thermal process chambers 350 are protected and covered without the annular cover 560 pressing down on or contacting any of the thermal process chambers 350.

In some embodiments, the outer wall 395 of the sample processing device 300 and one or more steps 313 (e.g., the middle step 313 shown in FIG. 24) of the sample processing device 300 can effectively define a recess (e.g., an annular recess) 353 in the sample processing device 300 (e.g., in a top surface of the sample processing device 300) in which at least a portion of the annular cover 560 can be positioned. For example, as shown in FIG. 24, the inner wall 562 (e.g., including the magnetic elements 570) and the outer wall 564 can be positioned in the recess 353 of the sample processing device 300 when the annular cover 560 is positioned over or coupled to the sample processing device 300. As a result, in some embodiments, the outer wall 395, the steps 313 and/or the recess 353 can provide reliable positioning of the cover 560 with respect to the sample processing device 300.

In some embodiments, as shown, the magnetic elements 570 of the cover 560 can form at least a portion of or be coupled to the inner wall 562, such that the magnetic elements 570 can function as at least a portion of the inner compression ring 562 to compress, hold, and/or deform the sample processing device 300 against the thermal transfer surface 532 of the thermal structure 530 of the base plate 510. As shown in FIG. 24, one or both of the magnetic elements 570 and 572 can be arranged in an annulus, for example, about the rotation axis 511. Furthermore, in some embodiments, at least one of the magnetic elements 570 and 572 can include a substantially uniform distribution of magnetic force about such an annulus.

In addition, the arrangement of the magnetic elements 570 in the cover 560 and the corresponding arrangement of the magnetic elements 572 in the base plate 510 can provide additional positioning assistance for the cover 560 with respect to one or both of the sample processing device 300 and the base plate 510. For example, in some embodiments, the magnetic elements 570 and 572 can each include sections of alternating polarity and/or a specific configuration or arrangement of magnetic elements, such that the magnetic elements 570 of the cover 560 and the magnetic elements 572 of the base plate 510 can be "keyed" with respect to each other to allow the cover 560 to reliably be positioned in a desired orientation (e.g., angular position relative to the rotation axis 511) with respect to at least one of the sample processing device 300 and the base plate 510.

Although not explicitly depicted in FIG. 24, in some embodiments, the base plate 510 can be constructed such that the thermal structure 530 is exposed on the top first surface 512 as well as on a bottom second surface 514 of the base plate 510. By exposing the thermal structure 530 on the top surface 512 of the base plate 510 (e.g., alone or in addition to the bottom surface 514), a direct thermal path can be provided between the transfer surface 532 of the thermal structure 530 and a sample processing device 300 located between the cover 560 and the base plate 510.

Alternatively or in addition, exposing the thermal structure 530 on the bottom surface 514 of the base plate 510 may provide an advantage when the thermal structure 530 is to be heated by electromagnetic energy emitted by a source directing electromagnetic energy onto the bottom surface 514 of the base plate 510.

By way of example only, the system 500 includes an electromagnetic energy source 590 positioned to deliver thermal energy to the thermal structure 530, with the electromagnetic energy emitted by the source 590 directed onto the bottom surface 514 of the base plate 510 and the portion of the thermal structure 530 exposed on the bottom surface 514 of the base plate 510. Examples of some suitable electromagnetic energy sources may include, but are not limited to, lasers, broadband electromagnetic energy sources (e.g., white light), etc.

While the system 500 is illustrated as including the electromagnetic energy source 590, in some embodiments, the temperature of the thermal structure 530 can be controlled by any suitable energy source that can deliver thermal energy to the thermal structure 530. Examples of potentially suitable energy sources for use in connection with the present disclosure other than electromagnetic energy sources may include, e.g., Peltier elements, electrical resistance heaters, etc.

The system 500 is an example of a portion of a sample processing system (i.e., a disk handling system) that can be configured to hold, handle, rotate, position, and/or thermally process a sample processing device of the present disclosure. The system 500 can be incorporated into the system 12 of FIGS. 1-15. For example, with reference to FIG. 8, the sample processing device 300 can take the place of disk 13, and the system 500 can be used to position the sample processing device 300 with respect to the other components (e.g., on a gantry 60) of the system 12. In addition, the sample 22 can be located in a thermal process chamber 350 on the sample processing device 300. Furthermore, the base plate 510 and drive system 520 can be used as the rotating platform of FIG. 1. As a result, it is clear from the above disclosure and accompanying figures how a disk or sample processing device of the present disclosure can be held, handled, rotated, thermally processed, and/or positioned relative to the other components (e.g., detection device 10) of the system 12.

While various embodiments of the present disclosure are shown in the accompanying drawings by way of example only, it should be understood that a variety of combinations of the embodiments described and illustrated herein can be employed without departing from the scope of the present disclosure. For example, the sample processing device 300 is shown in use with the system 500 of FIG. 24, however, it should be understood that the sample processing device 400 of FIG. 23 can instead be employed with the system 500. In addition, various features of the system 500 can be employed as part of the overall system 12 of FIGS. 1-15. Furthermore, various features of the sample processing device 300 of FIGS. 16-22 can be employed in the sample processing device 400 FIG. 23, and vice versa. As a result, the present disclosure should be taken as a whole for all of the various features, elements, and alternatives to those features and elements described herein, as well as the possible combinations of such features and elements.

Processes for Determining Whether a Selected Volume of Material is Present

An exemplary process for loading a sample and a reagent into a sample processing device and verifying that a selected volume of the sample has been moved to, or is present in, the detection chamber 350 will now be described with reference to the sample processing system 12 of FIGS. 1-15, the system 500 of FIG. 24, and the sample processing device 300 of FIGS. 16-22. Particularly, one lane 303 of the sample processing device 300 will be described regarding sample movement.

As mentioned above, in order to detect that a sample has moved to, or is present in, the detection chamber 350 of a given lane 303, a variety of methodologies can be used:

(1) the detection chamber 350 can be scanned after only the sample has been loaded, any necessary valves have been opened (e.g., on the sample handling side 311 of the lane 303), and the sample processing device 300 has been rotated to move the sample to the detection chamber 350;

(2) the detection chamber 350 can be scanned after only the reagent has been loaded, any necessary valves have been opened (e.g., on the reagent handling side 361 of the lane 303), and the sample processing device 300 has been rotated to move the reagent to the detection chamber 350;

(3) the detection chamber 350 can be scanned after both the sample and the reagent have been loaded, any necessary valves have been opened (e.g., on both sides 311, 361 of the lane 303), and the sample processing device 300 has been rotated to move the sample and the reagent to the detection chamber 350; and/or (4) a combination of any of the above methods.

An example of methodology (4) can include creating a first scan of the detection chamber 350 after only the reagent has been transferred, and then creating a second scan of the detection chamber 350 after the sample has further been added to the detection chamber 350, and then comparing the two scans. A further development of this example is described below.

In some embodiments (e.g., in methodology (1)), the fluorescence detection capabilities of the detection device 10 can be used to detect the backscattered reflection of an optical signal to detect a meniscus layer in the material. However, in some embodiments, the detection device 10 can detect the fluorescence signal from one or more fluorescent probes in the material (e.g., in the reagent), and the 'egde' of such a signal (e.g., peak) would indicate the amount of fluid in the detection well. Still, in some embodiments, a combination of these detection schemes can be employed.

In either type of detection scheme (i.e., backscatter and/or fluorescence), the detection chamber 350 can be scanned in one or more of the following ways:

(a) the detection chamber 350 can be scanned from one radial end to another radial end before and after moving the sample (or the sample and the reagent), and two scans can be created that represent the detection chamber 350 from one end to another (e.g., where in the graphical representation of such a scan, the x-axis can represent gantry or radial position) before and after the material was moved;

(b) the detection chamber 350 can be scanned at one radial position before and after moving the sample (or the sample and reagent) to the detection chamber 350 to determine if the scan changes when a material is present; or (c) a combination thereof.

In any scan method, the presence or absence of material can be detected, and/or the amount of material can be determined. All scan methods can be performed while the sample processing device 300 is rotating to exploit the phenomenon that any material present in the detection chamber 350 will be subject to a centrifugal force, and will have an upper level that will generally be well-defined and located between a radial innermost end (or "inner boundary") 351 and radial outermost end (or "outer boundary") 352 of the detection chamber 350 (see FIG. 20). That is, rotation of the sample processing device 300 about the axis of rotation A-A can force any material present in the detection chamber 350 to a position in the detection chamber 350 that is located furthest from the axis of rotation A-A, such that the material becomes forced against the outer boundary 352 of the detection chamber 350.

Also, as mentioned above, desired volumes of the sample and the reagent can be moved to the detection chamber 350, either by metering, as is the case for the sample processing device 300 of FIGS. 16-22, or by accurately loading a desired volume of each into the input wells, as is the case for the sample processing device 400 of FIG. 23. As a result, the system 12 can be calibrated to correlate a radial position (e.g., a gantry position of the gantry 60 of FIG. 8) in the detection chamber 350 with a volume of material.

If, for example, the methodology (1) is used, and if volume $V_1$ (e.g., 10 microliters) of the sample should be transferred to the detection chamber 350, the system 12 can be calibrated to correlate a position $P_1$ (e.g., a radial or gantry position; see FIG. 20) with volume $V_1$, or the position $P_1$ can be chosen to be below, or just below, the level of volume $V_1$. Such a position $P_1$ will correlate with volume $V_1$ while the sample processing device 300 is rotated such that material is forced against the radially outermost wall of the detection chamber 350.

If, for example, the methodology (2) is used, and if volume $V_2$ (e.g., 40 microliters) of the reagent should be transferred to the detection chamber 350, the system 12 can be calibrated to correlate a position $P_2$ (see FIG. 20) with volume $V_2$, or the position $P_2$ can be chosen to be below, or just below, the level of volume $V_2$.

Furthermore, if the user knows that a total volume $V_3$ (e.g., 50 microliters if 40 microliters of reagent and 10 microliters of sample are loaded) should be present in the detection chamber 350 after both the sample and the reagent are caused to move to the detection chamber 350, the system 12 can be calibrated correlate a position $P_3$ (see FIG. 20) with volume $V_3$, or the position $P_3$ can be chosen to be below, or just below, the level of volume $V_3$. In some embodiments, position $P_3$ can be a radial position proximate the inner boundary 351 of the detection chamber 350.

Figure 25:
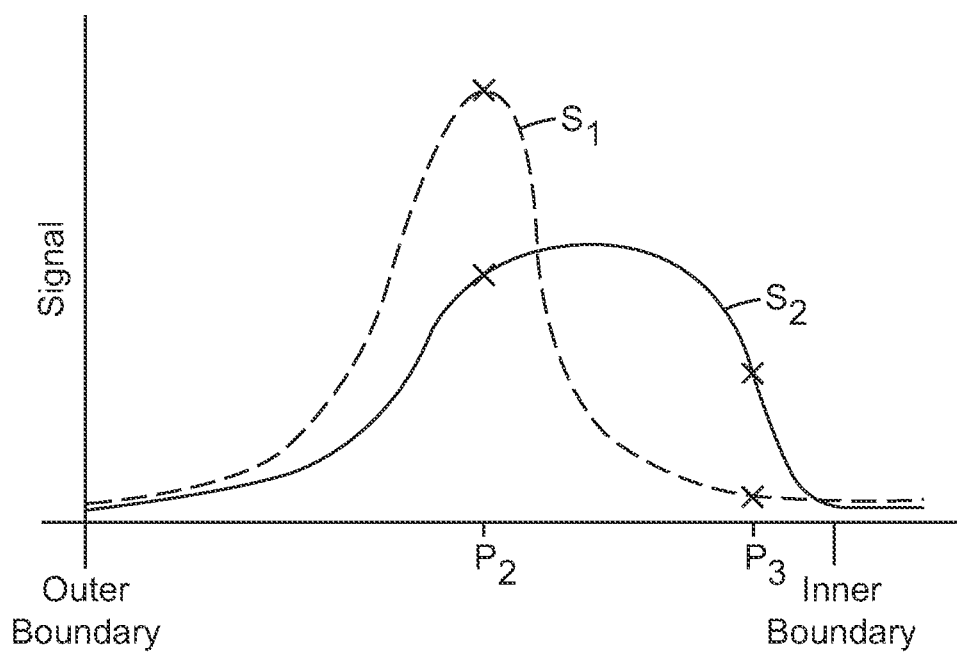
FIG. 25 is a schematic graphical representation of one embodiment of a method for comparing two scans of a detection chamber to determine whether a sample is present in the detection chamber.

With reference to FIG. 20 and FIG. 25, in some embodiments, the dilution phenomenon of the fluorescence in the reagent after the sample and the reagent are combined can be exploited to confirm whether the sample, or a selected volume of the sample, has been appropriately moved to the detection chamber 350. For example, in some embodiments, a first, reagent-only scan $S_1$ (i.e., from the outer boundary 352 to the inner boundary 351 of the detection chamber 350) can be compared to a second, sample+reagent scan $S_2$. Because the concentration of fluorescent probes should generally decrease due to the dilution of signal when the sample is added to the reagent, the peak fluorescence of the first scan (i.e., reagent-only) $S_1$ will generally be greater than the peak fluorescence of the second scan (i.e., sample+reagent) $S_2$, and particularly, at position $P_2$. However, because no material will be present at position $P_3$ in the first scan $S_1$, the signal at position $P_3$ in the first scan $S_1$ should be very low. On the contrary, in the second scan $S_2$, the fluorescence at position $P_2$ will be decreased due to reduced concentration of the fluorescence, but the fluorescence at position $P_3$ should be higher than that of the first scan $S_1$, because material will be present at position $P_3$ when both the sample and the reagent are present. As a result, the difference between the fluorescence of the two scans $S_1$, $S_2$ (or the percent decrease) at position $P_2$, and/or the difference between the fluorescence of the two scans $S_1$, $S_2$ (or the percent increase) at position $P_3$ can be used to confirm whether the sample, or a selected volume thereof, has moved to the detection chamber 350. In some embodiments, the "signal" units can be relative fluorescence intensity units, and in some embodiments, can be a percent change relative to a background signal.

In order to determine that the sample has been moved to the detection chamber 350 or that a desired volume of the sample has been moved, the detection chamber 350 can be scanned before and after the sample (or the sample and the reagent) are moved to the detection chamber 350, and the scans can be compared. That is, a first "background scan" can be taken when the detection chamber 350 is assumed to be empty, and that scan can be compared to a second scan when (i) the sample, (ii) the reagent, and/or (iii) the sample and reagent are assumed to be present in the detection chamber 350. If a threshold change or difference (e.g., percent change) exists between the first background scan and the second scan (e.g., at a desired radial position), it can be determined that the sample, or a selected volume of the sample, is present in the detection chamber 350. In some embodiments, the volume of material in the detection chamber 350 can be determined by first determining the radial position in the detection chamber 350 at which the threshold change is found, and then correlating that radial position to a volume in order to determine the volume of material that is present in the detection chamber 350.

In order to avoid any potential optical signal drift as a result of temperature variation during the processing of a sample, the background scan of the detection chamber 350 can be taken at the same processing temperature at which later scans will be taken (e.g., at a cell lysis temperature). However, in some embodiments, the sample processing device 300 may not be "pre-heated" in this way, and the background scan can be taken at room temperature. It should be noted that the background scan can be taken before any material (e.g., sample) is loaded onto the sample processing device 300, or after material is loaded but prior to any valves being opened (i.e., prior to causing any material to be moved to the detection chamber 350).

The details of the exemplary process 600 will now be described with reference to FIG. 26.

By way of example only, for the exemplary process 600, the sample and the reagent will both be loaded onto the sample processing device 300 before the sample processing device 300 is positioned on the system 500. However, it should be understood that the sample and the reagent can instead be loaded onto the sample processing device 300 after a background scan of the detection chambers 350 has been obtained.

The sample and the reagent are loaded onto the sample processing device or "disk" 300 (step 602 in FIG. 26) by removing the pre-use layer 305 over the lane 303 of interest and injecting (e.g., pipetting) the raw sample into the input chamber 315 via the input aperture 310 on the sample handling side 311 of the lane 303. The reagent can also be loaded at this time, so for this example, we will assume that the reagent is also loaded onto the disk 300 at this time by injecting the reagent into the input chamber 365 via the input aperture 360 on the reagent handling side 361 of the lane 303. A plug 307, or other appropriate seal, film, or cover, can then be used to seal the apertures 310, 360 from ambience, as described above. For example, in some embodiments, the pre-use layer 305 can simply be replaced over the input apertures 310, 360.

The disk 300 can be loaded onto the disk handling system 500 (step 604), and coupled between the base plate 510 and the cover 560, such that the disk 300, and particularly, the detection chambers (or the thermal process chambers) 350 are urged into contact with the transfer surface 532 of the base plate 510.

The drive system 520 can be operated to rotate the base plate 510 about the rotation axis 511, which causes the disk 300 to rotate about its center 301, which is aligned with rotation axis 511. The disk 300 can be rotated at a first speed (or speed profile) and a first acceleration (or acceleration profile) sufficient to force the sample and the reagent into their respective metering reservoirs 318, 368, with any excess over the desired volumes being directed into the respective waste reservoirs 320, 370 (step 606).

For example, in some embodiments, a first speed profile may include the following: the disk 300 is (i) rotated at a first speed to move the materials to their respective metering reservoirs 318, 368 without forcing all of the material into the waste reservoirs 320, 370, (ii) held for a period of time (e.g., 3 seconds), and (iii) rotated at a second speed to cause any amount of material greater than the volume of the metering reservoir 318, 368 to overflow into the waste reservoir 320, 370. Such a rotation scheme can be referred to as a "metering profile," "metering scheme," or the like, because it allows the materials to be moved into the respective metering reservoirs 318, 368 while ensuring that the materials are not forced entirely into the waste reservoirs 320, 370. In such an example, the speed and acceleration are kept below a speed and acceleration that would cause the sample and/or reagent to move into the respective fluid pathway 328, 378 and "wet out" the valve septum 336, 386. Because the speed and acceleration profiles will be sufficient to meter the sample and the reagent while remaining below what might cause wetting out of the septums 336, 386, it can simply be described as a "first" speed and acceleration. That is, the first speed and acceleration is insufficient to force the sample or the reagent into the respective fluid pathways 328, 378, such that the metered volumes of the sample and the reagent remain in their respective input chamber 315, 365.

Various features and details of the metering system and process are described in U.S. Patent Application Nos. 61/487,672, filed May 18, 2011, and 61/490,014, filed May 25, 2011, each of which is incorporated herein by reference in its entirety.

The disk 300 can be allowed to continue rotating, and a background scan can then be taken of the detection chamber 350, generally following the procedure outlined in FIG. 15 and described above (step 608). The electromagnetic source 590 can be powered on, such that the electromagnetic source 590 heats the thermal structure 530 as the disk 300 is rotated, and the transfer surface 532 of the thermal structure 530 heats the detection chambers 350 by conduction. Such heating can function as the "pre-heating" of the disk 300 described above.

The detection device 10, and particularly, one or more of the optical modules 48, 52, 56, can be moved along a radius relative to the center 301 of the sample processing device 300 by the gantry 60. Optical module 48 will be described by way of example only. The optical module 48 can optically interrogate the detection chamber 350 according to either detection scheme described above (i.e., backscatter and/or fluorescence), and develop a background scan from a radial outermost position of the detection chamber 350 all the way to a radial innermost position of the detection chamber 350. Alternatively, as described above, the optical module 48 can interrogate the detection chamber 350 at one or more discrete radial positions (e.g., position $P_1$, $P_2$ and/or $P_3$).

At this time, the disk 300 can be stopped from rotating and one or both of the sample septum valve 332 and the reagent septum valve 382 can be opened, for example, by forming a void in the valve septum(s) 336, 386 using the laser valve control system 51. For the sake of this example, we will assume that a sample-only scan will be taken prior to moving the reagent to the detection chamber 350, such that the sample septum valve 332 will be opened first (step 610). The sample valve septum 336 can be located and opened according to the processes outlined in FIGS. 12 and 14 and described above, to put the input chamber 315 and the detection chamber 350 in fluid communication via a downstream direction.

The disk 300 can then be rotated at a second speed (or speed profile) and the first acceleration (or acceleration profile) sufficient to move the sample into the fluid pathway 328 (i.e., sufficient to open the capillary valve 330 and allow the sample to move therethrough), through the opening formed in the septum 336, through the distribution channel 340, and into the detection chamber 350 (step 612). Meanwhile, any fluid (e.g., gas) present in the detection chamber 350 can be displaced into the equilibrium channel 355 as the sample is moved into the detection chamber 350. This rotation speed and acceleration can be sufficient to move the sample to the detection chamber 350 but not sufficient to cause the reagent to move into the fluid pathway 378 of the capillary valve 380 and wet out the septum 386.

The disk 300 can then be rotated, and a sample-only scan of the detection chamber 350 can be performed (step 614) by operating the optical module 48 and the gantry 60, as described above. The rotation of the disk 300 that occurs during this detection step can be at the same or a different rotation speed and acceleration as the second speed and acceleration. In addition, the disk 300 can be stopped after the sample was caused to move to the detection chamber 350 and then rotated again for detection, the disk 300 can simply continue to be rotated after it is assumed the sample has moved to the detection chamber 350, or a combination thereof. This step can also include heating (e.g., using the electromagnetic source 390 and the thermal structure 530) the detection chambers 350 (e.g., to 75° C.). Such a heating step can cause lysis of cells in the sample, for example. In some embodiments, it is important that the reagent not be present in the detection chamber 350 for this heating step, because temperatures required for thermal cell lysis may denature necessary enzymes (e.g., reverse transcriptase) present in the reagent. Thermal cell lysis is described by way of example only, however, it should be understood that other (e.g., chemical) lysis protocols can be used instead.

The disk 300 can then be stopped from rotating and the reagent septum valve 382 can be opened (step 616). The valve 382 can be opened by using the laser valve control system 51 (i.e., according to the processes outlined in FIGS. 12 and 14) to form a void in the reagent valve septum 386 to put the input chamber 365 in fluid communication with the detection chamber 350 via a downstream direction.

The disk 200 can then be rotated at the second speed (or speed profile) and the second acceleration (or acceleration profile), or a higher speed and/or acceleration than the second speed and acceleration, to transfer the reagent to the detection chamber 350 (step 618). Namely, the rotation speed and acceleration can be sufficient to move the reagent into the fluid pathway 378 (i.e., sufficient to open the capillary valve 380 and allow the reagent to move therethrough), through the opening formed in the septum 386, through the distribution channel 390, and into the detection chamber 350. Meanwhile, any additional fluid (e.g., gas) present in the detection chamber 350 can be displaced into the equilibrium channel 355 as the reagent is moved into the detection chamber 350. This is particularly enabled by embodiments such as the disk 300, because when the disk 300 is rotating, any liquid present in the detection chamber 350 (e.g., the sample) is forced against the outermost end 352, such that any liquid present in the detection chamber 350 will be located radially outwardly of the locations at which the distribution channel 390 and the equilibrium channel 355 connect to the detection chamber 350, so that gas exchange can occur. Said another way, when the disk 300 is rotating, the distribution channel 390 and the equilibrium channel 355 connect to the detection chamber 350 at a location that is upstream (e.g., radially inwardly) of the fluid level in the detection chamber 350.

Step 618 of the process can further include operating one or more optical modules to perform an additional scan of the detection chamber 350 to determine whether a material, or a selected volume of material, is present in the detection chamber 350. For example, in some embodiments, a background scan can be obtained, a first, sample-only (or reagent-only), scan can be obtained, and then a second, sample+reagent, scan can be obtained. As mentioned above, any or all of these scans can include a scan along all radial positions of the detection chamber 350, at multiple discrete radial positions, or at one discrete radial position. In addition, the rotation step used to move the reagent to the detection chamber 350 can be continued for detection, the disk 300 can be stopped and then rotated again for detection, or a combination thereof.

The rotating of the disk 300 can then be continued as needed for a desired reaction and detection scheme (step 620). For example, now that the reagent is present in the detection chamber 350, the detection chamber 350 can be heated to a temperature necessary to begin reverse transcription (e.g., 47° C.). Additional thermal cycling can be employed as needed, such as heating and cooling cycles necessary for PCR, etc.

Various forces can be exerted on materials in the sample processing device 300 at various processing stages. As evident by the speed and acceleration scheme reported in FIG. 26 and described above, such forces can be at least partially controlled by controlling the rotation speeds and acceleration profiles (e.g., angular acceleration, reported in rotations or revolutions per square second (revolutions/sec$^2$) of the sample processing device 300. Some embodiments can include:
  (i) a first speed and a first acceleration that can be used to meter fluids in one or more processing arrays 100 on a sample processing device and are insufficient to cause the fluids to move into the fluid pathways 128 of any processing array 100 on that sample processing device;
  (ii) a second speed and a first acceleration that can be used to move a fluid into the fluid pathway 128 of at least one of the processing arrays 100 on a sample processing device (e.g., in a processing array 100 in which the downstream septum valve 132 has been opened and the vapor lock in the valve chamber 134 has been released, while still inhibiting fluids from moving into the fluid pathways 128 of the remaining processing arrays 100 in which the downstream septum valve 132 has not been opened); and
  (iii) a third speed and a second acceleration that can be used to move fluids into the fluid pathways 128 of all processing arrays 100 on the sample processing device.

In some embodiments, the first speed can be no greater than about 1000 rpm, in some embodiments, no greater than about 975 rpm, in some embodiments, no greater than about 750 rpm, and in some embodiments, no greater than about 525 rpm. In some embodiments, the "first speed" can actually include two discrete speeds—one to move the material into the metering reservoir 118, and another to then meter the material by overfilling the metering reservoir 118 and allowing the excess to move into the waste reservoir 120. In some embodiments, the first transfer speed can be about 525 rpm, and the second metering speed can be about 975 rpm. Both can occur at the same acceleration.

In some embodiments, the first acceleration can be no greater than about 75 revolutions/sec$^2$, in some embodiments, no greater than about 50 revolutions/sec$^2$, in some embodiments, no greater than about 30 revolutions/sec$^2$, in some embodiments, no greater than about 25 revolution/sec$^2$, and in some embodiments, no greater than about 20 revolutions/sec$^2$. In some embodiments, the first acceleration can be about 24.4 revolutions/sec$^2$.

In some embodiments, the second speed can be no greater than about 2000 rpm, in some embodiments, no greater than about 1800 rpm, in some embodiments, no greater than about 1500 rpm, and in some embodiments, no greater than about 1200 rpm.

In some embodiments, the second acceleration can be at least about 150 revolutions/sec$^2$, in some embodiments, at least about 200 revolutions/sec$^2$, and in some embodiments, at least about 250 revolutions/sec$^2$. In some embodiments, the second acceleration can be about 244 revolutions/sec$^2$.

In some embodiments, the third speed can be at least about 3000 rpm, in some embodiments, at least about 3500 rpm, in some embodiments, at least about 4000 rpm, and in some embodiments, at least about 4500 rpm. However, in some embodiments, the third speed can be the same as the second speed, as long as the speed and acceleration profiles are sufficient to overcome the capillary forces in the respective fluid pathways 128.

Figure 26:
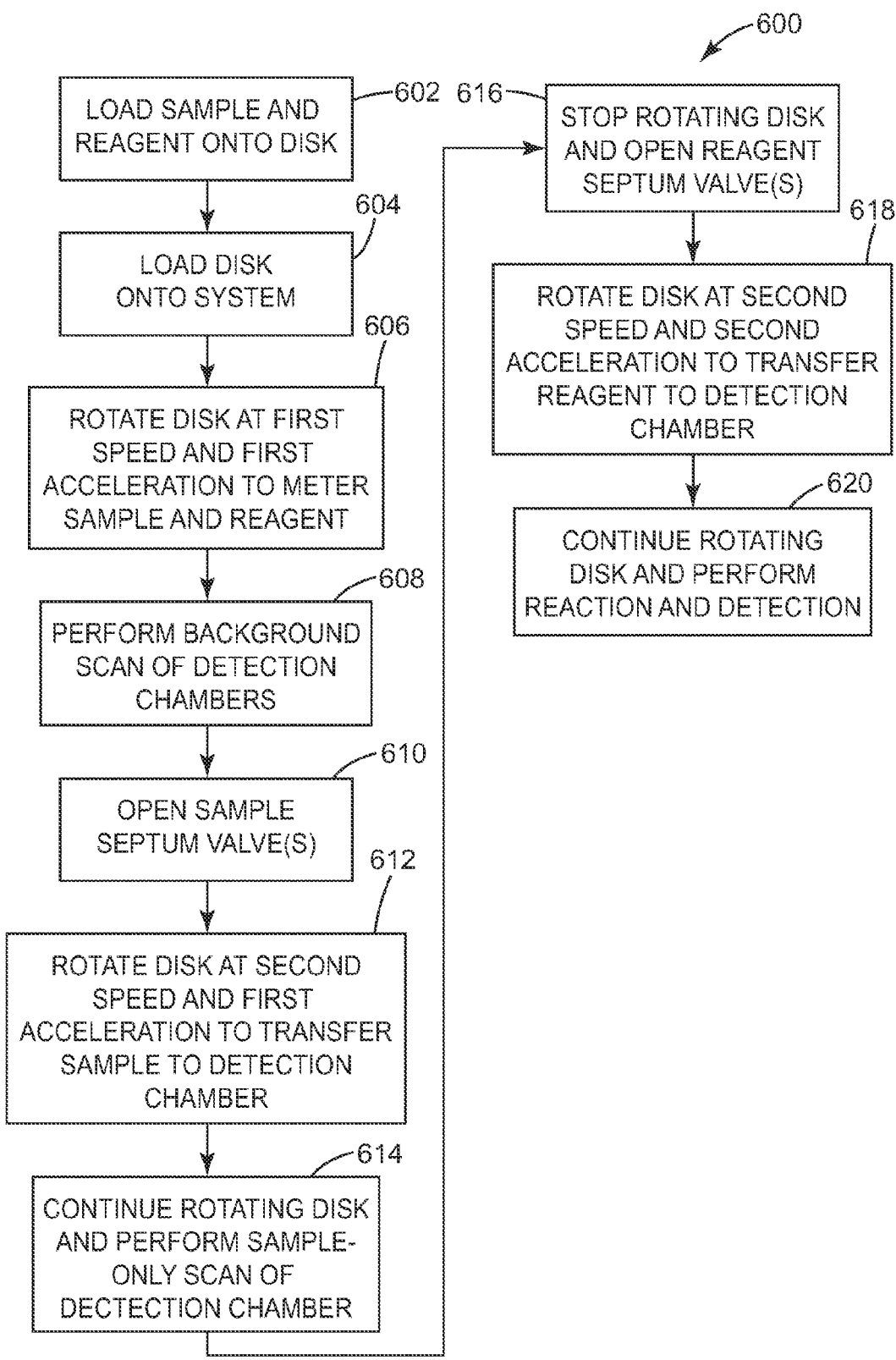
FIG. 26 is a flow diagram illustrating one exemplary method of processing a sample on a sample processing device and determining whether a sample is present in a detection chamber of a sample processing device.
Figure 27:
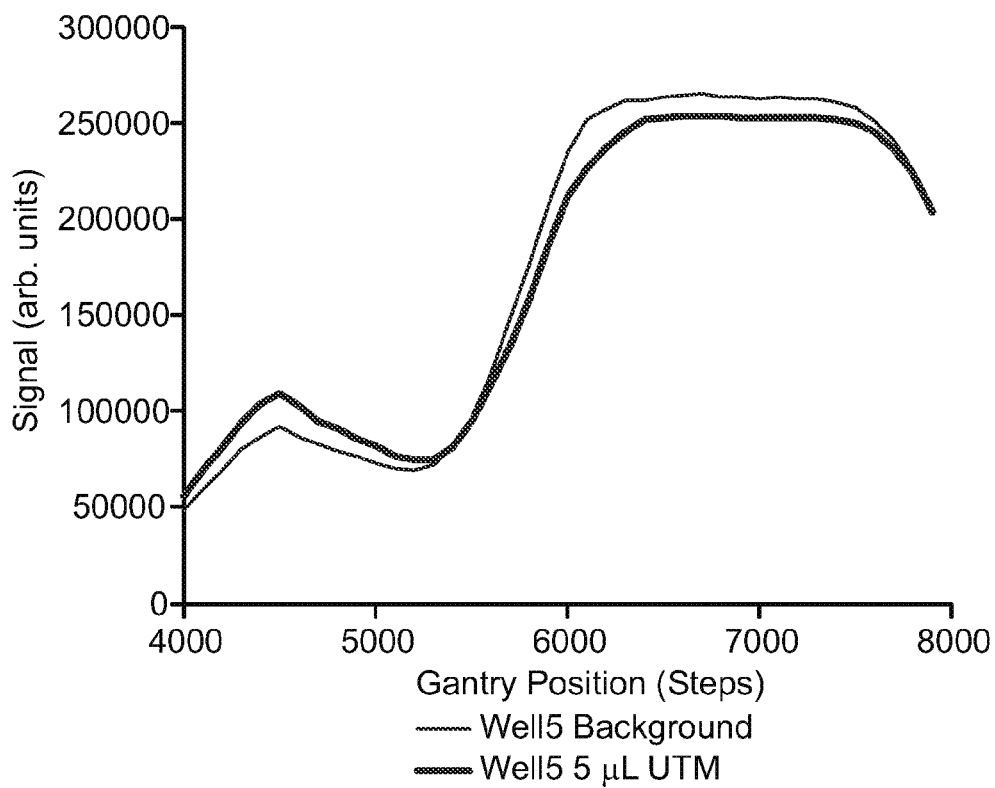
FIGS. 27-30 show graphical representations of meniscus detection results for samples of 5 μL, 10 μL, 15 μL and 20 μL, respectively, as reported in Example 1; each figure showing a first background scan and a second scan of backscattered intensity (arbitrary units) versus gantry position.
Figure 28:
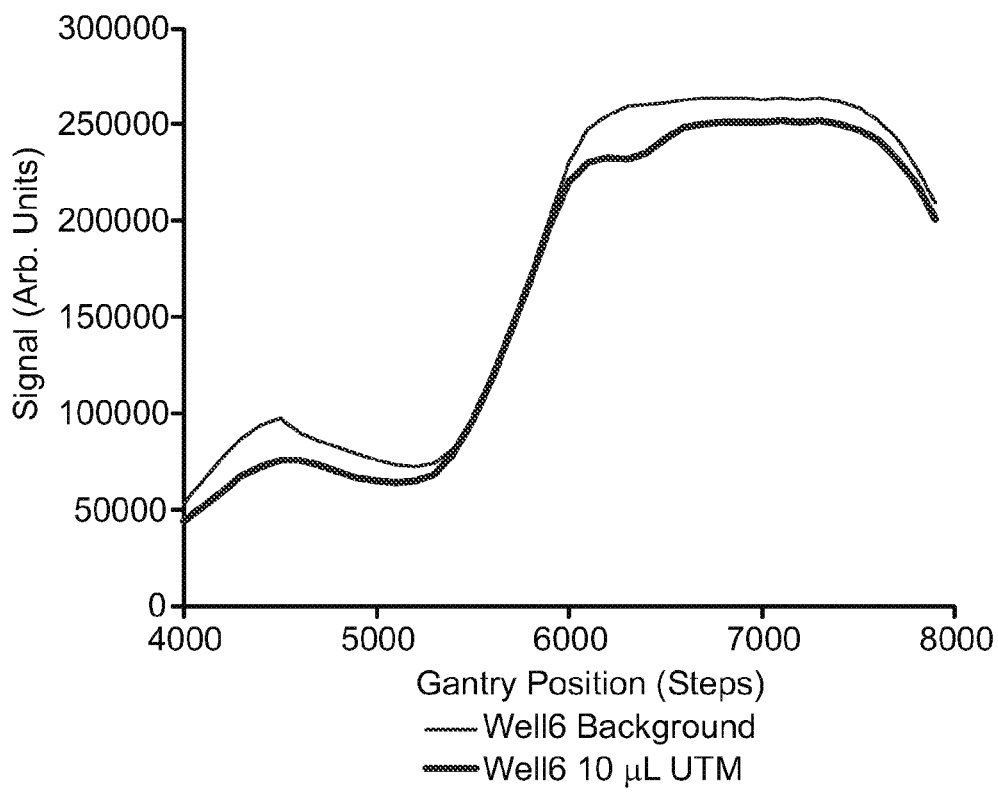
Figure 29:
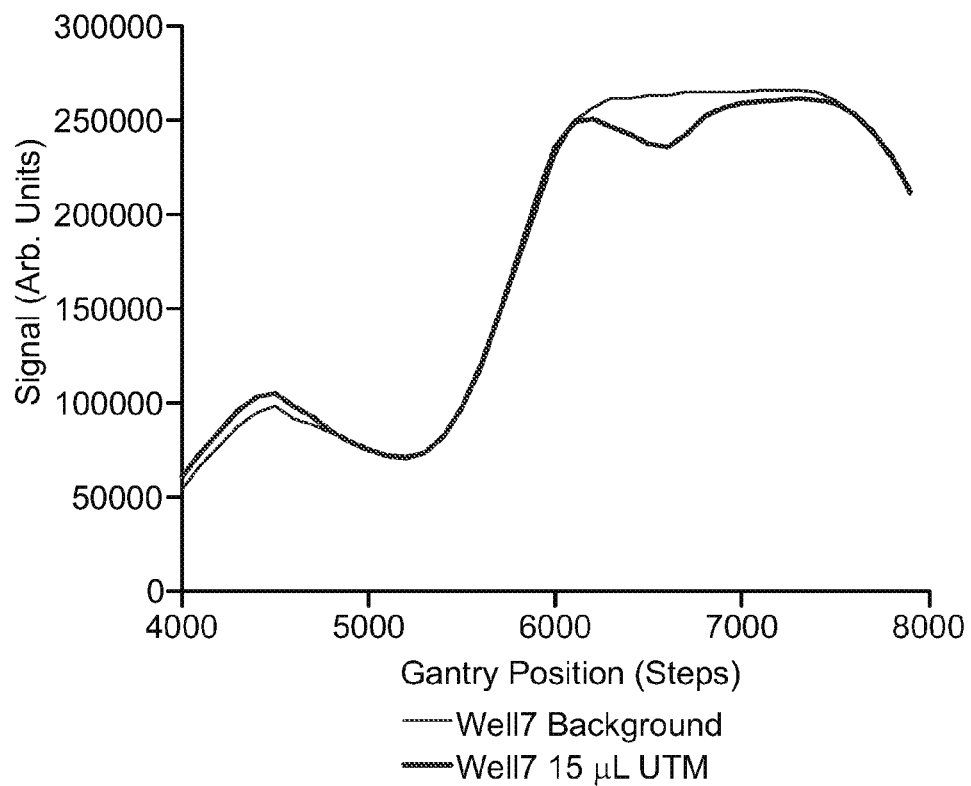
Figure 30:
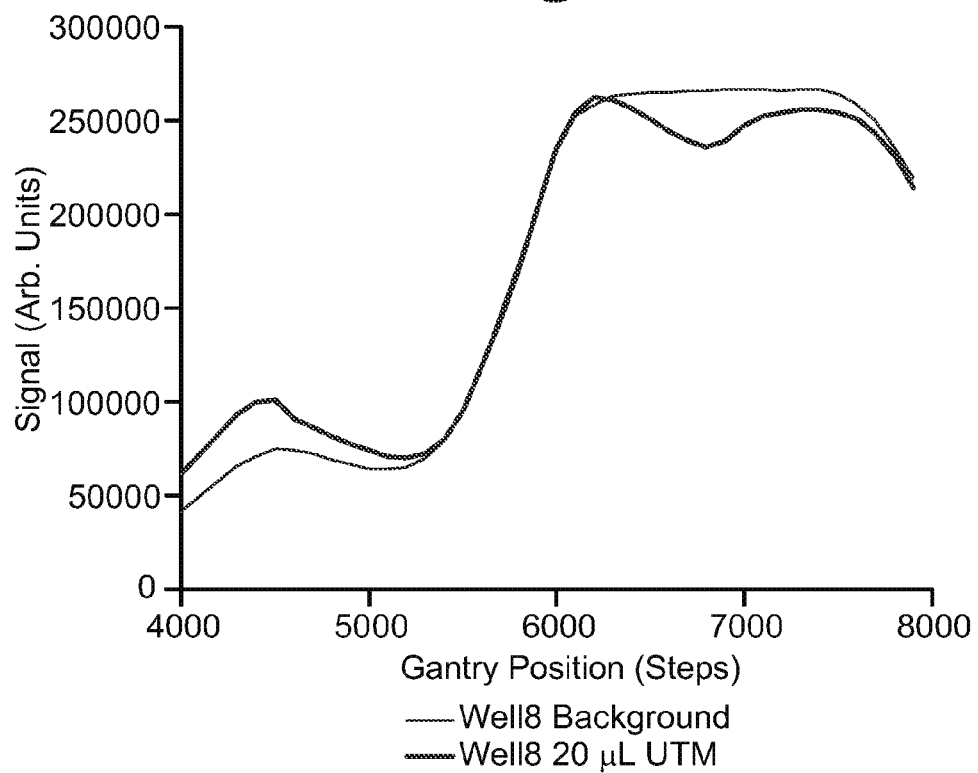

It should be noted that the process 600 of FIG. 26 can be employed in one lane 303 at a time on the disk 300, or one or more lanes can be loaded and processed simultaneously according to the process 600 of FIG. 26.

The following embodiments of the present disclosure are intended to be illustrative and not limiting.

EMBODIMENTS

Embodiment 1 is a method for processing sample processing devices, the method comprising:
  providing a sample processing device comprising a detection chamber;
  rotating the sample processing device about an axis of rotation; and
  determining whether a selected volume of material is present in the detection chamber, while rotating the sample processing device.

Embodiment 2 is the method of embodiment 1, wherein determining whether a selected volume of material is present in the detection chamber includes determining whether a selected volume of a sample is present in the detection chamber.

Embodiment 3 is the method of embodiment 1, wherein determining whether a selected volume of material is present in the detection chamber includes determining whether a selected total volume of a sample and a reagent medium is present in the detection chamber.

Embodiment 4 is the method of any of embodiments 1-3, wherein determining whether a selected volume of material is present in the detection chamber includes optically interrogating the detection chamber at a selected position to determine whether the material is present at the selected position.

Embodiment 5 is the method of any of embodiments 1-4, wherein determining whether a selected volume of material is present in the detection chamber includes optically interrogating the detection chamber for an optical property of a sample to determine whether the sample is present in the detection chamber.

Embodiment 6 is the method of any of embodiments 1-5, wherein the detection chamber includes an inner boundary located nearest the axis of rotation, and wherein determining whether a selected volume of material is present in the detection chamber includes optically interrogating the detection chamber at a gantry position proximate the inner boundary of the detection chamber.

Embodiment 7 is the method of any of embodiments 4-6, wherein optically interrogating the detection chamber includes optically interrogating the detection chamber for a meniscus.

Embodiment 8 is the method of any of embodiments 4-7, wherein optically interrogating the detection chamber includes
emitting an electromagnetic signal into the detection chamber, and
obtaining a scan by detecting backscattered reflection of the electromagnetic signal, after emitting the electromagnetic signal into the detection chamber.

Embodiment 9 is the method of embodiment 8, wherein obtaining a scan includes:
obtaining a first background scan of the detection chamber,
obtaining a second scan of the detection chamber after positioning a sample in the detection chamber, and
comparing the first background scan with the second scan to determine whether a selected volume of the sample is located in the detection chamber.

Embodiment 10 is the method of embodiment 9, wherein comparing the first background scan with the second scan to determine whether a selected volume of the sample is located in the detection chamber includes determining whether a threshold change exists between the first background scan and the second scan.

Embodiment 11 is the method of embodiment 10, further comprising providing an optical module operatively positioned relative to the sample processing device on a gantry, wherein optically interrogating the detection chamber includes optically interrogating the detection chamber with the optical module at a plurality of radial positions, relative to the axis of rotation.

Embodiment 12 is the method of embodiment 11, further comprising:
determining a radial position at which a threshold change is found between the first background scan and the second scan; and
using the radial position to determine the volume of the sample that is located in the detection chamber.

Embodiment 13 is the method of any of embodiments 8-12, wherein obtaining a scan by detecting backscattered reflection of the electromagnetic signal is performed using a FAM optical channel.

Embodiment 14 is the method of any of embodiments 4-7, wherein optically interrogating includes
emitting an electromagnetic signal into the detection chamber, and
obtaining a scan by detecting fluorescence emitted by a material in the detection chamber, after emitting the electromagnetic signal into the detection chamber.

Embodiment 15 is the method of embodiment 14, wherein obtaining a scan includes:
obtaining a first background scan of the detection chamber,
obtaining a second scan of the detection chamber after positioning a sample in the detection chamber, and
comparing the first background scan with the second scan to determine whether a selected volume of the sample is present in the detection chamber.

Embodiment 16 is the method of embodiment 15, wherein comparing the first background scan with the second scan to determine whether a selected volume of the sample is located in the detection chamber includes determining whether a threshold change in fluorescence exists between the first background scan and the second scan.

Embodiment 17 is the method of embodiment 16, further comprising providing an optical module operatively positioned relative to the sample processing device on a gantry, wherein interrogating the detection chamber includes optically interrogating the detection chamber with the optical module at a plurality of radial positions, relative to the axis of rotation.

Embodiment 18 is the method of embodiment 17, further comprising:
determining a radial position at which a threshold change in fluorescence is found between the first background scan and the second scan; and
using the radial position to determine the volume of the sample that is present in the detection chamber.

Embodiment 19 is the method of any of embodiments 1-18, further comprising:
heating the detection chamber,
wherein determining whether a selected volume of material is present in the detection chamber occurs while heating the detection chamber.

Embodiment 20 is the method of any of embodiments 4-19, wherein optically interrogating includes
emitting an electromagnetic signal into the detection chamber at a first wavelength, and
detecting electromagnetic signals emitted from the detection chamber at a second wavelength, after emitting the electromagnetic into the detection chamber at a first wavelength.

Embodiment 21 is the method of any of embodiments 4-20, wherein material includes a sample to be analyzed and reagent media, and wherein optically interrogating the detection chamber includes optically interrogating the detection chamber for an optical property of at least one of the sample and the reagent media in the detection chamber.

Embodiment 22 is the method of any of embodiments 4-21, further comprising providing an optical module operatively positioned relative to the sample processing device on a gantry, and wherein optically interrogating the detection chamber includes optically interrogating the detection chamber with the optical module located at a predetermined gantry position.

Embodiment 23 is the method of any of embodiments 4-21, further comprising providing an optical module operatively positioned relative to the sample processing device on a gantry, and wherein optically interrogating the detection chamber includes optically interrogating the detection chamber with the optical module at a plurality of gantry positions.

Embodiment 24 is the method of embodiment 23, wherein each of the plurality of gantry positions is associated with an amount of material, and further comprising:
detecting a threshold signal at a gantry position; and
correlating the gantry position to an amount of material that is present in the detection chamber.

Embodiment 25 is the method of embodiment 23 or 24, wherein the plurality of gantry positions includes different radial positions in the detection chamber, relative to the axis of rotation.

Embodiment 26 is the method of any of embodiments 23-25, wherein a first gantry position is positioned radially outwardly of a second gantry position.

Embodiment 27 is the method of any of embodiments 11-12, 17-18 and 22-26, wherein the optical module is configured for multiplex fluorescence detection.

Embodiment 28 is the method of any of embodiments 1-27, wherein the sample processing device includes a plurality of detection chambers, and wherein optically interrogating the detection chamber includes optically interrogating at least one of the plurality of detection chambers while rotating the sample processing device.

Embodiment 29 is the method of any of embodiments 1-28, wherein rotating the sample processing device while determining whether a selected volume of material is present in the detection chamber forces any material present in the detection chamber to a position in the detection chamber that is located furthest from the axis of rotation.

Embodiment 30 is the method of any of embodiments 1-29, wherein the detection chamber includes an outer boundary positioned furthest from the axis of rotation, and wherein rotating the sample processing device while determining whether a selected volume of material is present in the detection chamber forces any material present in the detection chamber toward the outer boundary of the detection chamber.

Embodiment 31 is the method of any of embodiments 1-30, wherein the sample processing device comprises a processing array comprising:
an input chamber,
the detection chamber, and
a channel positioned to fluidly couple the input chamber and the detection chamber; and further comprising:
positioning a sample in the input chamber of the sample processing device;
wherein rotating the sample processing device about an axis of rotation causes the sample to move to the detection chamber.

Embodiment 32 is the method of embodiment 31, wherein the sample processing device further includes a valve positioned in the channel, such that the input chamber and the detection chamber are not in fluid communication via the channel when the valve is closed and are in fluid communication via the channel when the valve is open, and further comprising opening the valve, wherein rotating the sample processing device about an axis of rotation to move the sample to the detection chamber occurs after opening the valve.

Embodiment 33 is the method of embodiment 31 or 32, wherein rotating the sample processing device about an axis of rotation to move the sample to the detection chamber includes metering a selected amount of the sample to the detection chamber.

Embodiment 34 is the method of any of embodiments 31-33, wherein rotating the sample processing device about an axis of rotation to move the sample to the detection chamber includes moving a reagent medium to the detection chamber.

Embodiment 35 is the method of any of embodiments 1-34, wherein determining whether a selected volume of material is present in the detection chamber includes optically interrogating the detection chamber.

Embodiment 36 is a method for processing sample processing devices, the method comprising:
providing a sample processing device comprising a detection chamber;
rotating the sample processing device about an axis of rotation; and
optically interrogating the detection chamber for an optical property of a material to determine whether the material is present in the detection chamber, wherein optically interrogating occurs while rotating the sample processing device.

Embodiment 37 is the method of embodiment 36, wherein the detection chamber forms a portion of a processing array in the sample processing device, and further comprising positioning a sample in the processing array of the sample processing device.

Embodiment 38 is the method of embodiment 36, wherein rotating the sample processing device about an axis of rotation causes the sample to move to the detection chamber.

Embodiment 39 is a method for processing sample processing devices, the method comprising:
providing a sample processing device comprising a processing array, the processing array comprising:
an input chamber,
a detection chamber, and
a channel positioned to fluidly couple the input chamber and the detection chamber;
positioning a sample in the input chamber of the processing array of the sample processing device;
rotating the sample processing device about an axis of rotation to move the sample to the detection chamber;
after rotating the sample processing device to move the sample to the detection chamber, optically interrogating the detection chamber for an optical property of the sample to determine whether the sample has moved to the detection chamber; and
rotating the sample processing device while optically interrogating the detection chamber.

Embodiment 40 is the method of embodiment 39, wherein the sample processing device further includes a valve positioned in the channel, such that the input chamber and the detection chamber are not in fluid communication via the channel when the valve is closed and are in fluid communication via the channel when the valve is open, and further comprising opening the valve, wherein rotating the sample processing device about an axis of rotation to move the sample to the detection chamber occurs after opening the valve.

Embodiment 41 is the method of embodiment 39 or 40, wherein rotating the sample processing device about an axis of rotation to move the sample to the detection chamber includes metering a selected amount of the sample to the detection chamber.

Embodiment 42 is the method of any of embodiments 39-41, wherein rotating the sample processing device about an axis of rotation to move the sample to the detection chamber includes moving a reagent medium to the detection chamber.

Embodiment 43 is the method of any of embodiments 39-42, wherein rotating the sample processing device while optically interrogating the detection chamber forces any material present in the detection chamber to a position in the detection chamber that is located furthest from the axis of rotation.

Embodiment 44 is the method of any of embodiments 39-43, wherein the detection chamber includes an outer boundary positioned furthest from the axis of rotation, and wherein rotating the sample processing device while optically interrogating the detection chamber forces any material present in the detection chamber toward the outer boundary of the detection chamber.

Embodiment 45 is the method of any of embodiments 39-44, wherein the sample processing device is continuously rotated from the first rotating step through the second rotating step, such that the sample processing device is not stopped from rotating between the rotating steps.

Embodiment 46 is the method of any of embodiments 39-45, wherein optically interrogating the detection chamber includes optically interrogating the detection chamber for a meniscus.

Embodiment 47 is the method of any of embodiments 39-46, wherein optically interrogating the detection chamber includes
  emitting an electromagnetic signal into the detection chamber, and
  obtaining a scan by detecting backscattered reflection of the electromagnetic signal, after emitting the electromagnetic signal into the detection chamber.

Embodiment 48 is the method of embodiment 47, wherein obtaining a scan includes:
  obtaining a first background scan of the detection chamber before rotating the sample processing device to move the sample to the detection chamber,
  obtaining a second scan of the detection chamber after rotating the sample processing device to move the sample to the detection chamber, and
  comparing the first background scan with the second scan to determine whether a selected volume of the sample is located in the detection chamber.

Embodiment 49 is the method of embodiment 48, wherein comparing the first background scan with the second scan to determine whether a selected volume of the sample is located in the detection chamber includes determining whether a threshold change exists between the first background scan and the second scan.

Embodiment 50 is the method of embodiment 49, further comprising providing an optical module operatively positioned relative to the sample processing device, wherein optically interrogating the detection chamber includes optically interrogating the detection chamber with the optical module at a plurality of radial positions, relative to the axis of rotation.

Embodiment 51 is the method of embodiment 50, further comprising:
  determining a radial position at which a threshold change is found between the first background scan and the second scan; and
  using the radial position to determine the amount of the sample that is present in the detection chamber.

Embodiment 52 is the method of any of embodiments 47-51, wherein obtaining a scan by detecting backscattered reflection of the electromagnetic signal is performed using a FAM optical channel.

Embodiment 53 is the method of any of embodiments 39-46, wherein optically interrogating includes
  emitting an electromagnetic signal into the detection chamber, and
  obtaining a scan by detecting fluorescence emitted by a material in the detection chamber, after emitting the electromagnetic signal into the detection chamber.

Embodiment 54 is the method of embodiment 53, wherein obtaining a scan includes:
  obtaining a first background scan of the detection chamber before rotating the sample processing device to move the sample to the detection chamber,
  obtaining a second scan of the detection chamber after rotating the sample processing device to move the sample to the detection, and
  comparing the first background scan with the second scan to determine whether a selected volume of the sample is present in the detection chamber.

Embodiment 55 is the method of embodiment 54, wherein comparing the first background scan with the second scan to determine whether a selected volume of the sample is present in the detection chamber includes determining whether a threshold change in fluorescence exists between the first background scan and the second scan.

Embodiment 56 is the method of embodiment 55, further comprising providing an optical module operatively positioned relative to the sample processing device, wherein optically interrogating the detection chamber includes optically interrogating the detection chamber with the optical module at a plurality of radial positions, relative to the axis of rotation.

Embodiment 57 is the method of embodiment 56, further comprising:
  determining a radial position at which a threshold change in fluorescence is found between the first background scan and the second scan; and
  using the radial position to determine the amount of the sample that is present in the detection chamber.

Embodiment 58 is the method of any of embodiments 39-57, further comprising:
  heating the detection chamber,
  wherein determining whether a selected volume of material is present in the detection chamber occurs while heating the detection chamber.

Embodiment 59 is the method of any of embodiments 38-58, wherein optically interrogating includes
  emitting an electromagnetic signal into the detection chamber at a first wavelength, and
  detecting electromagnetic signals emitted from the detection chamber at a second wavelength, after emitting the electromagnetic signal into the detection chamber at a first wavelength.

Embodiment 60 is the method of any of embodiments 39-59, wherein the sample includes a sample to be analyzed and reagent media, and wherein optically interrogating the detection chamber includes optically interrogating the detection chamber for an optical property of at least one of the sample and the reagent media in the detection chamber.

Embodiment 61 is the method of any of embodiments 39-60, further comprising providing an optical module operatively positioned relative to the sample processing device on a gantry, and wherein optically interrogating the detection chamber includes optically interrogating the detection chamber with the optical module located at a predetermined gantry position.

Embodiment 62 is the method of any of embodiments 39-61, further comprising providing an optical module operatively positioned relative to the sample processing device on a gantry, and wherein optically interrogating the detection chamber includes optically interrogating the detection chamber with the optical module at a plurality of gantry positions.

Embodiment 63 is the method of embodiment 62, wherein each of the plurality of gantry positions is associated with an amount of material, and further comprising:
detecting a threshold signal at a gantry position; and
correlating the gantry position to an amount of material that is present in the detection chamber.

Embodiment 64 is the method of embodiment 62 or 63, wherein the plurality of gantry positions includes different radial positions in the detection chamber, relative to the axis of rotation.

Embodiment 65 is the method of any of embodiments 62-64, wherein a first gantry position is positioned radially outwardly of a second gantry position.

Embodiment 66 is the method of any of embodiments 50-51, 56-57 and 61-65, wherein the optical module is configured for multiplex fluorescence detection.

Embodiment 67 is the method of any of embodiments 39-66, further comprising optically interrogating the detection chamber to determine an amount of sample that is present in the detection chamber.

Embodiment 68 is the method of any of embodiments 39-67, wherein the sample processing device includes a plurality of processing arrays and a plurality of detection chambers, and wherein optically interrogating the detection chamber includes optically interrogating at least one of the plurality of detection chambers while rotating the sample processing device.

Embodiment 69 is a method for processing sample processing devices, the method comprising:
providing a sample processing device comprising a processing array, the processing array comprising:
an input chamber,
a detection chamber, and
a channel positioned to fluidly couple the input chamber and the detection chamber;
positioning a sample in the input chamber of at least one processing array in the sample processing device;
rotating the sample processing device about an axis of rotation to move the sample to the detection chamber;
optically interrogating the detection chamber of the processing array before rotating the sample processing device to move the sample to the detection chamber to obtain a first background scan;
optically interrogating the detection chamber of the processing array to obtain a second scan after rotating the sample processing device to move the sample to the detection chamber;
rotating the sample processing device about the axis of rotation while optically interrogating the detection chamber to obtain the second scan; and
comparing the first background scan with the second scan to determine if a threshold change exists between the first background scan and the second scan.

Embodiment 70 is the method of embodiment 69, wherein optically interrogating the detection chamber to generate a first background scan and optically interrogating the detection chamber to generate a second scan occur at the same temperature.

Embodiment 71 is a system for processing sample processing devices, the system comprising:
a sample processing device comprising a detection chamber;
a motor configured to rotate the sample processing device about an axis of rotation;
an optical module operatively positioned relative to the sample processing device and configured to determine whether a selected volume of material is present in the detection chamber of the sample processing device.

Embodiment 72 is the system of embodiment 71, wherein the optical module is configured to determine whether a selected volume of material is present in the detection chamber while the motor rotates the sample processing device about the axis of rotation.

Embodiment 73 is the system of embodiment 71 or 72, wherein the optical module includes a plurality of optical channels, and wherein at least one of the optical channels is configured to determined whether a selected volume of material is present in the detection chamber of the sample processing device.

Embodiment 74 is the system of any of embodiments 71-73, wherein the sample processing device further includes
an input chamber, and
a channel positioned to fluidly couple the input chamber and the detection chamber.

Embodiment 75 is the system of embodiment 74, wherein the sample processing device further includes a valve positioned in the channel, wherein when the valve is closed, the input chamber and the detection chamber are not in fluid communication via the channel, and wherein when the valve is open, the input chamber and the detection chamber are in fluid communication via the channel.

Embodiment 76 is the system of embodiment 74 or 75, wherein the input chamber includes a metering chamber configured to meter a selected amount of a sample to the detection chamber.

Embodiment 77 is the system of any of embodiments 71-76, wherein the optical module is operatively positioned relative to the sample processing device via a gantry, and wherein the optical module is configured to be positioned at a plurality of gantry positions, relative to the axis of rotation, and is further configured to optically interrogate the detection chamber at a plurality of gantry positions.

Embodiment 78 is the system of embodiment 77, wherein the plurality of gantry positions correspond to different radial positions in the detection chamber, relative to the axis of rotation.

Embodiment 79 is the system of embodiment 77 or 78, wherein a first gantry position is positioned radially outwardly of a second gantry position.

Embodiment 80 is the system of any of embodiments 71-76, wherein the optical module is operatively positioned relative to the sample processing device via a gantry, and wherein the optical module is configured to be positioned at a predetermined gantry position, relative to the axis of rotation, and is further configured to optically interrogate the detection chamber at the predetermined gantry position.

Embodiment 81 is the system of embodiment 80, wherein the detection chamber includes an inner boundary located nearest the axis of rotation, and wherein the optical module is configured to optically interrogate the detection chamber at a gantry position proximate the inner boundary of the detection chamber.

Embodiment 82 is the system of any of embodiments 71-81, wherein the optical module is configured to optically interrogate the detection chamber to determine whether a selected volume of material is present in the detection chamber.

Embodiment 83 is the system of any of embodiments 71-82, wherein the optical module is configured for multiplex fluorescence detection.

Embodiment 84 is the system of any of embodiments 71-83, wherein the optical module is configured to determine whether a selected volume of material is present in the detection chamber by
emitting an electromagnetic signal into the detection chamber, and
detecting backscattered reflection of the electromagnetic signal.

Embodiment 85 is the system of any of embodiments 71-84, wherein the optical module is configured to determine whether a selected volume of material is present in the detection chamber by
emitting an electromagnetic signal into the detection chamber, and
detecting fluorescence emitted by a material in the detection chamber.

Embodiment 86 is the system of any of embodiments 71-85, wherein the optical module is configured to determine whether a selected volume of material is present in the detection chamber by
emitting an electromagnetic signal into the detection chamber at a first wavelength, and
detecting electromagnetic signals emitted from the detection chamber at a second wavelength, after emitting an electromagnetic signal into the detection chamber at a first wavelength.

Embodiment 87 is the system of any of embodiments 71-86, wherein the optical module is further configured to determine an amount of material that is present in the detection chamber.

The following working examples are intended to be illustrative of the present disclosure and not limiting.

EXAMPLES

Example 1

Example 1 demonstrated direct sample (fluid) detection in detection chambers of a Channel Development Disk.
Materials:
Sample: Copan Universal Transport Medium (UTM) for Viruses, *Chlamydia, Mycoplasma,* and *Ureaplasma,* 3.0 ml tube, part number 330C, lot 39P505 (Copan Diagnostics, Murrietta, Ga.).
Equipment:
A "Channel Development Disk," described above and shown in FIG. 23, available from 3M Company of St. Paul, Minn., was used as the sample processing device or "disk" in this example. An Integrated Cycler Model 3954, available from 3M Company of St. Paul, Minn. was used with the Channel Development Disk as the sample processing system or "instrument" in this example. The instrument contained a FAM module (blue LED, 475 nm excitation filter, 520 nm detection filter).
Procedure for Sample Fluid Detection Analysis on Channel Development Disk:
1. Added empty Channel Development Disk to the Integrated Cycler instrument.
2. Performed laser homing according to the method described above with respect to FIG. 14.
3. Performed background scan of all detection chambers; initial gantry=4000 to final gantry=8000; step size=100; set point temperature=25° C., using the FAM module.
4. Stopped disk and removed disk from instrument.
5. Added various amounts of UTM sample to different lanes on the disk:
    a. Lane 5: 5 µL transport medium
    b. Lane 6: 10 µL transport medium
    c. Lane 7: 15 µL transport medium
    d. Lane 8: 20 µL transport medium
6. Replaced loaded disk back onto instrument.
7. Performed laser homing, again according to the method described above with respect to FIG. 14.
8. Loaded fluid into detection chambers via rotation of the disk, according to the following rotation scheme: 5 cycles of
    a. Accelerated to 4500 rpm at an acceleration of 244 revolutions/sec$^2$.
    b. Held at 4500 for 1 sec.
    c. Decelerated to 750 rpm at a deceleration of 244 revolutions/sec$^2$.
    d. Held at 750 rpm for 1 sec.
9. Performed sample detection scan; initial gantry=4000 to final gantry=9000; step size=100; set point temperature=25° C., using the FAM module.
See FIG. 27: 5 µL UTM in detection chamber of Lane #5
See FIG. 28: 10 µL UTM in detection chamber of Lane #6
See FIG. 29: 15 µL UTM in detection chamber of Lane #7
See FIG. 30: 20 µL UTM in detection chamber of Lane #8

FIGS. 27-30 represent meniscus detection results for samples of 5 µL, 10 µL, 15 µL and 20 µL, respectively. Each of the plots is a scan of backscattered intensity (arbitrary units) versus gantry position, with the gantry moving radially inwardly, such that gantry position increases as the gantry was moved from a radially outward position to a radially inward position. The meniscus caused a refraction of the excitation light beam and in the backscattered intensity, which appeared as a dip between gantry positions 6000-7000. The largest and most reliable measurement was acquired in the FAM module. The magnitude of the dips varied from 10-15% from the value of the background scan. The result for 5 µL of sample, shown in FIG. 27, indicated that at this low level of fluid, the meniscus cannot be reliably detected. However, at sample fluid levels of 10 µL, 15 µL and 20 µL, the meniscus can be detected.

Example 2

Example 2 was the determination of optimal gantry position and threshold for automatically detecting a 10-µL sample in a Moderate Complexity Disk.
Materials:
Sample: Copan Universal Transport Medium (UTM) for Viruses, *Chlamydia, Mycoplasma,* and *Ureaplasma,* 3.0 ml tube, part number 330C, lot 39P505 (Copan Diagnostics, Murrietta, Ga.).
Equipment:
An Integrated Cycler instrument, model 3954, containing a FAM module (blue LED, 475 nm excitation filter, 520 nm detection filter), available from 3M Company of St. Paul, Minn., and two "Moderate Complexity Disks," described above and shown in FIGS. 16-22, available as Product No. 3958 from 3M Company of St. Paul, Minn., were used as the sample processing device or "disk" in this example. The first disk, representing the "sample present" case, was loaded with 50 µL UTM in the sample port of lanes 1-8. The second disk, representing the "sample absent" case, was not loaded with any material. Both disks were processed identically with the following procedure:
1. Placed the disk onto the Integrated Cycler instrument.
2. Performed metering: The disk was rotated at 525 rpm with an acceleration of 24.4 revolutions/sec$^2$, held for 5 seconds, then rotated at 975 rpm with an acceleration of 24.4 revolutions/sec$^2$, and held for 5 seconds.

3. Performed laser homing, according to the process shown in FIG. 14 and described above. The laser used was a high power density laser diode, part number SLD323V, available from Sony Corporation, Tokyo, Japan.
4. Performed background scan of detection chambers as a function of gantry position (initial gantry=4000, final gantry=9000, step size=100) using the FAM module.
5. Stopped the motor and opened sample valves with one laser pulse at 2 seconds at 800 milliwatts (mW), according to the process shown in FIG. 12 and described above.
6. Transferred sample to detection chambers by rotating the disk at 1800 rpm with an acceleration of 24.4 revolutions/sec$^2$, and held for 10 seconds.
7. Scanned the detection chambers as a function of gantry position, using the FAM module; initial gantry=4000, final gantry=9000, step size=100.

For each detection chamber on each disk, the percent change of the signal from the background was calculated as a function of gantry position for the FAM module. A portion of the data at the different gantry positions is shown in Table 1 below. Each detection chamber on disk 1 (sample present) had the largest change of signal at gantry position 5900. Each detection chamber on disk 2 (sample absent) had a negligible percent change at gantry position 5900; in fact a negligible percent change at all the gantry positions. The average and standard deviations of the data from each disk was calculated and is shown in Tables 1 and 2, below.

TABLE 1

EXAMPLE 1 Disk 1 "Sample present"

| Detection Chamber | Gantry 5500 % change | Gantry 5700 % change | Gantry 5900 % change | Gantry 6100 % change | Gantry 6300 % change |
|---|---|---|---|---|---|
| 1 | 6.960 | 11.149 | 10.631 | 8.857 | 2.209 |
| 2 | 5.163 | 11.073 | 9.973 | 8.348 | 4.544 |
| 3 | 6.313 | 11.801 | 13.427 | 11.158 | 4.362 |
| 4 | 8.702 | 13.634 | 15.807 | 13.501 | 6.661 |
| 5 | 7.597 | 13.229 | 12.334 | 10.111 | 4.197 |
| 6 | 5.860 | 12.138 | 12.736 | 10.953 | 4.114 |
| 7 | 6.077 | 10.364 | 11.266 | 9.229 | 1.095 |
| 8 | 6.395 | 12.319 | 12.208 | 9.661 | 3.010 |
| average | 6.633 | 11.963 | 12.298 | 10.227 | 3.774 |
| st dev | 1.105 | 1.108 | 1.814 | 1.641 | 1.681 |

TABLE 2

EXAMPLE 1 Disk 2 "Sample absent"

| Detection Chamber | Gantry 5500 % change | Gantry 5700 % change | Gantry 5900 % change | Gantry 6100 % change | Gantry 6300 % change |
|---|---|---|---|---|---|
| 1 | 0.180 | 0.220 | 0.201 | 0.017 | 0.947 |
| 2 | 0.309 | 0.954 | 1.134 | 0.915 | 0.985 |
| 3 | 1.595 | 2.079 | 1.411 | 1.275 | 0.939 |
| 4 | 0.991 | 2.122 | 1.360 | 0.888 | 0.073 |
| 5 | 2.578 | 2.177 | 1.384 | 0.981 | 0.150 |
| 6 | 0.229 | 1.472 | 0.803 | 0.903 | 0.067 |
| 7 | 0.826 | 0.510 | 0.763 | 0.739 | 0.694 |
| 8 | 0.752 | 0.200 | 0.377 | 0.062 | 1.036 |
| average | 0.933 | 1.217 | 0.929 | 0.722 | 0.611 |
| st dev | 0.815 | 0.857 | 0.470 | 0.448 | 0.439 |

The data shows a significant difference between the sample present and sample absent disks. A threshold value for automatically detecting the presence of sample in a clinical assay at the optimal gantry position of 5900 was calculated by subtracting 3 standard deviations from the average value of percent change at gantry position 5900, for disk 1. The threshold value calculated was 12.298−(3× 1.814)=6.85.

Example 3

Example 3 demonstrated two different fluid detection approaches on a Moderate Complexity Disk with a fluorescent reagent master mix.

Materials:

Sample: Copan Universal Transport Medium (UTM) for Viruses, *Chlamydia, Mycoplasma*, and *Ureaplasma*, 3.0 ml tube, part number 330C, lot 39P505 (Copan Diagnostics, Murrietta, Ga.).

Reagent master mix: Applied Biosystems (Foster City, Calif.) 10× PCR buffer, P/N 4376230, lot number 1006020, diluted to 1× with nuclease-free water, spiked with ROX Reference Dye, Invitrogen (Carlsbad, Calif.) P/N 12223-012, lot number 786140. The final dye concentration was 800 nM.

Equipment:

A "Moderate Complexity Disk," described above and shown in FIGS. 16-22, available as Product No. 3958 from 3M Company of St. Paul, Minn., was used as the sample processing device or "disk" in this example.

An Integrated Cycler Model 3954, with FAM module (see Examples 1 and 2) and CFR610 module (yellow LED, 580 nm excitation filter, and 610 nm emission filter), available from 3M Company of St. Paul, Minn., was used as the sample processing system or "instrument" in this example.

Procedure for Sample and Total Fluid Detection on Moderate Complexity Disk:

1. Loaded each lane of the disk in the following manner:

TABLE 3

| Lane | Sample Input | Reagent Input |
|---|---|---|
| 1 | 50 µL UTM | Empty |
| 2 | 50 µL UTM | Empty |
| 3 | Empty | 50 µL PCR buffer with ROX |
| 4 | Empty | 50 µL PCR buffer with ROX |
| 5 | 50 µL UTM | 50 µL PCR buffer with ROX |
| 6 | 50 µL UTM | 50 µL PCR buffer with ROX |
| 7 | Empty | Empty |
| 8 | Empty | Empty |

2. Positioned the loaded disk onto the instrument.
3. Metered sample and reagent fluids (10 µL sample and 40 µL reagent) into the metering reservoirs by the following procedure: the disk was rotated at 525 rpm with an acceleration of 24.4 revolutions/sec$^2$, held for 5 seconds, then rotated at 975 rpm with an acceleration of 24.4 revolutions/sec$^2$, and held for 5 seconds.
4. Performed laser homing, according the process shown in FIG. 14 and described above. The laser used was a high power density laser diode, part number SLD323V, available from Sony Corporation, Tokyo, Japan.
5. Performed background scan of detection chambers as a function of gantry position (initial gantry=4000, final gantry=9000, step size=100) using the FAM module.
6. Stopped motor and opened sample septum valves with one laser pulse at 2 seconds at 800 mW, according to the process shown in FIG. 12 and described above.
7. Transferred UTM sample to detection chambers by rotating the disk at 1800 rpm with an acceleration of 24.4 revolutions/sec$^2$, and held for 10 seconds.

8. Scanned the detection chambers as a function of gantry position, using the FAM module; initial gantry=4000, final gantry=9000, step size=100.
9. Stopped motor and opened reagent septum valves with one laser pulse at 2 seconds at 800 mW, according to the method described above with respect to FIG. 12.
10. Transferred PCR buffer+ROX reagent to detection chambers by rotating the disk at 2250 rpm with an acceleration of 244 revolutions/sec$^2$, and held for 10 seconds.
11. Scanned detection chambers as a function of gantry position using the CFR610 module (initial gantry=4000, final gantry=9000, step size=100).

Approach 1: Sample-Only Meniscus Detection Using the FAM Module

After the sample was transferred to the detection chamber (Step 7), the data collected in Step 8 was used to calculate the percent change in the backscattered intensity at the meniscus level at gantry position 5900. The threshold of 6.85 for automatically detecting the presence of sample in the detection chamber, determined in Example 2, was applied to the percent change results shown in Table 4. The presence and absence of sample in the detection chamber were accurately determined as shown by the results in Table 4.

TABLE 4

Sample meniscus detection, FAM module, Gantry position 5900

| Lane No. | Detection Chamber Contents after step 8 | % change of backscattered intensity | % change greater than 6.85? |
| --- | --- | --- | --- |
| 1 | 10 µL UTM | 12.060 | Yes |
| 2 | 10 µL UTM | 10.995 | Yes |
| 3 | empty | 3.197 | No |
| 4 | empty | 2.962 | No |
| 5 | 10 µL UTM | 11.516 | Yes |
| 6 | 10 µL UTM | 10.549 | Yes |
| 7 | Empty | 0.947 | No |
| 8 | Empty | 1.684 | No |

Approach 2: Total Fluid Detection (Aample+Reagent) Using the CFR610 Module

The data for the CFR610 module acquired from Step 11 was processed for a total fluid level detection. In this case, the signal was fluorescence from the ROX dye in the buffer. There was no signal in the sample-only and empty detection chambers. The signal detected from the reagent only (PCR buffer+ROX) peaked higher and at a lower gantry position with respect to the sample+reagent cases because of the dilution effect of 10 µL sample being added to the 40 µL buffer, and the higher volume reaching closer to the inner edge of the detection chambers. FIG. 31 illustrates this example, showing, for example, the large % increase for detection chambers 3 and 5 compared to detection chambers 1 and 7. Lanes 2, 4, 6 and 8 were omitted in FIG. 31, since they were replicates of lanes 1, 3, 5 and 7, respectively.

A series of disks with detection chambers containing either (i) the PCR buffer+ROX or (ii) PCR buffer+ROX and sample were used to determine the optimal gantry position and threshold for delineating the cases of reagent vs. reagent+sample chambers, following a process similar to that of Example 2. The optimal gantry position was determined as the position at which there was the greatest difference in signal between reagent-only chambers and reagent+sample chambers. The optimal gantry position was determined to be 7600, and the threshold was determined to be 1398%. At a gantry position of 7600 and using a threshold of 1398%, the presence of total fluid of 50 µL in detection chambers 3 and 4, was accurately detected. Detection chambers 1 & 2 containing 10 µL sample (UTM) only; detection chambers 3 & 4 containing 40 µL reagent (PCR buffer+ROX) only; and empty detection chambers 7 & 8, all had percent change values below the 1398 threshold and thus were designated as not having the correct total fluid level. Table 5 shows the results of applying the total fluid level detection approach to the disk in Example 3 using the gantry position=7600.

TABLE 5

Total fluid level detection using fluorescence, CFR610, Gantry 7600

| Lane No. | Detection Chamber Contents after step 11 | % change of backscattered intensity | % change greater than 1398? |
| --- | --- | --- | --- |
| 1 | 10 µL UTM sample | 6.093 | No |
| 2 | 10 µL UTM sample | 8.428 | No |
| 3 | 40 µL buffer | 125.765 | No |
| 4 | 40 µL buffer | 611.584 | No |
| 5 | 10 µL UTM sample + 40 µL buffer | 2731.890 | Yes |
| 6 | 10 µL UTM sample + 40 µL buffer | 2608.653 | Yes |
| 7 | Empty | 9.336 | No |
| 8 | Empty | 4.572 | No |

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure.

All references and publications cited herein are expressly incorporated herein by reference in their entirety into this disclosure.

Various features and aspects of the present disclosure are set forth in the following claims.

What is claimed is:

1. A system for processing sample processing devices, the system comprising:
   a sample processing device comprising a detection chamber;
   a motor configured to rotate the sample processing device about an axis of rotation;
   an optical module operatively positioned relative to the sample processing device and configured to determine whether a selected volume of material is present in the detection chamber of the sample processing device while the motor rotates the sample processing device about the axis of rotation.

2. The system of claim 1, wherein the optical module includes a plurality of optical channels, and wherein at least one of the optical channels is configured to determine whether a selected volume of material is present in the detection chamber of the sample processing device.

3. The system of claim 1, wherein the sample processing device further includes
   an input chamber, and
   a channel positioned to fluidly couple the input chamber and the detection chamber.

4. The system of claim 3, wherein the sample processing device further includes a valve positioned in the channel, wherein when the valve is closed, the input chamber and the detection chamber are not in fluid communication via the channel, and wherein when the valve is open, the input chamber and the detection chamber are in fluid communication via the channel.

5. The system of claim 3, wherein the input chamber includes a metering chamber configured to meter a selected amount of a sample to the detection chamber.

6. The system of claim 1, wherein the optical module is operatively positioned relative to the sample processing device via a gantry, and wherein the optical module is configured to be positioned at a plurality of gantry positions, relative to the axis of rotation, and is further configured to optically interrogate the detection chamber at a plurality of gantry positions.

7. The system of claim 6, wherein the plurality of gantry positions correspond to different radial positions in the detection chamber, relative to the axis of rotation.

8. The system of claim 6, wherein a first gantry position is positioned radially outwardly of a second gantry position.

9. The system of claim 1 wherein the optical module is operatively positioned relative to the sample processing device via a gantry, and wherein the optical module is configured to be positioned at a predetermined gantry position, relative to the axis of rotation, and is further configured to optically interrogate the detection chamber at the predetermined gantry position.

10. The system of claim 9, wherein the detection chamber includes an inner boundary located nearest the axis of rotation, and wherein the optical module is configured to optically interrogate the detection chamber at a gantry position proximate the inner boundary of the detection chamber.

11. The system of claim 1, wherein the optical module is configured to optically interrogate the detection chamber to determine whether a selected volume of material is present in the detection chamber.

12. The system of claim 1, wherein the optical module is configured for multiplex fluorescence detection.

13. The system of claim 1, wherein the optical module is configured to determine whether a selected volume of material is present in the detection chamber by
 emitting an electromagnetic signal into the detection chamber, and
 detecting backscattered reflection of the electromagnetic signal.

14. The system of claim 1, wherein the optical module is configured to determine whether a selected volume of material is present in the detection chamber by
 emitting an electromagnetic signal into the detection chamber, and
 detecting fluorescence emitted by a material in the detection chamber.

15. The system of claim 1, wherein the optical module is configured to determine whether a selected volume of material is present in the detection chamber by
 emitting an electromagnetic signal into the detection chamber at a first wavelength, and
 detecting electromagnetic signals emitted from the detection chamber at a second wavelength, after emitting an electromagnetic signal into the detection chamber at a first wavelength.

16. The system of claim 1, wherein the optical module is further configured to determine an amount of material that is present in the detection chamber.

* * * * *